US008053637B2

(12) United States Patent
Mathews et al.

(10) Patent No.: US 8,053,637 B2

(45) Date of Patent: Nov. 8, 2011

(54) ***TAXUS* TRANSFORMATION TRANSFORMED CELLS, AND RELATED COMPOSITIONS AND METHODS**

(75) Inventors: Helena V. Mathews, Portland, OR (US); Vaka S. Reddy, Beaverton, OR (US); Allan H. Lammers, Portland, OR (US)

(73) Assignee: Dianaplantsciences, Inc., Portland, OR (US)

( * ) Notice: Subject to any disclaimer, the term of this patent is extended or adjusted under 35 U.S.C. 154(b) by 456 days.

(21) Appl. No.: 12/160,066

(22) PCT Filed: Jan. 3, 2007

(86) PCT No.: PCT/US2007/000222

§ 371 (c)(1), (2), (4) Date: Jul. 3, 2008

(87) PCT Pub. No.: WO2007/081772

PCT Pub. Date: Jul. 19, 2007

(65) Prior Publication Data

US 2009/0007298 A1 Jan. 1, 2009

Related U.S. Application Data

(60) Provisional application No. 60/756,444, filed on Jan. 4, 2006.

(51) Int. Cl.

| | |
|---|---|
| ***C12N 15/82*** | (2006.01) |
| ***C12N 5/10*** | (2006.01) |
| ***C12N 15/29*** | (2006.01) |
| ***C12N 15/54*** | (2006.01) |
| ***C12N 15/55*** | (2006.01) |
| ***C12N 15/61*** | (2006.01) |
| ***C12N 5/04*** | (2006.01) |
| ***C12P 17/02*** | (2006.01) |

(52) U.S. Cl. ........ 800/287; 435/123; 435/193; 435/195; 435/233; 435/422; 435/468

(58) Field of Classification Search ........................ None
See application file for complete search history.

(56) References Cited

U.S. PATENT DOCUMENTS

| | | | |
|---|---|---|---|
| 6,043,072 A * | 3/2000 | Croteau et al. | 435/193 |
| 6,054,635 A | 4/2000 | Bestwick et al. | |
| 6,118,049 A | 9/2000 | Bestwick et al. | |
| 6,288,302 B1 | 9/2001 | Yu et al. | |
| 6,331,416 B1 | 12/2001 | Shani et al. | |
| 6,392,122 B1 | 5/2002 | Clendennen et al. | |
| 6,642,438 B1 | 11/2003 | Clendennen et al. | |
| 2004/0064854 A1 | 4/2004 | Clendennen et al. | |

FOREIGN PATENT DOCUMENTS

| | | |
|---|---|---|
| KR | 0017370 | 1/2004 |
| WO | WO 00/28005 | 5/2000 |
| WO | WO2005/010166 | 2/2005 |

OTHER PUBLICATIONS

Furmanowa et al. Herba Polonica 44(4): 252-257 (1998).*

Mathews et al. In Vitro Cellular and Developmental Biology 31(1): 36-43 (Jan. 1995).*

Mathews et al. In Vitro Cellular and Developmental Biology (Plant) 28(4): 172-178 (Oct. 1992).*

Fils-Lycaon et al. Plant Physiology 111(1): 269-273 (May 1996).*

Han et al., "Genetic transformation of mature Taxus: An approach to genetically control the in vitro production of the anti cancer drug, taxol," *Plant Science*, 95(2):187-196, 1994.

Han et al., "XXI. Genetic transformation of taxus (yew) to improve production of taxol," *Biotechnology in Agriculture and Forestry—Transgenic Trees*, 44:291-306, 1999.

Jennewein et al., "Cytochrome P450 taxadiene 5alpha-hydroxylase, a mechanistically unusual monooxygenase catalyzing the first oxygenation step of taxol biosynthesis," *Chemistry & Biology*, 11(3):379-387, 2004.

Jennewein et al., "Random sequencing of an induced Taxus cell cDNA library for identification of clones involved in Taxol biosynthesis," *Proceedings of The National Academy of Sciences of the United States of America*, 101(24):9149-9154, 2004.

Jennewein et al., "Taxoid metabolism: Taxoid 14beta-hydroxylase is a cytochrome P450-dependent monooxygenase," *Archives of Biochemistry And Biophysics*, 413(2):262-270, 2003.

Ketchum et al., "Stable transformation and long-term maintenance of transgenic Taxus cell suspension cultures," *Plant Cell Reports*, 26(7):1025-1033, 2007.

Kim et al. "Expression of Modified Green Fluorescent Protein in Suspension Culture of Taxus Cuspidata," *Journal of Microbiology and Biotechnology*, 10(1):91-94, 2000.

An et al., "Binary vectors," *In Plant Molecular Biology Manual*, A3:1-19 (1988).

Becker et al., "New plant binary vectors with selectable markers located proximal to the left T-DNA border," *Plant Mol Biol*, 20:1195-1197 (1992).

Bommineni et al., "Transformation of white spruce (*Picea glauca*) somatic embryos by microprojectile bombardment," Plant *Cell Rep*, 13:17-23 (1993).

Brincat et al., "Alterations in Taxol production in plant cell culture via manipulation of the phenylalanine ammonia lyase pathway," *Biotechnol Prog*, 18:1149-56 (2002).

Chupeau et al., "Transgenic plants of lettuce (*Lactuca sativa*) obtained through electroporation of protoplasts," *Bio/Technol*, 7:503-508 (1989).

(Continued)

*Primary Examiner* — David T Fox

(74) *Attorney, Agent, or Firm* — Workman Nydegger

(57) ABSTRACT

Reported herein are methods for obtaining stably transformed callus in *Taxus media* 'Hicksii', including particularly methods that involve using needles, stem, or bark peel as explant material for transformation. Also provided are descriptions of several promoter activities in directing reporter gene expression in *Taxus media* cells, in particular cells in suspension cultures, callus and needles. Transgenic plants (e.g., *Taxus* plants), plant cells, cell lines, and tissues (including seeds) are also provided, in particular those that express one or more enzymes in a paclitaxel biosynthesis pathway.

19 Claims, 6 Drawing Sheets

OTHER PUBLICATIONS

Dong et al., "Enhanced taxane productivity in bioreactor cultivation of *Taxus chinensis* cells by combining elicitation, sucrose feeding, and ethylene incorporation," *Enz Microb Tech*, 31:116-121 (2002).
Ellis et al., "Expression of inducible angiosperm promoters in a gymnosperm, *Picea glauca* (white spruce)," *Plant Mol Biol*, 17:19-27 (1991).
Forward et al., "The Douglas-fir BiP promoter is functional in *Arabidopsis* and responds to wounding," *Planta*, 215:569-576 (Epub Apr. 19, 2002).
Furuya et al., "Production of tocopherols by cell culture of safflower," *Phytochemistry*, 26:2741-2747 (1987).
Garcia-Guevara et al., "The mannopine synthase promoter contains vectorial cis-regulatory elements that act as enhancers and silencers," *Mol Gen Genet*, 262:608-617 (1999).
Gibson et al., "Potential of plant cell culture for taxane production," in *Taxol: Science and Application*, (Stuffness, ed.), pp. 71-95, Boca Raton, New York, CRC Press (1995).
Huang et al., *Yunnan Zhiwu Yanjiu*, "Transformation of *Taxus brevifolia* by *Agobacterium rhizogenes* and taxol production in hairy roots culture," *Acta Botanica Yunnanica*, 19:292-296 (1997) In Chinese, contains English abstract.
Ketchum et al., "Recent progress toward an understanding of Taxol biosynthesis in plant cell cultures," in *Towards Natural Medicine Research in the 21st Century*, (Ageta, et al., eds.), Elsevier Sciences B. V. pp. 339-348 (1998).
Klein et al., "Stable genetic transformation of intact *Nicotiana* cells by the particle bombardment process," *PNAS* (*USA*), 85:8502-8505 (1988).
La Rue, "Studies on growth and regeneration in gametophytes and sporophytes of gymnosperms," in *Abnormal and Pathological Plant Growth, Report Symp Brookhaven National Laboratory*, J. Upton, New York, pp. 187-208 (1953).
Loopstra et al., "Agrobacterium-mediated DNA transfer in sugar pine," *Plant Mol Biol*, 15:1-9 (1990).
Luan et al., "Transient gus expression in zygotic embryos of *Taxus brevifolia,*" *In Vitro Cell Dev Biol Plant*, 32:81-85 (1996).
Miki et al., "Microinjection: An Experimental Tool for Studying and Modifying Plant CellsPlant," in *DNA Infectious Agents*, (Hohn et al., eds.), Springer-Verlag, Wien, Austria, pp. 249-265 (1987).
Roberts et al., "Large-scale plant cell culture," *Curr Op Biotech*, 8:154-159 (1997).
Robertson et al., "Genetic transformation of Norway spruce (*Picea abies* (L.) Karst) using somatic embryo explants by microprojectile bombardment," *Plant Mol Biol*, 19:925-935 (1992).
Sederoff et al., "Gene transfer into Loblolly pine by *Agrobacterium tumefaciens,*" *Bio/Technology*, 4:647-649 (1986).
Tabata, "Paclitaxel production by plant-cell-culture technology," *Adv Biochem Eng Biotechnol*, 7:1-23 (2004).
Takeya, "Plant tissue culture of taxoids," *Taxus*, (Itokawa and Lee eds.), Taylor and Francis Group, London and New York, pp. 134-150 (2003).
Tang et al., "Genetic transformation of conifers and its application in forest biotechnology," *Plant Cell Rep*, 22:1-15 (2003).
Vongpaseuthe et al., "Development of a particle bombardment-mediated transient transformation system for *Taxus* spp. cells in culture," *American Chem Soc and American Inst of Chem Eng* (Aug. 29, 2007).
Yukimune et al., "Methyl jasmonate-induced overproduction of paclitaxel and baccatin III in *Taxus* cell suspension cultures," *Nat Biotech*, 14:1129-1132 (1996).
Zhong, "Plant cell culture for production of paclitaxel and other taxanes," *J Biosci Bioeng*, 94:591-599 (2002).
Huang et al., "*Agrobacterium rhizogenes*-mediated genetic transformation and regeneration of a conifer: *Larix decidua,*" *In Vitro Cell Dev Biol*, 27:201-207 (1991).

* cited by examiner

A

B

C

A) Map of the pAG4015 showing probe region and primers for RT-PCR

5'-TGCCGAACTTGGTTCCTTATATAG-3'
(CsVMV.F1)

5'-AAGACGTGACGTAAGTATCCGAGT-3'
(MAS1'.R1)

CH29_869.F1: 5'-GGTCCATTATCCAGGAGG-3'

| | |
|---|---|
| TDS_430.R: | 5'-GACTGATATCTCCGTCTCC-3' |
| AtGGDPS1_449.R: | 5'-ATGGTGTGAATCATCTCG-3' |
| DXR_826.R: | 5'-GCAGTCAAAATTATACGCC-3' |
| T5H_389.R: | 5'-TCGTTGGACAGAATAAGC-3' |
| TAX2_442.R: | 5'-GAACAGTTAGAAGATGGAGG-3' |
| T13H_426.R: | 5'-AAACCGAGTTAGTGCAGC-3' |
| DXPS_489.R: | 5'-GAAAACGTGATGAAGTGC-3' |

*TAXUS* TRANSFORMATION TRANSFORMED CELLS, AND RELATED COMPOSITIONS AND METHODS

CROSS REFERENCE TO RELATED APPLICATIONS

This is the U.S. National Stage of International Application No. PCT/US2007/000222, filed Jan. 3, 2007, which was published in English under PCT Article 21(2), which in turn claims the benefit of U.S. Provisional Application No. 60/756,444, filed Jan. 4, 2006. Both applications are incorporated herein in their entirety.

FIELD OF THE DISCLOSURE

The present disclosure relates to plant transformation, and particularly to the long-term, stable transformation of plants of the genus *Taxus*. Also described are *Taxus* cells, cell lines, and plants produced using transformation methods provided herein, which cells, cell lines, and plants contain one or more transgenes. Methods of transient transformation are also described, as are methods and compositions useful in producing and maintaining transformed *Taxus* cells, cell lines, and plants, as well as methods and compositions useful in harvesting and/or extracting compounds therefrom.

BACKGROUND OF THE DISCLOSURE

Paclitaxel (TAXOL®) is an important anti-cancer drug initially isolated from *Taxus brevifolia*. It is a complex diterpenoid alkaloid found in several *Taxus* species (Wani et al., *J. Am. Chem. Soc.* 93: 2325-2327, 1971; Vidensek et al., *J. Nat. Prod.* 53: 1609-1610, 1990; Witherup et al., *J. Nat. Prod.* 53: 1249-1255, 1990; Mattina & Paiva, *J. Environ. Hortic.* 10: 187-191, 1992; Wheeler et al., *J. Nat. Prod.* 55: 432-440, 1992; Choi et al., *Planta Med.* 61: 264-266, 1994; Wickremesinhe & Arteca, *Plant Sci.* 101: 15-135, 1994; and Kwak et al., *Phytochemistry* 40: 29-32, 1995). Paclitaxel has the unique mechanism of action for stabilizing microtubules against depolymerization (Seki et al., *J. Chem. Eng. Jpn.* 28: 488-490, 1995). Microtubules are tubular protein polymers composed of two tubulin polypeptides; their dynamic behavior is important in cell proliferation. Paclitaxel blocks mitosis at the transition between the metaphase and anaphase by stabilizing the microtubules, which subsequently induces cell death (Jordan & Wilson, In *Taxane anticancer agents* (eds.) Georg et al., ACS symposium Series 583. American Chemical Society, Washington, D.C. pp. 138-153, 1995). The clinical trials of paclitaxel in patients with various types of cancers showed antineoplastic activities against ovarian, breast, lung, head, neck and gastrointestinal cancers (Holmes et al., In *Taxane anticancer agents*. Georg et al. (eds.) ACS symposium Series 583. American Chemical Society. Washington D.C. pp. 31-57, 1995).

The broad spectrum anticancer activity of paclitaxel accounts for its great demand in the pharmaceutical industry world wide. *Taxus* trees are grown in commercial nurseries, and the needles and stems are used to extract taxanes which are used as semi-synthetic sources of paclitaxel (Joyce, *Bioscience* 43: 133-136, 1993; Wheeler & Hehnen, *J. For.* 91: 15-18, 1993). However, the supply of the drug is limited as the *Taxus* species are slow growing gymnosperms and the content of paclitaxel in the bark of the trees is relatively low (0.01% on dry weight basis). The conventional breeding strategy for genetic improvement of *Taxus* is not a feasible approach due to the heterozygosity of the genome, slow growth and long generation time of the species. Cell and tissue culture techniques offer an alternative system for paclitaxel production. In the 1950s, La Rue (In *Abnormal and pathological plant growth*, Report Symp. Brookhaven National Laboratory, J Upton, N.Y., pp 187-208, 1953) and Tulecke (Tulecke, *Bull. Torry Bot. Club.* 86: 283-289, 1959) initiated approaches to *Taxus* plant cell and tissue culture. The *Taxus* cells are known to grow slowly during initial subcultures, tend to turn brown within 8-10 months and growth stops. But recovery of fresh cells from brown callus has been reported after 1-2 years (Gibson et al., In *Taxol: Science and Application*, Stuffness (ed.) pp. 71-95. Boca Raton, N.Y.: CRC Press, 1995). At present, the production capability of paclitaxel and related taxanes using cell and tissue culture has been established and the conditions suitable for fast growing cultures to produce high levels of paclitaxel have been studied in commercial production (Takeya, In *Taxus*, Itokawa and Lee (eds). Taylor and Francis Group, London and New York. Pp 134-150, 2003). However the low productivity of paclitaxel combined with consistent variability is a major concern in realizing the full potential of producing this drug in cell cultures. Metabolic engineering appears an attractive route to enhance the paclitaxel production in cell cultures especially with the elucidation of the paclitaxel biosynthetic pathways in the recent past (Ketchum & Croteau, In *Towards Natural Medicine Research in the* 21*st* *Century*. Ageta et al. (eds.), Elsevier Sciences B. V. pp 339-348, 1998). The success of this approach is dependent on the establishment of a viable transformation system in *Taxus*. Although several conifers have been transformed by *Agrobacterium* (Sederoff et al., *Bio/Technology* 4: 647-649, 1986; Loopstra et al., *Plant Mol. Biol.* 15:1-9, 1990; and Huang et al., *In Vitro Cell. Dev. Biol.* 27: 201-207, 1991) and particle bombardment (Robertson et al., *Plant Mol. Biol.* 19: 925-935, 1992; Ellis et al., *Bio/Technology* 11: 84-89, 1993), there is very limited success in *Taxus* transformation. Tumor induction using wild strains of *agrobacterium tumefaciens* has been reported in *Taxus brevifolia* and *Taxus baccata* (Han et al., *Plant Sci.* 95: 187-196, 1994; Han et al., In *Biotechnology in Agriculture and Forestry*, Vol. 44 Transgenic Trees. Bajaj (ed.) Chapter XXI. pp 291-306, 1999). Transient expression of Gus reporter gene in zygotic embryos of *Taxus brevifolia* was reported by Luan et al. (*In Vitro Cell. Dev Biol Plant* 32: 81-85, 1996). Similar transient expression of GFP (green fluorescent protein) was obtained in *Taxus cuspidata* callus, that was sustained for three months in culture (Kim et al., *J. Microbiol. Biotechnol.* 10: 91-94, 2000). The use of *Agrobacterium rhizogenes* for hairy root induction was yet another attempt towards transformation of the *Taxus* species (Huang et al., *Yunnan Zhiwu Yanjiu,* 19: 292-296, 1997; Zunxi et al., *Acta Botanica Yunnanica* 19: 292-296, 1997).

Development of a stable transformation system for *Taxus* is critical for enhanced production of paclitaxel by genetic engineering strategy.

SUMMARY OF THE DISCLOSURE

Reported herein are methods for obtaining stably transformed callus in *Taxus media* 'Hicksii', and for obtaining transformed callus in *Taxus bacatta*. To our knowledge, this is the first report on the stable transformation of *Taxus* species (e.g., *Taxus media* 'Hicksii'). Earlier reports on transformation of *Taxus* species are limited to tumor induction with wild strains of *Agrobacterium* or transient expression of transgenes. Also provided herein are descriptions of several promoter activities useful in directing heterologous gene expression in *Taxus media* cell suspension cultures, callus and needles.

The disclosure provides, in one embodiment, a method for obtaining transgenic callus in *Taxus* species. *Taxus media* 'Hicksii' has been transformed with *Agrobacterium tumefaciens* strains GV3101 or EHA101 with plasmid pAG4015 and pAG4017, containing the nptII gene under the transcriptional control of CsVMV promoter and Gus gene under the control of melon actin promoter with or without a heterologous intron sequence between the promoter and Gus coding sequences. Stable integration of Gus gene into *Taxus media* 'Hicksii' has been obtained using "bark peel", a novel explant source for genetic transformation of *Taxus*, as well as other plant tissue explants, e.g. peeled stem. The transformed calli were screened on medium containing as a selection antibiotic kanamycin/geneticin. The selected calli tested positive on X-Gluc histochemical assay, confirming the presence of β-glucuronidase enzyme produced by the transformed tissue. The genomic integration of transgenes nptII and Gus was further confirmed by PCR analysis and Southern hybridization. Expression of the Gus transcript was further confirmed by RT-PCR.

The present disclosure further provides a method for producing transgenic callus from *Taxus* species. In an embodiment of the method, a vector (e.g., a transformation or expression vector) having at least a first DNA sequence that encodes a gene encoding a selectable marker functional in plant cells is introduced into cells of a target explant. This first DNA sequence is flanked by regulatory elements effective to allow expression of the sequence in plant host cells. Further, expression of this selectable marker gene produces a gene product that confers the ability of plant cells expressing the gene to grow in the presence of a selective agent. Exemplary selective agents include hygromycin, geneticin (G418) and kanamycin. Exemplary selectable marker genes include NPTII.

In one embodiment, the transformation vector is an *Agrobacterium*-type vector.

In some embodiments, the transformation vector is introduced into cells of a target *Taxus* tissue explant under conditions to generate transformation of explant cells. In one embodiment, the vector is introduced by co-culturing a target explant in the presence of *Agrobacterium* containing the vector under conditions to generate transformation of explant cells by the vector. Typically, the co-culturing is carried out in liquid medium for from about one to about three days. Introduction of the vector into plant cells can also be carried out by other means, including, but not limited to, the following direct transformation methods: electroporation, microinjection, and microprojectile bombardment.

The *Taxus* tissue explant can be obtained from a variety of tissues including, but not limited to, needles, stem, bark, bark peel, peeled stem, embryos and meristem. In certain embodiments, bark peel or peeled stem explants are beneficially employed.

Transformed explant cells can be screened for their ability to be cultured in selective media having a threshold concentration of selective agent(s). Explants that produce callus that can grow on the selective media are typically transferred to a fresh supply of the same media and cultured again. The resultant calli are then cultured on a higher concentration of selective agent(s). This iterative culture (or "iterative subculture") method is repeated until pure transgenic calli are obtained.

In one embodiment, transgenic calli (such as pure transgenic calli, that is, lacking significant contamination with non-transgenic cells) are identified by carrying out iterative subculture where the calli are subjected to continuous selection pressure and necrotic cells, if any, are discarded during the subculture process. In the presence of selective agent, there is no necrosis or significant bleaching of transformed callus tissue.

Vectors used in methods of the present disclosure may also include further DNA coding sequences, for example, a second DNA sequence which is flanked by regulatory elements effective to allow expression of the sequence in plant cells. This second DNA sequence can encode any number of useful gene products including products useful to increase paclitaxel content in transgenic cells (e.g., a biosynthetic or regulatory protein), or a screenable marker (such as GUS or GFP) that can be used to confirm integration of transgene(s) into the genome of *Taxus* cells and expression of transgene(s).

Regulatory elements for use in the practice of the described methods typically include transcriptional and translational initiation/termination signals. In one embodiment, the transcription regulatory elements include heterologous or homologous promoters. Examples of heterologous promoters can be derived from viral, bacterial and plant cells. Examples of each group include, but not limited to, CsVMV, mas1' and mACTIN. Other appropriate promoters are described herein; yet others will be known to those of skill in the art.

The transgenic cells of the present disclosure can embody many modifications, including, but not limited to, increased paclitaxel content, reduced biosynthetic pathway intermediates or reduced byproducts such as other taxanes that do not yield paclitaxel. In one embodiment such modifications of taxane profiles can be achieved by expression of genes coding for paclitaxel biosynthetic pathway enzymes such as deoxyxylulose phosphate synthase (DXS), deoxyxylulose phosphate reductoisomerase (DXR), geranylgeranyldiphosphate synthase (GGDPS), taxadiene synthase (TDS), taxadienol acetyl transferase (TAX1), taxane-2-alpha-O-benzoyltransferase (TAX2), 10-DABIII-10-O-acetyltransferase (TAX6), phenylpropanyltransferase (TAX7), benzoyltransferase (TAX10), 10-beta-hydroxylase, 13-alpha-hydroxylase, taxoid-14-beta-hydroxylase and/or 5-alpha-hydroxylase. In another embodiment, genes (e.g., encoding transcription factors) that regulate or influence the paclitaxel biosynthetic pathway, including for instance a rate controlling step of the paclitaxel biosynthetic pathway, may be used to transform *Taxus* cells to modify the taxanes profiles of such genetically engineered cells.

Also described are methods of generating stable transgenic plant cells, cell cultures and cell lines, including but not limited to *Taxus* cells, cell cultures, and cell lines that express one or more heterologous genes. In particular embodiments, the heterologous genes are selected from genes that encode an enzyme in a pathway responsible for paclitaxel biosynthesis or a transcription factor that regulates the expression of one or more steps (such as a rate controlling step) of the biosynthetic pathway. Also provided are stable transgenic plant cells, cell cultures, and cell lines with modified, in particular enhanced, production of one or more taxanes, and methods for extracting (or harvesting) said taxanes.

The present disclosure further summarizes several promoter activities useful in directing reporter and other gene expression in *Taxus media* cell suspension cultures and callus and needles of *Taxus bacatta*. The activity of 15 promoters was determined in *Taxus media* 'Hicksii' by particle bombardment assay with chimeric genes comprising heterologous promoters fused to the GUS reporter coding region and the NOS terminator. The GUS reporter assay revealed that the tested promoters differed in their activity in directing GUS reporter gene expression in *Taxus* cells. The disclosure thus further relates to expression of heterologous genes in *Taxus* tissues, and utilization of these promoters in generating transgenic *Taxus.*

Applicants have identified 15 promoter sequences that activate GUS reporter gene expression in cell suspension cultures, and callus tissues of *Taxus media* 'Hicksii' and needles of *Taxus baccata.*

In one embodiment, there is provided CsVMV promoter that activates GUS gene expression in cell suspension cultures, callus and needle tissues of *Taxus media* 'Hicksii'. Further, mACTIN promoter is able to activate GUS gene expression in cell suspension and callus tissues. As described herein, CsVMV promoter is stronger than mACTIN promoter in these callus and cell suspension cultures.

In exemplary aspects of this embodiment, CsVMV (SEQ ID NO: 9) and mACTIN (SEQ ID NO: 14) promoter sequences are provided herein.

Also demonstrated and/or described herein are comparative promoter activity of CsVMV, MAS1', E8-E4, TRX-mACTIN, CmAco and RE4 promoters, or sequences derived from these promoters, in activating gene expression (e.g., GUS expression) in cell suspension cultures of *Taxus media* 'Hicksii'. Exemplary MAS1' (SEQ ID NO: 10), E8-E4 (SEQ ID NO: 13), TRX-mACTIN (SEQ ID NO: 16), CmAco (SEQ ID NO: 20) and RE4 (SEQ ID NO: 22) promoter sequences are provided herein.

Another embodiment provides comparative promoter activity of CsVMV, Cherry 29 (CH29), A7, TRX, Thi 1.3-mACTIN, Thi 1, DRU, MADS2, PRU and a synthetic promoter, each useful in activating gene expression, such as the GUS reporter gene in cell suspension cultures of *Taxus media* 'Hicksii'. Exemplary CH29(SEQ ID NO: 12), A7 (SEQ ID NO: 11), TRX (SEQ ID NO: 15), Thi 1.3-mACTIN (SEQ ID NO: 18), Thi1 (SEQ ID NO: 17), DRU (SEQ ID NO: 19), MADS2 (SEQ ID NO: 21), PRU (SEQ ID NO: 23) and a synthetic promoter (SEQ ID NO: 24) sequences are provided herein.

Another embodiment provides comparative strength of 16 promoters in activating heterologous GUS gene expression in the gymnosperm *Taxus*, the plant is known to produce paclitaxel anticancer drug. Exemplary comparative promoter strength of 16 tested promoters in cell suspension cultures is provided, as presented in Table 6.

Another embodiment demonstrates the utility of 15 promoters in activating expression of any heterologous or chimeric protein coding genes in any tissues of *Taxus* species. The protein coding genes include, but are not limited to, enzymes of the paclitaxel biosynthetic pathway or related branch or intermediate pathways, or any secondary metabolite biosynthetic pathway of *Taxus* species or any plant genes.

In another embodiment, the disclosure describes utilization of any of 15 promoters in *Taxus* transformation vectors or plant expression binary vectors, for generation of transgenic *Taxus* plants. Transgenic *Taxus* plants can be generated through various methods, including *Agrobacterium*-based methods, electroporation, microinjection, and microprojectile bombardment.

The foregoing and other features and advantages will become more apparent from the following detailed description of several embodiments, which proceeds with reference to the accompanying figures.

BRIEF DESCRIPTION OF FIGURES

FIG. 1B: pAG4017), showing orientation and structure of promoter:gene fusions. The location of the intron in GUS is shown in pAG4017.

FIG. 2A: PCR confirmation of nptII transgene: Lane 1—transgenic callus; Lane 2—wild type; Lane 3—positive control, plasmid pAG4015; Lane 4—positive control, plasmid pME4100. FIG. 2B: Endogenous control for taxadiene synthase gene: Lane 1—transgenic callus; Lane 2—wild type; Lane 4—taxadiene synthase cDNA template; FIG. 2C: PCR confirmation of Gus transgene: Lane 1—transgenic callus; Lane 2—wild type; Lane 3—positive control, plasmid pAG4015.

FIG. 5A: Map of pAG4015 showing probe region and primers for RT-PCR. FIG. 5B: Southern blot analysis of the *T. media* transformed with pAG4015. Genomic DNA was digested with EcoRI, separated on 0.8% agarose gel, blotted to Nylon membrane and probed with 485 bp mACTIN:GUS junction region as shown in A. FIG. 5C: Identification of GUS transcript by SYBR RT-PCR analysis in transgenic *T. media* line expressing mACTIN:GUS (pAG4015 vector)

FIG. 6A: Map of the T-DNA region of the MAS1'-based *Taxus* plant expression vectors and primers (SEQ ID NOs: 57 and 58) (indicated in arrows) used to screen for transgenics by genomic PCR. FIG. 6B: Map of the T-DNA region of the CH29-based *Taxus* plant expression vectors and primers (SEQ ID NOs: 59-66) (indicated in arrows) used to screen for transgenics by genomic PCR.

FIG. 7A: Map of the TDS gene expressed with either MAS1' or Ch29 promoter and primer positions for RT-PCR analysis. Partial sequence of TDS is shown (SEQ ID NO: 69). FIG. 7B: RT-PCR analysis of the transgenic lines transformed with either CH29:TDS (pME4300) or MAS1': TDS (pME4100).

SEQUENCE LISTING

Figure 1A:
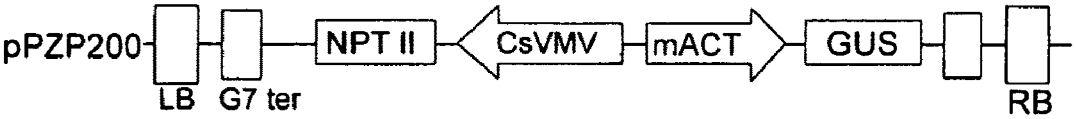
FIGS. 1A-1B show graphic maps of two T-DNA inserts (FIG. 1A: pAG4015.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Public database Accession numbers provided herein are understood to apply to the release of the referenced sequence available as of the day this application is filed. In the accompanying sequence listing:

SEQ ID NOs: 1 through 8 show the nucleic acid sequence of various primers.

SEQ ID NO: 9 shows a nucleic acid sequence including a Cassava vein mosaic virus (CsVMV) promoter (Exelixis Plant Sciences (EPS) plasmid # pAG153); the promoter is at positions 1-522.

SEQ ID NO: 10 shows a nucleic acid sequence including a mannopine synthase (MAS1') gene promoter (EPS plasmid # pAG740); the promoter is at positions 1-484.

SEQ ID NO: 11 shows a nucleic acid sequence including the lettuce A7 promoter (EPS plasmid # pAG742); the promoter is at positions 1-2405.

SEQ ID NO: 12 shows a nucleic acid sequence including the CH29 (thaumatin-like) gene promoter (EPS plasmid # pAG133); the promoter is at positions 1-1252.

SEQ ID NO: 13 shows a nucleic acid sequence including the tomato E8-E4 hybrid promoter (EPS plasmid # pAG134M); the promoter is at positions 1-2321. The "N" at position 884 indicates that any nucleotide can occur at that position.

SEQ ID NO: 14 shows a nucleic acid sequence including the melon actin (mACTIN) promoter, with an intron sequence (EPS plasmid # pAG167); the promoter is at positions 1-1529.

SEQ ID NO: 15 shows a nucleic acid sequence including the banana thioredoxin (TRX) gene promoter (EPS plasmid # pAG159); the promoter is at positions 1-972.

SEQ ID NO: 16 shows a nucleic acid sequence including the hybrid banana thioredoxin gene and mACTIN promoter (TRX:mACTIN) (EPS plasmid # pAG749) the promoter is at positions 1-1889.

SEQ ID NO: 17 shows a nucleic acid sequence including the Fuji apple thiamine synthase gene promoter (EPS plasmid # pAG162a) the promoter is at positions 1-978.

SEQ ID NO: 18 shows a nucleic acid sequence including the hybrid Fuji apple thiamine synthase gene and mACT promoter (Thi 1.3:mACTIN) (EPS plasmid # pAG752); the promoter is at positions 1-2047.

SEQ ID NO: 19 shows a nucleic acid sequence including the *Cucumis melo* DRU (drupe-specific) gene promoter (EPS plasmid # pAG154); the promoter is at positions 1-1659.

SEQ ID NO: 20 shows a nucleic acid sequence including the *Cucumis melo* ACC oxidase I gene promoter (EPS plasmid # pAG152M); the promoter is at positions 1-1352.

SEQ ID NO: 21 shows a nucleic acid sequence including the Fuji apple MADS2 gene promoter (EPS plasmid # pAG168); the promoter is at positions 1-1034.

SEQ ID NO: 22 shows a nucleic acid sequence including the raspberry E4 gene homolog promoter sequence (EPS plasmid # pAG138M); the promoter is at positions 1-951.

SEQ ID NO: 23 shows a nucleic acid sequence including the PRU gene promoter sequence (EPS plasmid # pAG4021); the promoter is at positions 1-1259.

SEQ ID NO: 24 shows a nucleic acid sequence including a synthetic promoter sequence (EPS plasmid # pAG139C); the promoter is at positions 1-377.

SEQ ID NO: 25 shows the nucleic acid sequence of a promoterless construct (for use with GUS coding sequence but without any promoter (EPS plasmid # pAG147)) used as control in transient assays with *Taxus media* 'Hicksii' tissues.

SEQ ID NOs: 26 through 68 show the nucleic acid sequence of various primers.

SEQ ID NO: 69 shows a partial sequence of TDS.

DETAILED DESCRIPTION

I. Abbreviations

| | |
|---|---|
| A7 promoter | lettuce A7 promoter |
| CH29 promoter | Cherry 29 (thaumatin-like gene) promoter |
| CmAco promoter | *Cucumis melo* ACC oxidase gene promoter |
| CsVMV promoter | Cassava Vein Mosaic Virus promoter |
| DRU promoter | *Cucumis melo* DRU (drupe-specific) gene promoter |
| DXS | deoxyxylulose phosphate synthase |
| DXR | deoxyxylulose phosphate reductoisomerase |
| E8-E4 promoter | hybrid promoter from tomato E8 and E4 genes |
| GGDPS | geranylgeranyldiphosphate synthase |
| GUS | β-D-glucuronidase |
| mACTIN promoter | melon actin gene promoter |
| MADS2 promoter | Fuji apple MADS2 gene promoter |
| MAS 1' promoter | *Agrobacterium* mannopine synthase gene promoter |
| PRU promoter | cherry Prunin 12S globulin seed storage protein promoter |
| RE4 promoter | raspberry E4 gene homolog (RE4) promoter |
| TAX1 | taxadienol acetyl transferase |
| TAX2 | taxane-2-alpha-O-benzoyltransferase |
| TAX6 | 10-DABIII-10-O-acetyltransferase |
| TAX7 | phenylpropanyltransferase |
| TAX10 | benzoyltransferase |
| TDS | taxadiene synthase |
| Thi1 promoter | Fuji apple thiamine synthase (Thi 1) gene promoter |
| Thi 1.3-mACT promoter | apple thiamine synthase gene and melon ACT gene hybrid promoter |
| TRX promoter | banana thioredoxin-like (TRX) gene promoter |
| TRX-mACTIN promoter | banana thioredoxin-like gene and melon ACT gene hybrid promoter |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following non-limiting explanations of specific terms are provided:

cDNA (complementary DNA) is a piece of DNA lacking internal, non-coding segments (introns) and regulatory sequences that determine transcription. cDNA is synthesized in the laboratory by reverse transcription from messenger RNA extracted from cells.

As used herein, the terms "chimeric gene construct" and "chimeric nucleic acid construct" are used interchangeably and refer to recombinant nucleic acid sequences which comprise a nucleic acid coding sequence and control sequences required for expression of the coding sequence in a plant cell.

Expression levels can be measured by linking the promoter to a suitable reporter gene such as GUS (β-D-glucuronidase). Expression of the reporter gene can be easily measured by fluorometric, spectrophotometric or histochemical assays (Jefferson et al., *The EMBO Journal* 6(13):3901-3907, 1987; Jefferson, *Plant Mol Biol Rep.* 5: 387-405, 1987; Jefferson, *Nature* 342(6251) 837-838, 1989).

"Expression" is the process by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased).

"Foreign" nucleic acids are nucleic acids that would not normally be present in the host cell, particularly nucleic acids that have been modified by recombinant DNA techniques. The term "foreign" nucleic acid also includes host genes that are placed under the control of a new promoter or terminator sequence, for example, by conventional techniques.

"Functional gene" is any gene introduced into plants that can express its encoded sequences and produce the expected gene product, such as an RNA or protein, in the plant cells in which it resides.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Transient expression" refers to expression at a time, place, and/or increased level that does not naturally occur in the non-altered or wild-type plant.

A "heterologous" nucleic acid construct or sequence has a portion of the sequence that is not native to the plant cell in which it is expressed. Heterologous, with respect to a control sequence refers to a control sequence (i.e. promoter) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules.

As used herein, the terms "native" and "wild-type" relative to a given plant trait or phenotype refers to the form in which that trait or phenotype is found in the same variety of plant in nature.

As used herein, the term "operably linked" relative to a recombinant DNA construct or vector means nucleotide components of the recombinant DNA construct or vector are in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

An ORF (open reading frame) is a series of nucleotide triplets (codons) coding for amino acids without any internal termination codons. These sequences are usually translatable into a peptide.

The term "plant" encompasses transformed plants, progeny of such transformed plants, and parts of plants, including reproductive units of a plant, fruit, flowers, seeds, etc. The transformation methods and compositions of the present invention are particularly useful for transformation of gymnosperms, such as *Taxus* species. Other plants, including angiosperms, such as species of monocotyledonous and dicotyledonous plants may also be transformed using the disclosed methods.

As used herein, a "plant cell" refers to any cell derived from (and/or present in) a plant, including cells from undifferentiated tissue (e.g., callus and cell suspension cultures) as well as plant seeds, pollen, propagules, embryos, stem, and needles.

The term "purified" does not require absolute purity; rather, it is intended as a relative term. Thus, for example, a purified specific protein preparation is one in which the specific protein is more enriched than the protein is in its natural environment within a cell. Generally, a preparation of specific protein is purified such that the protein represents at least 5% of the total protein content of the preparation. For particular applications, higher purity may be desired, such that preparations in which the specific protein represents at least 25%, 50% or at least 90% of the total protein content may be employed.

As used herein, "promoter strength" refers to the level of promoter-regulated expression of a chimeric or heterologous gene in a plant tissue or tissues, relative to a suitable standard (e.g., a fruit-associated promoter from a particular plant, such as apple, versus a control or standard gene promoter, for example, the CsVMV promoter (Cassava Vein Mosaic Virus promoter; Verdaguer et al., *Plant Mol Biol.* 37:1055-1067, 1998) or promoter-less GUS.

"Pure transgenic explant (or callus)" or "Non-chimeric transgenic explant (or callus)" is a callus that contains essentially only transformed cells, determined as follows: Explants with transformed cells are cultured (or subcultured) in the presence of a selection agent to form callus. The calli are divided into subunits, which are cultured (or subcultured) under selective conditions as calli. If some number or portion of the subcultured calli are susceptible to the effects of the selective agent, the parent callus is considered to be chimeric, i.e., containing both transformed and non-transformed cells. If all of the subcultured calli are not susceptible to the effects of the selective agent, the parent callus is "pure" or "non-chimeric".

Transformed callus is, in some instances, screened by continuous exposure to selection pressure. On repeated subcultures, non-transformed areas of the callus become brown and cease to proliferate. At this stage, the callus is taken into liquid selection medium (a more stringent selection step) to eliminate non-transformed cells. Actively proliferating suspension cultures in liquid selection medium become the source for homogeneously transformed tissues.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

A "regulatable promoter" is one whose activity is regulated by an agent, such as a transcription factor, a chemical compound, or a nucleic acid molecule. It will be understood that regulatable promoters include those influenced by environmental factors and growth progression or stage.

The phrase "regulating gene expression refers to processes of controlling the expression of a gene by increasing or decreasing the expression, production, or activity of an agent that affects gene expression. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

A "reproductive unit" of a plant is any totipotent part or tissue of the plant from which one can obtain progeny of the plant, including, for example, seeds, cuttings, tubers, buds, bulbs, somatic embryos, microspores, and cultured cells (e.g., callus or suspension cultures).

A cell, tissue, organ, or organism into which a foreign nucleic acid, such as a recombinant nucleic acid molecule (e.g., a recombinant vector), has been introduced is considered "transformed" or "transgenic," as is progeny thereof in which the foreign nucleic acid is present. A transformed tissue or plant may include some cells that are not transformed, i.e., may be chimeric, comprising transformed and untransformed cells. Such chimeric tissues may be used to regenerate transformed plants, and may be advantageous for this purpose since less in vitro propagation and selection will be required to produce chimeric tissues than tissues in which 100% of the cells are transformed. Regeneration of chimeric tissues generally will give rise to chimeric plants, i.e., plants comprised of transformed and non-transformed cells. Reproduction of these chimeric plants by asexual or sexual means may be employed to obtain plants entirely comprised of transformed cells.

As used herein, the term transformation encompasses all techniques by which a nucleic acid molecule (e.g., a recombinant nucleic acid molecule) might be introduced into such a cell, including transfection with viral vectors, transformation with plasmid vectors, and introduction of naked DNA by electroporation, lipofection, and particle gun acceleration.

In methods involving co-cultivation of plant cells (e.g., plant suspension or callus culture cells) with an *Agrobacterium*, the length of time necessary for co-cultivation is generally at least that length of time needed to transfer a complete T-DNA molecule from the bacterium to the plant cells. At a minimum, this is generally thought to be about 36 hours. However, to encourage higher efficiency transformation, usually the plant and bacteria cells will be co-cultivated for at least 48 hours. Additional time in co-cultivation may be appropriate in certain circumstances, such as at least 60 hours, at least 72 hours, or at least 84 hours. In one embodiment, *Agrobacterium* cells are incubated with plant cells, such as plant suspension or callus cells, for about 72 hours.

Thus, the term "transgenic" with regard to a plant, fungus, cell, or other entity refers to a plant/fungus/cell/other entity that contains recombinant genetic material not normally found in entities of the reference type and which has been introduced into the entity in question (or into progenitors of the entity) by human manipulation. Thus, a plant that is grown from a plant cell into which recombinant DNA is introduced by transformation is a transgenic plant, as are all offspring of that plant that contain the introduced transgene (whether produced sexually or asexually).

As used herein, the term "transgenic plant" refers to a plant that contains recombinant genetic material not normally found in plants of this type and which has been introduced into the plant in question (or into progenitors of the plant) by human manipulation. Thus, a plant that is grown from a plant cell into which recombinant nucleic acid is introduced by transformation is a transgenic plant, as are all offspring of that plant that contain the introduced transgene (whether produced sexually or asexually).

"Threshold concentration of selective agent" varies depending on the selective agent used and is determined by experimentation. The threshold concentration is the concentration of the selective agent that permits the growth of transformed cells carrying the selection gene, but which also allows either very low level (background growth) or no growth of non-transformed cells. The threshold concentration is typically the lowest concentration of selective agent that significantly inhibits the growth of non-transformed cells.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Transformation Methods

The present disclosure includes a method for the generation of transformed plant cells from *Taxus* species.

In a method of the present disclosure, a suitable expression vector is selected for introduction into the cells of the target explant. The expression vector typically has at least one DNA sequence that encodes a gene encoding a selectable marker functional in plant cells. Such selectable markers are known to those of skill in the art and include the hpt gene (which confers resistance to the antibiotic hygromycin; *Klebsiella* sp.), and the nptll gene (originally obtained from TN5, having broad host range, conferring resistance to geneticin and kanamycin).

Expression of the selectable marker is typically under the control of a promoter that functions constitutively in plant cells (e.g., Pnos). Expression of the selectable marker gene produces a gene product that confers the ability of plant cells expressing the gene to grow in the presence of a selective agent (e.g., geneticin).

Plant explants are typically the target of transformation. The expression vector can be introduced into the explant cells by a number of methods including electroporation, microinjection, and microprojectile bombardment. These methods are well known in the art (Klein et al. *PNAS* (USA) 85(22): 8502-8505 1988; Miki et al., *Plant DNA Infectious Agents* (Hohn et al., eds.) Springer-Verlag, Wien, Austria, pp. 249-265, 1987; Bellini et al., *Bio/Technol.* 7(5): 503-508, 1989) and provide the means to introduce selected DNA into plant genomes.

In a preferred embodiment, the expression vector is an *Agrobacterium*-based vector and the transformation of the explant cells is carried out by co-culturing the explant in the presence of *Agrobacterium* carrying the expression vector. Numerous such *Agrobacterium* based vector systems are available to one of ordinary skill in the art (e.g., An et al., "Binary Vectors", in *Plant Molecular Biology Manual A*3: 1-19, 1988; Becker et al., *Plant Mol. Biol.* 20: 1195-1197, 1992).

Co-culturing of the explant and vector-bearing bacteria is typically carried out in liquid culture, under the conditions described below, for about 1 to 3 days. The concentration of the *Agrobacterium* in co-cultivation is typically between about $10^8$ to about $10^9$ transformed bacterial cells/ml of culture. By way of example, in some Examples described below the concentration is usually about $0.5\text{-}0.6\times10^9$.

After transformation of explant cells, the transformed cells are screened for the presence of the selectable marker gene by culturing the transformed explants (or callus resulting therefrom) in selective media having a threshold concentration of selective agent.

In the practice of the present invention, the ability of explants to produce transformed callus (or regenerate transformed tissues) is empirically evaluated. Having a robust regeneration system provides the maximum opportunity to recover transgenic calli from transformed explant cells. Some factors affecting regeneration ability include, but are not limited to, the following: media composition, hormone levels, concentration of selective agent, light levels, number of transfers to new culture media.

The ability to obtain transformed calli (and optionally regenerated plant tissues) from explants is maximized for the plant cells that are the selected transformation target. Different tissue explants may be transformed and the different tissues may respond differently to different culturing, subculturing, and/or regeneration conditions. In the method of the present disclosure, needles, stem pieces, peeled stem, and bark peel explants were routinely used.

One aspect of the present disclosure is the application of an iterative culture/selection method. The explant that has the ability for cell proliferation at the wounded site (presumed as the transformed region) is maintained on the medium with selection agent, such as an antibiotic. The callus resulting from cell proliferation is isolated and subsequently transferred to medium at the same or higher concentration of antibiotic; that is, subcultured. The iterative culture selection method is continued, providing increasingly stringent selection levels.

As described above, the threshold concentration of selective agent is determined. Typically, the first round of the iterative selection method is carried out at twice the threshold concentration, the second round at three times the threshold concentration, and so on. Any step-wise increase in selective agent concentration can be used, for example, 1×, 1.5×, 2×, 2.5× threshold concentrations.

Selective agent concentration is often explant tissue type dependent. Selective agent concentrations are typically in the range of 1-500 mg/l, but are, of course, dependent on the agent, explant-type, and selectable marker used.

The iterative culture method is repeated until pure (non-chimeric) transgenic calli are obtained. Briefly, a transformed callus that is the product of iterative selection is encouraged to undergo further proliferation, for example, by culturing callus subunits on proliferation medium.

The transgenic tissue is considered to be homogenous if all of the callus in liquid selection medium gives rise to creamy, proliferating suspension cultures.

Transgenic tissue also may be evaluated by standard recombinant techniques to demonstrate the presence of the introduced genes (e.g., genomic DNA PCR and RT-PCR analysis, for instance as described below).

In practicing methods of the present disclosure, the concentration of the selective agent in the first round selection should be carefully selected to allow growth of the transformed cells, and typically low level or background growth of some non-transformed cells. From this initial selection, the explant is usually subjected to callus proliferation, followed by a step-up selection (i.e., increased concentration of selective agent). Callus development ensues. The callus is usually transferred to new medium, and then transferred to another step-up concentration of selective agent.

As an initial test of the purity of the transgenic cells, after callus proliferation, callus tissue is chopped up and placed in selection media. If part of the callus (that is, some of the callus subunits) is susceptible to the effects of the selection media (e.g., exhibit necrosis), then the tissue is presumed not to be pure (that is, is presumed to be chimeric).

In addition to the selectable marker sequences, vectors used in the method of the present invention typically have at least one second DNA sequence that encodes a functional gene. The functional gene is flanked by regulatory elements effective to allow expression of the sequence in plant cells (e.g., transcription initiation/termination signals, translation initiation/termination signals). In specific examples, the regulatory elements include a promoter.

Gene products which may be useful to express include functional genes encoding (i) paclitaxel biosynthetic pathway genes and/or (ii) screenable marker genes, such as GUS or GFP.

The regulatory regions used to guide expression of gene products can also be obtained from a number of sources. Both constitutive and regulatable promoters are useful in the practice of the methods of the present invention. A tissue or stage specific promoter is a region of DNA that regulates transcription of the immediately adjacent (downstream) gene to a specific plant tissue or developmental stage of the plant or plant tissue.

The transformation method of the present invention is applicable to essentially all *Taxus* species and cultivars, including, but not limited to, *Taxus media*. One such cultivar is exemplified by *Taxus media* 'Hicksii'.

IV. Angiosperm, Viral and *Agrobacterium* Gene Promoters for Expression of Transgenes in *Taxus*

The 5' non-coding regions of a gene, referred to as promoters or transcriptional regulatory regions, initiate transcription of the gene to produce an mRNA transcript. These regulatory elements include "TATA box" and "CAAT box" along with other DNA sequence ranging from 400 bp to 2 kb or more (Lessard et al., *Metab. Eng.* 4:67-79, 2002). These elements participate in regulating gene expression when fused to the 5' end of coding regions and therefore serve as promoters to drive expression of gene of interest The mRNA is then translated at the ribosomes of the cell to yield an encoded polypeptide. Promoters typically contain from about 500-1500 bases, and can provide regulated expression of genes under their control. Expression of heterologous genes or selected sequences of genes in transgenic plants has typically involved the use of constitutive promoters, i.e., promoters which drive the expression of a product throughout the plant at all times and in most tissues.

Promoters derived from plant sources have been identified and isolated. These promoters have been useful for directing expression of heterologous protein encoding polynucleotide sequences in transformed plant tissues. Plant-derived promoters include the raspberry E4 promoter (U.S. Pat. No. 6,054,635), the apple MADS2 promoter (U.S. Pat. No. 6,392, 122), the melon ACC oxidase promoter, the melon drupe-specific (DRU) promoter, the hybrid promoter of Fuji apple thiamine synthase and melon actin (U.S. Pat. No. 6,392,122), the hybrid promoter of banana thioredoxin-like gene and melon actin gene (U.S. Pat. No. 6,642,438), the promoter of the banana thioredoxin-like gene (U.S. Pat. No. 6,642,438), the melon actin (mACTIN) promoter (U.S. Pat. No. 6,642, 438), and the hybrid promoter from tomato E8 and E4 genes (U.S. Pat. No. 6,118,049).

Transgenic angiosperm plants and the promoters used for these studies have been widely reported. However, there are few reports about the functionality of viral, prokaryote, or angiosperm-derived promoters in gymnosperm tissue. Promoters that are functional in the gymnosperm *Taxus media* (yew) have not been reported. Promoter sequences that are active in *Taxus media* would be useful, for example, for expressing paclitaxel biosynthetic pathway genes to enhance paclitaxel/taxanes biosynthesis.

Some inducible angiosperm-derived promoters have been identified that are functional in white spruce (*Picea glauca*) (Ellis et al., *Plant Mol Biol.* 17(1):19-27, 1991). The CaMV 35S promoter was also used to successfully generate transgenic gymnosperms (Id.). Other promoters that are functional in gymnosperms are reviewed by Tang and Newton (*Plant Cell Rep* 22:1-15, 2003). They include the promoters from nopaline synthase (*Agrobacterium*), Ubi-1(*Zea mays*), cdc2a (*A. thaliana*), sam-1 (*A. thaliana*), HRGPnt3 (*Nicotiana tabacum*), RSI-1 (*Lycopersicon esculentum*), tCUP (*Nicotiana tabacum*) and a putative promoter from an O-methyltransferase of *Pinus radiata*. Forward et al. (*Planta.* 215(4): 569-76, 2002; Epub Apr. 19, 2002) identified and isolated a promoter from Douglas Fir. The luminol binding protein Prn-BiP drove reporter gene expression in Douglas Fir embryos, as well as in *Arabidopsis* (Forward et al., *Planta.* 215(4):569-76, 2002; Epub Apr. 19, 2002). A strong constitutive promoter was isolated from *Pinus radiata* by Perera et al. (*Plant & Animal Genome VIII Conference*, San Diego, Calif. Jan. 9-12, 2000). The promoter from the highly expressed ubiquitin gene yielded reporter gene expression comparable to the 35S promoter (Id.).

Promoters have also been isolated from various organisms. Promoters that are derived from viral genes are useful for expressing genes in plants. Examples of such viral genes which have been identified and isolated include those found in the caulimovirus family of viruses such as Cauliflower Mosaic Virus (CaMV) 35S (Balazs et al., *Gene* 19 (3):239-249, 1982; Guilley et al., *Cell* 30(3):763-773, 1982; Odell et al., *Nature* 313:810-812, 1985; Odell et al., *J. Cell Biochem.* (Suppl. 11B):60, 1987; Odell et al., *Plant Mol Biol* 10(3):263-272, 1988; Tommerup et al., *Eur. Congr. Biotechnol.* 5:916-918, 1990) and CaMV 19S promoters (U.S. Pat. No. 5,352, 605), the Figwort Mosaic Virus (FMV) (U.S. Pat. No. 5,378, 619) promoter, and the Cassava Vein Mosaic Virus (CsVMV) promoter (Verdaguer et al., *Plant Mol Biol.* 37:1055-1067, 1998). *Agrobacterium*-derived promoters have been identified and isolated that are useful for regulating gene expression in plants. Such promoters include those derived from *Agrobacterium* T-DNA opine synthase genes, and include the nopaline synthase (nos) promoter (U.S. Pat. No. 5,034,322), the octopine synthase (ocs) promoter (Leisner & Gelvin, *Proc. Natl. Acad. Sci. USA* 85 (8):2553-2557, 1988) and mannopine synthase (mas) promoter (Leung et al., *Mol Gen Genet.* 230(3):463-474, 1991).

Transformation of various plant species via particle bombardment has demonstrated that DNA can be inserted into any tissue that is impacted by the particle (Bommineni et al., *Plant Cell Rep* 13:17-23, 1993). Tang and Newton (*Plant Cell Rep* 22:1-15, 2003) reviewed biolistic transformation of various gymnosperms including Pine, Larch, and Spruce. Reporter gene expression was transient for most of these biolistic studies. The particle bombardment assay is highly valuable for determining the relative strength of promoters and the competency of various plant tissues for transformation.

While the following promoters have all reported activity in angiosperm tissue, none of them have reports of activity in *Taxus* tissue. The CsVMV promoter was known to direct strong constitutive expression of transgenes in angiosperm tissue (Verdaguer et al., *Plant Mol Biol.* 37:1055-1067, 1998). The mannopine synthase promoter (MAS1') was isolated from *Agrobacterium tumefaciens* has previously shown activity in tobacco, bean, potato and *Arabidopsis* plants (Garcia-Guevara et al., *Mol Gen Genet.* 262 (4-5): 608-617, 1999). The lettuce A7 promoter and Cherry 29 promoter were both isolated by 5'-RACE from lettuce and cherry tissue respectively. These promoters have, until now, unreported activity in *Taxus* tissue. The E8-E4 hybrid promoter (U.S. Pat. No. 6,118,049) is composed of polynucleotide segments derived from the tomato E8 and tomato E4 genes. DNA constructs containing the E8-E4 hybrid promoter operably linked to a SAMase gene were effective in conferring a delayed ripening phenotype to transformed fruit (U.S. Pat. No. 6,118,049). The melon actin promoter sequence was isolated from *Cucumis melo* tissue. When operably linked to the GUS gene this promoter showed GUS activity in banana, onion and garlic (U.S. Pat. No. 6,642,438). In the same report, the thioredoxin-like gene (TRX) promoter isolated from banana showed activity in onion, garlic and banana tissues. When the TRX promoter was fused to the melon actin promoter in a GUS functional assay, the TRX-mACTIN hybrid promoter likewise showed strong promoter activity.

Two promoters were isolated from "Fuji" apple tissue by 5'-RACE (U.S. Pat. No. 6,392,122). In this report, the thiamine synthase promoter (Thi 1) and the MADS2 promoter were translationally fused with GUS. GUS activity was confirmed in apple, peach and pear at all stages of ripening from the immature ovary stage to fully mature, ripe fruit. In addition, a promoter consisting of the Thi-1.3 promoter nucleotides and the melon actin promoter described above were operably fused to the GUS gene and similarly showed strong promoter activity in apple, peach and pear tissues that were tested (U.S. Pat. No. 6,392,122). A nucleotide sequence was synthesized by annealing multiple oligonucleotides together to comprise a full-length polynucleotide sequence of 377 bp. This synthetic promoter corresponded to position 687 to 1064 of the Soybean chlorotic mottle virus complete genomic sequence (Hasegawa et al., Nucleic Acids Res. 17 (23), 9993-10013, 1989). This promoter, like the cherry 29 and lettuce A7 promoter has, as yet, unreported activity in *Taxus* tissue. The raspberry E4 (RE4) promoter is operably linked, in a native raspberry genome, to the coding region of a raspberry E4 gene. The RE4 gene promoter is capable of regulating moderate level of constitutive expression of a heterologous plant gene (U.S. Pat. No. 6,054,635). The DRU and cmAco 1 promoters were isolated from *Cucumis melo* (WO 01/71013). Both promoters were found to have activity that was fruit-specific and ripening associated. The PRU promoter sequence was identified from putative cherry (*Prunus avium*) ortholog to the almond (*Prunus amygdalus*) prunin gene (US Appl. No. 20040064854). PRU promoter activity was assayed by comparing leaf- and seed-oil composition in fad2-1 mutant plants to that of mutant plants transformed with FAD2 cDNA under the control of a PRU promoter or a strong constitutive promoter. Results of PRU-driven expression in seeds (high complementation) versus leaves (absence of complementation), and the promoters' successful complementation of the seed phenotype of fad2-1 mutants (especially as compared to the CsVMV promoter) directly supported the utility of PRU promoters in controlling seed-directed gene expression in a variety of dicot plants, including oilseeds (US Appl. No. 20040064854).

Examples 5-9 (below) describe examination of the activity of the above promoters in *Taxus media*. Using particle bombardment delivery system, promoter activity was assayed with GUS reporter coding nucleotide sequence operably linked to each of the promoters. The promoters identified herein can be useful for directing expression of heterologous protein coding polynucleotide sequences in transgenic *Taxus* plant tissues.

V. Transgenic Cell Lines, and Representative Uses Thereof

With the provision herein of methods for transforming plant cells, including *Taxus* cells, and promoters effective for expression of active heterologous proteins in such transformed cells, methods of producing recombinant compounds, such as taxanes, through expression in transgenic plant cells are now provided.

The transformation methods described herein can be used to produce transgenic plant cells transformed with nearly any expression cassette, or set of expression cassettes. By way of example, the following discussion focuses on *Taxus* cells which have been made transgenic using a transformation method described herein. For exemplary discussion, the heterologous gene(s) used for transformation will be selected from nucleic acids that encode enzymes in a paclitaxel biosynthetic pathway. It will be understood by one of ordinary skill that other plants, and other transgenes, can be used in the described methods.

To generate a transgenic *Taxus* cell that expresses an enzyme (or set of two or more enzymes) from a paclitaxel biosynthesis pathway, a recombinant nucleic acid molecule is generated using known techniques, which molecule includes a promoter sequence operably linked to a nucleic acid molecule encoding the desired enzyme. Those of ordinary skill will be familiar with techniques for producing such recombinant nucleic acid molecules, including for instance expression cassettes and specifically integration vectors. Representative examples of such constructs are described herein. One or more such recombinant nucleic acid molecule is then transformed into the *Taxus* cell using a method provided herein. In particular examples, the transformed cell is an isolated cell, such as a cell line.

In additional examples, methods for increasing taxane yield in a transgenic cell (such as a *Taxus* cell, including, by way of example, a *Taxus* cell line) further involve introducing one or more additional nucleic acid molecules into the cell, such as for instance additional nucleic acid molecule(s) that encode enzymes involved in paclitaxel biosynthesis, or synthesis of a specific taxane.

In certain preferred embodiments, one or more high-taxane production plant cell lines are identified and isolated, which can then be used to efficiently and effectively produce taxane(s) in cell culture. By way of example, any measurable increase in the production of a desirable taxane (or more than one) may indicate a beneficial transgenic *Taxus* cell line. In other instances one or more undesirable taxanes can be reduced or eliminated such that the purity of desirable taxanes increases. Such a cell line can be identified by assaying the production of (one or more) taxanes, for instance the methods described in Example 14. Other methods to detect, measure and quantify taxanes are known. In particular embodiments, taxane production in a transgenic cell line made using the methods described will be at least 5% above the level produced by a non-transgenic cell line from the same or equivalent origin, or some other standard. In other embodiments, production of at least one (or more) desirable taxane will be at least 20% higher, 30% higher, 50% higher, and so forth compared to the reference (non-transgenic) cell (or tissue). Even higher yield cells (or cell lines, or tissues, and so forth) will produce 75% more, 90% more, or 100% more. Particularly preferred cells (cell lines, and so forth) may produce more than twice as much taxane(s) as a reference source, for instance three times as much, four times as much, or even more. For cells and cell lines in which the level of an undesirable taxane is reduced, the reduction will be at least 20% lower, 30% lower, 50% lower, and so forth compared to the reference (non-transgenic) cell (or tissue), down to as little as negligible levels of the taxane(s) that are not desired in said cell (or cell line or tissue).

By way of example, methods for producing various products from plant cell cultures, including transgenic cell cultures, are described in U.S. Pat. No. 6,331,416; U.S. Pat. No. 6,288,302; Roberts & Shuler, *Curr. Op. Biotech.,* 8:154-159, 1997; and Furuya et al., *Phytochemistry* 26(10): 2741-2747, 1987. Additional methods will be known to those of ordinary skill.

In addition, methods developed for production and harvesting of taxanes from non-engineered cells can be adapted for production and harvesting from transgenic *Taxus* cells made using the methods provided herein. See, for instance, Zhong (*J. Biosci. Bioeng.* 94:591-599, 2002), Gibson et al., In *Taxol: Science and Application*, Stuffness (ed.) pp. 71-95. Boca Raton, N.Y.: CRC Press, 1995), and Takeya, (In *Taxus*, Itokawa and Lee (eds). Taylor and Francis Group, London and New York. Pp 134-150, 2003) which describe various methods of plant cell culture for production of taxanes. Methods are also described in Dong & Zhong (*Enz. Microb. Tech.,* 31:116-121, 2002), Tabata (*Adv. Biochem. Eng Biotechnol,* 87:1-23, 2004), Bincat et al. (*Biotechnol Prog.,* 18(6): 1149-1156, 2002), and Wu et al. (*Biochem. Eng. J.,* 5:137-142, 2000). Methods in the mentioned references are provided as representative examples of methods in publications that will be known to those of skill in the art.

Further aspects of the present invention will become clear from the examples described below.

Example 1

Development of *Agrobacterium tumefaciens* Suspensions for Transformation

Figure 1B:
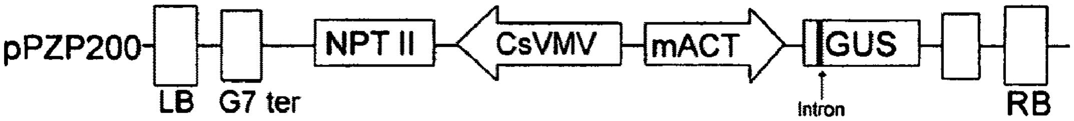

*Agrobacterium tumefaciens* strain EHA101 or GV3101 pMP90RK containing plasmid pAG4015 or pAG4017 were used. Plasmid pAG4015 contained antibiotic selection marker gene nptII and Gus under the transcriptional control of CsVMV and melon actin promoters respectively. The promoter:gene fusions are located between left and right borders. In the case of pAG4017, in addition to the gene elements of pAG4015 there is an intron sequence between the melon actin promoter and the Gus coding sequence. The intron is a 189 bp sequence from potato light-inducible tissue-specific ST-LS1 gene (Accession # X04753) (FIG. 1).

Single, well developed colonies from bacterial plates were cultured on MGL liquid medium containing antibiotics kanamycin (0-50 mg/l), spectinomycin (25 mg/l) and acetosyringone 100 µM. The cultures were agitated on a shaker at 100 rpm at 24° C. for 16 hours or 48 hours for EHA101 and GV3101 pMP90RK respectively.

Example 2

Preparation of Plant Material

Stem twigs about 6-8 inches in length were collected from University of Portland, Oreg. These were sterilized using bleach, ethanol, liquid soap and PPM as described below.

Twigs were cut into 3-4 inch segments with scalpel or scissors and scrubbed with soap and water, using a toothbrush. After rinsing with water twigs were transferred to glass beaker containing soap water and kept on stirrer for 30 minutes followed by keeping under running tap water for 30 minutes. Twigs were then taken to sterile hood, rinsed in ethanol and submerged in 30% bleach with TWEEN™ detergent. After 20 minutes of soaking, the explants were rinsed four times with sterile water while the third rinse included PPM (Plant Preservative Mixture, PhytoTechnology Laboratories, Shawnee Mission, Kans.) at 5 ml/l. Using sterile forceps, twigs were transferred to Petri plate. The needles, stem and bark peel explants were isolated for culture. The needles were cut transversely into 3-4 mm segments while the stem pieces were cut into 5-6 mm pieces with or without scoring the surface with a scalpel blade. Bark peel explants were prepared by carefully peeling off the bark peel away from the stem. The bark peel was then cut transversely into 5-6 mm segments.

Example 3

Generation of Transgenic Calli

Co-Cultivation of Explants with *Agrobacterium tumefaciens*

Needle, stem and bark peel explants were inoculated in (a) a mixture of MGL and liquid co-cultivation medium (serves as a control treatment) and (b) a mixture of *Agrobacterium* suspension at $5\times10^8$ cells/ml density and liquid co-cultivation medium. After 90 minutes of incubation, the explants were scooped into 125 ml flasks with liquid co-cultivation medium and agitated at 80-100 rpm in dark. After one day of liquid co-cultivation the medium was decanted, explants were rinsed with liquid co-cultivation medium once or twice depending on the cloudiness resulting from bacterial growth. Explants were then plated on solid co-cultivation medium with the cut surface in contact with the medium. The total co-cultivation period for *Taxus* explants was three days.

Explants on Selection

The explants on co-cultivation medium were gathered into 125 ml flasks and rinsed with rinsing medium. Depending on the extent of *Agrobacterium* contamination, explants were rinsed 1-3 times or also placed on shaker for brief periods (1-2 hours) of agitation at 100 rpm. After the explants were thoroughly rinsed off, they were blotted and plated on medium containing antibiotic kanamycin/geneticin. The level of kanamycin and geneticin employed vary from 50-350 mg/l and 5-20 mg/l respectively at different stages of explant growth. The responses of the explants were observed biweekly followed by transfer to fresh medium. The cultures were incubated in dark at 24° C.

Media Composition

The liquid co-cultivation medium contained B5 or SH salts (Gamborg et al., *Can. J. Biochem.* 46(5):417-421, 1968; Schenk and Hildebrandt, *Can. J. Bot.* 50: 199-204, 1972), NN vitamins (Nitsch and Nitsch, *Science* 163: 85-87, 1969), 2% D-Glucose, 2% Sucrose, 0-1 mg/l 2,4-D (2,4-Dichlorophenoxy acetic acid), 0-4 mg/l NAA (naphthalene acetic acid), 0-1.0 mg/l 2,i-P (dimethyl allyl aminopurine), 0-2 mg/l IAA (indole acetic acid), 100 mg/l ascorbic acid, 400 mg/l L-cysteine, 0-800 mg/l L-glutamine and 100 µM acetosyringone at pH 5.4. The solid co-cultivation medium had the same composition gelled with 1% phytagel. The rinsing medium contained B5 or SH salts (Gamborg et al., *Can. J. Biochem.* 46(5):417-421, 1968; Schenk and Hildebrandt, *Can. J. Bot.* 50: 199-204, 1972), NN vitamins (Nitsch and Nitsch, *Science* 163: 85-87, 1969), 3% sucrose, 1 mg/l 2,4-D, 4 mg/l NAA, 4 mg/l IAA, 1000 mg/l cefotaxime/500 mg/l timentin at pH 5.8. The selection media contained B5 or SH salts (Gamborg et al., *Can. J. Biochem.* 46(5):417-421, 1968; Schenk and Hildebrandt, *Can. J. Bot.* 50: 199-204, 1972), NN vitamins (Nitsch and Nitsch, *Science* 163: 85-87, 1969), 2-3% sucrose with several combinations and levels of plant growth regulators namely NAA, 2,4-D, IAA and 2,i-P supplemented with 500 mg/l cefotaxime/250 mg/l timentin and kanamycin or geneticin at 50-500 mg/l and 5-20 mg/l respectively.

Screening of Transformed Callus

The explants were observed biweekly and transferred to fresh medium with increased selection depending on the growth rate of callus. The callused explants were either directly transferred to solid selection medium or were given a liquid soak for 2-4 hours followed by blotting and plating in order to arrest the growth of untransformed cells. The putatively transformed callus was identified based on fresh cell proliferation on explants growing on medium with selection. Such fresh growth was evidenced only in bark peel explants while the stem and needle tissues gave callus all over the explant which on subsequent transfers turned brown. In case of bark peel explants, while the initial callus turned brown, islands of fresh growth became evident in a period of 3-5 months. A total of five independent transformed calli were recovered from two experiments using *Agrobacterium tumefaciens* strains EHA101 and GV3101 pMP90RK.

Example 4

Validation of Transformation Events

Figure 2:
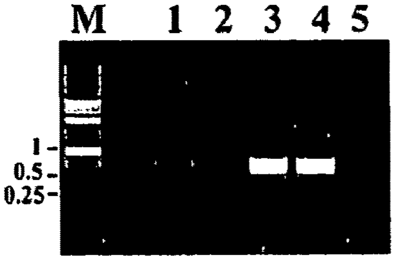
FIGS. 2A-2C illustrate PCR analysis of GUS positive calli confirming integration of GUS gene into *Taxus media* 'Hicksii' genome.
Figure 2:
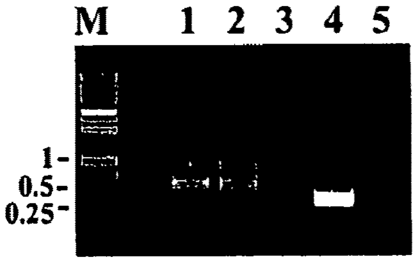
Figure 2:
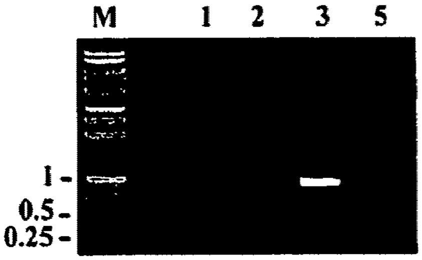

Samples of callus from several explants were subjected to X-Gluc analysis. The control callus and the non-transformed calli remained yellow while the transformed tissue formed the typical blue precipitate resulting from the β-glucuronidase enzyme activity on the X-Gluc substrate. The transformed callus continued to proliferate on selection medium containing 350 mg/l kanamycin while the wild type callus (control) tissue declined in growth with subsequent transfers. After nine months of culture transformed tissue was retested for X-gluc histochemical assay and found to be positive. The genomic integration of the transgenes nptII and gus was confirmed by PCR using mACTIN promoter and GUS-specific primer set and/or CsVMV promoter and NPT II-specific primer set combination (FIGS. 2A and 2C). Endogenous TDS gene sequence was used as a check for genomic DNA quality (FIG. 2B).

Extraction of *Taxus media* 'Hicksii; Genomic DNA

*Taxes media* 'Hicksii' genomic DNA was prepared using Nucleon PHYTOPURE™ Plant DNA Extraction kit protocol (Amersham LIFE SCIENCE). Briefly, 12 to 50 mg of *Taxus media* 'Hicksii' callus tissue was ground into fine powder with liquid nitrogen, transferred into 1.5 ml Eppendorf tube and mixed with 600 μl reagent 1. After mixing well with reagent 1, 200 μl reagent 2 was added and incubated at 65 C for 10 minutes with gentle shaking. Then the sample was placed on ice for 20 minutes and added 500 μl cold chloroform and 100 μL of Nucleon PHYTOPURE™ DNA extraction resin suspension. The sample was incubated on a tilt shaker at room temperature for 10 minutes. The sample was centrifuged at 4400 rpm for 10 minutes and transferred upper DNA containing phase above the brown resin layer, into a fresh Eppendorf tube. The genomic DNA was precipitated with an equal volume of cold isopropanol and was pelleted by centrifugation at 10000 rpm for 5 minutes. The DNA was washed with 70% ethanol, air-dried and dissolved in TE (10 mM Tris-HCl, 0.1 mM EDTA). The quantity of genomic DNA was estimated spectrophotometrically and used in polymerase chain reaction assay.

Polymerase Chain Reaction Assay:

To test the integration of T-DNA region, mACTIN promoter- and GUS gene-specific primer set (Actin F1 primer-TGCTGCTTTCGTCTCTCA (SEQ ID NO: 1); GUS5-reverse primer-GACTTCGCGCTGATACC (SEQ ID NO: 2)) or CsVMV promoter- and NPT II gene-specific primer set (CsVMVp3F forward primer-GTGTAAGC-TATTTTCTTTGAAGTA (SEQ ID NO: 3) and Npt3 reverse primer: GCCAACGCTATGTCCTGA (SEQ. ID NO: 4)) were used. To test the quality of genomic DNA in PCR analysis, either conserved *Taxus* endogenous actin gene specific primer set (forward primer-GTGACAATGGAACTG-GAATGG (SEQ ID NO: 5) and reverse primer-AGACG-GAGGATAGCGTGAGG (SEQ ID NO: 6)) (Kai et al., *J. Biosci.* 29:101-109, 2004) or endogenous *Taxus brevifolia* taxadiene synthase gene-specific primer set (Wildung and Croteau, 1996) (TDS_420F forward primer-AGATAT-CAGTCCGTCTGC (SEQ ID NO: 7) and TDS_784R reverse primer CGTAAGGAAGATTGATCC (SEQ ID NO: 8)) were used.

PCR analysis was performed with genomic DNA isolated from transgenic and wild-type callus tissues. Primers each at 0.5 μM concentration, 250 μM of each dNTPs, one unit of taq polymerase in a 20 μl reaction volume in a thermal cycler machine were used. The PCR cycle conditions for mACTIN-GUS primer set and actin gene-specific primer set were as follow: initial denaturation at 94° C. for 2 minutes; 30 cycles at 94° C. for 30 seconds; 48° C. for 30 seconds and 72° C. for 1 minute and a final extension at 72° C. for 10 minutes. The PCR cycle conditions for CsVMV-NPT II and taxadiene synthase gene-specific were as follow: initial denaturation at 95° C. for 2 minutes; 30 cycles at 95° C. for 1 minute; 51° C. for 1 minute and 72° C. for 1.5 minute and a final extension at 72° C. for 10 minutes. The resultant PCR conditions were analyzed through agarose gel electrophoresis (Sambrook et al., *Molecular cloning—A laboratory manual*. Cold Spring Harbor Laboratory, New York, 1989).

FIG. 2A shows an expected PCR amplicon (~740 bp) with CsVMVp3F and Npt3 reverse primer set in transgenic callus (lane 1) and two PCR positive controls (lanes 3 and 4). Endogenous taxadiene synthase gene-specific primer set was used to verify the quality of genomic DNA (FIG. 2B). As expected, both transgenic and wild-type *Taxus* produced endogenous taxadiene synthase gene-specific PCR amplicon (lanes 1 and 2) that is bigger than taxadiene synthase cDNA template (~365 bp) (lane 4). FIG. 2C, shows the expected PCR amplicon of about 1 kb with mACTIN and GUS-specific primer set. As a positive control in PCR, pAG4015 binary vector plasmid DNA was used as a template and the same primer set amplified about 1 kb product (FIG. 2C, lane 3). Wild-type *Taxus media* 'Hicksii' callus and PCR control with out template did not amplify any PCR product with mACT and GUS-specific primer set FIG. 2C, lane 2 and lane 5.

Example 5

General Materials and Methods Related to Promoter Analysis

Biological reagents were procured from the following vendors: Plasmid preparation kit from Qiagen, Valencia, Calif.; Restriction endonucleases from New England Bioloabs, Beverly, Mass.; Reagents employed in the particle bombardment include BioRad Biolistic PDS-1000/He system (BioRad Laboratories, Hercules, Calif., USA); 1.5-3.0 μm gold particles (Aldrich, Milwaukee, Wis., USA); stop screens of 0.685 mesh and macrocarriers (Rumsey-Looms, Freeville, N.Y.); rupture disks (BioRad Laboratories, Hercules, Calif.) and X-Gluc: 5-Bromo-4-chloro-3-indoyl β-D-glucuronide cyclohexylamine salt (Rose Scientific, Edmonton, Alberta, Canada).

Promoter constructs were prepared using standard molecular techniques (Sambrook et al., *Molecular Cloning: A Laboratory Manual* ($2^{nd}$), Cold Spring Harbor Press, Plainview, N.Y., 1989). Qiagen plasmid preparation manufacturer kit protocol for plasmid DNA preparation and standard molecular procedures were followed for restriction digestion, sequencing and plasmid DNA quantification analyses.

Sixteen promoter sequences were analyzed in *Taxus media* 'Hicksii' cell cultures. These promoter sequences were derived from Cassava Vein Mosaic Virus (CsVMV), *Agrobacterium tumefaciens* and various angiosperm plant genes or contain a synthetic promoter sequence. These are:

1) CsVMV;

2) *Agrobacterium tumefaciens* mannopine synthase gene 1' (MAS1');

3) lettuce A7;

4) CH29 (thaumatin-like gene);

5) hybrid promoter from tomato E8 and E4 genes;

6) melon actin (mACTIN) gene;

7) banana thioredoxin-like (TRX) gene;

8) hybrid promoter of banana thioredoxin-like gene and melon ACT genes;

9) Fuji apple thiamine synthase (Thi 1) gene;

10) hybrid promoter of Fuji apple thiamine synthase and melon ACT genes (Thi 1.3:mACTIN);

11) *Cucumis melo* DRU (drupe-specific) gene;

12) *Cucumis melo* ACC oxidase gene;

13) Fuji apple MADS2 gene;

14) raspberry E4 gene homolog (RE4);

15) a fruit-specific cherry Pru gene; and 16) a synthetic promoter.

All the promoter sequences were fused to the 5' end of the GUS reporter coding sequence and nopaline synthase gene terminator sequence was fused to the 3' end of the GUS coding sequence. The GUS coding sequence without any promoter was used as control in transient assays with *Taxus media* 'Hicksii' tissues. The promoter sequences are provided in SEQ ID NO: 9 through 25.

Preparation of Plasmid DNA for Biolistic Transformation: Five μg of Promoter-Gus Fused plasmid DNAs were incubated with 3 mg of gold particles (1.5-3 μm in size and were washed with ethanol and suspended in 50% glycerol v/v), 50 μl of 2.5 M $CaCl_2$ and 0.1 M spermidine in a 125 μl reaction volume. The DNA samples were incubated at room temperature for 15 min with gentle shaking. Followed by incubation, the gold-coated DNA particles were centrifuged at 10,000 rpm for 1 minute at room temperature. The gold-coated DNA particle pellet was washed with 70% ethanol (v/v) and finally dissolved in 50 μl of 100% ethanol. After sonication of prepared DNA-coated gold particles for 30 seconds in a Sonicator, 10 μl was placed on a clean 70% ethanol sterilized macrocarrier disk and used in bombardment assays.

Preparation of *Taxus media* 'Hicksii' plant tissues: Needles were surface sterilized using standard procedure. Callus was raised from *Taxus media* needles. Cell suspension cells were obtained from Washington State University, Pullman, Wash. Young needles, 30-day-old callus and 7 to 14-day-old cell suspensions were pre-incubated on ½ MS-agar plate without vitamins and containing mannitol and sorbitol each at 500 mM concentration for 4 h at room temperature. These tissues were bombarded with BioRad Biolistic PDS-1000/He system using various plasmids at 9 cm flight path distance and 1350 PSI disks.

Post-bombardment conditions: The bombardment tissue was sealed and placed in dark for 12 h on the same plate and another 24-36 h on ½ MS-agar plate without vitamins, mannitol and sorbitol. Following incubation, the bombarded tissue was assayed for GUS activity (Jefferson, *Plant Mol Biol Rep.* 5: 387-405, 1987). GUS activity was assayed in a buffer (0.1 M sodium phosphate pH 7.0, 0.5 mM potassium ferricyanide, 0.5 mM potassium ferrocyanide, 10 mM EDTA and 0.1% Triton X-100) containing the GUS substrate X-Gluc for 24-48 h at 37° C. The GUS-associated blue colored spots were cleared by removing X-Gluc solution and cleared with 70% ethanol. The size and intensity of the GUS foci were analyzed under a dissecting microscope. Based on the size, intensity and to a lesser extent number of the GUS-associated blue colored foci, the promoter activity was classified into four categories: strong, medium, low and very low/no activity. For example, if promoter 1 shows high intensity of GUS-associated blue color but showed a lower number of GUS foci compared to promoter 2 that showed low intensity of GUS-associated blue color but a higher number of GUS foci, then promoter 1 is considered a higher activity promoter than promoter 2.

Example 6

CsVMV Viral Promoter is More Active than Angiosperm mACTIN Promoter in Embryo-Derived Cell Suspensions and Stem-Derived Callus Tissues of *Taxus media* 'Hicksii'

Transient biolistic bombardment assay was performed to determine relative promoter activity of 16 promoters in *Taxus media* 'Hicksii' cell suspensions. Initially, activity of CsVMV and mACTIN promoters fused to GUS reporter along with a promoterless GUS reporter control has been determined in cell suspension cultures, and callus tissues. As shown in Table 1 and 2, CsVMV showed higher activity than mACTIN promoter in terms of number, size and intensity of GUS-associated blue spots. CsVMV showed three-fold higher number of GUS-associated blue spots and stronger intensity than mACTIN promoter driving GUS-associated blue spots in cell suspensions (Table 1 and Table 2). Further, CsVMV promoter is active in leaf or needle tissue of *Taxus baccata* (Table 3).

TABLE 1

Transient GUS assay in *Taxus media* 'Hicksii' cell suspension cultures

| Promoter | Promoter ID | Number of GUS foci | Activity Group |
|---|---|---|---|
| CsVMV | pAG153 | 150 | High |
| mACTIN | pAG167 | 50 | Low |
| Promoterless control | pAG147 | 0 | No |

TABLE 2

Transient GUS assay in callus derived from stem tissue of *Taxus media* 'Hicksii'

| Promoter | Promoter ID | Number of GUS foci |
|---|---|---|
| CsVMV | pAG153 | 35 |
| mACTIN | pAG167 | 11 |
| Promoterless control | pAG147 | 0 |

TABLE 3

Transient GUS assay in needles of *Taxus baccata*

| Promoter | Promoter ID | Number of GUS foci |
|---|---|---|
| CsVMV | pAG153 | 18 |
| Promoterless control | pAG147 | 0 |

Example 7

Evaluation of *Agrobacterium tumefaciens* MAS1'Gene Promoter And Other Angiosperm Gene Promoter Activity in Cell Suspension Cultures of *Taxus media* 'Hicksii'

The *Agrobacterium* MAS1'-gene promoter and tomato E8-E4 hybrid promoter showed medium activity compared to viral CsVMV promoter (Table 4). Both MAS1' and E8-E4 promoters showed about 4-fold lower number of GUS-associated blue spots (Table 4), but showed medium intensity of GUS-associated blue spots compared to CsVMV promoter activity. Although the hybrid E8-E4 promoter activated GUS gene expression and showed similar number of GUS foci, the intensity of GUS-associated blue spots is less compared to MAS1' and CsVMV. Other angiosperm promoters such as banana TRX and melon actin hybrid TRX-mACTIN promoter and melon Aco promoters showed 9-fold less number of GUS-associated blue spots compared to CsVMV promoter (Table 4) and also showed very weak GUS foci. RE4 showed very few GUS foci and Pru I did not show any activity in cell suspension cultures of gymnosperm *Taxus media* 'Hicksii (Table 4). Promoterless GUS reporter construct was used as control in GUS reporter assay and did not show any activity.

TABLE 4

| Transient GUS assay in *Taxus media* 'Hicksii' cell suspension cultures | | | |
|---|---|---|---|
| Promoter | Promoter ID | Number of GUS foci | Activity Group |
| CsVMV | pAG153 | 665 | High |
| MAS1' | pAG740 | 159 | Medium |
| E8-E4 | pAG134M | 172 | low |
| TRX-mACTIN | pAG749 | 59 | Low |
| CmAco | pAG152M | 69 | Low |
| RE4 | pAG138M | 11 | Low/very low |
| Pru | pAG4021 | 0 | No |
| Promoterless control | pAG147 | 0 | No |

Example 8

Evaluation of Different Angiosperm Gene Promoter Activities in Cell Suspension Cultures of Gymnosperm *Taxus media* 'Hicksii'

The CH29 promoter and lettuce A7 promoter showed 128% higher and 59% lower number of GUS-associated blue spots compared to CsVMV reporter activity, respectively. Although CH29 and A7 promoters differ in number of GUS-associated blue spots, the intensity of color is similar (Table 5). TRX, Thi 1.3-mACTIN hybrid promoter, Thi 1 and DRU promoter showed low activity in terms of intensity and number of GUS-associated blue spots (Table 5). MADS2 and a synthetic promoter showed very weak activity in terms of number as well as intensity of color (Table 5).

TABLE 5

| Transient GUS assay in *Taxus media* 'Hicksii' cell suspension cultures | | | |
|---|---|---|---|
| Promoter | Promoter ID | Number of GUS foci | Activity Group |
| CsVMV | pAG153 | 1015 | High |
| CH29 | pAG133 | 1308 | Medium |
| A7 | pAG742 | 598 | Medium |
| TRX | pAG159 | 447 | Low |
| Thi 1.3-mACTIN | pAG752 | 258 | Low |
| Thi 1 | pAG162a | 360 | Low |
| DRU | pAG154 | 231 | Low |
| MADS2 | pAG168 | 53 | Low/very low |
| Synthetic promoter | pAG139C | 6 | Very low |
| Promoterless control | pAG147 | 0 | No |

Example 9

Tested Promoter Activities were Classified into Four Categories: High, Medium, Low and Very Low/No Activity Based on relative intensity and size of various promoter-driven GUS-associated blue spots in embryo-derived cell suspension cultures of *Taxus media* 'Hicksii', the tested promoters were classified into four different categories. The viral CsVMV promoter showed highest activity of all the promoters tested (Table 6). *Agrobacterium tumefaciens* MAS1' gene promoter and two angiosperm promoters such as lettuce A7 and CH29 showed medium activity compared to viral CsVMV promoter. Eight angiosperm promoters including hybrid tomato E8-E4, mACTIN, TRX, TRX-mACTIN, Thi 1, Thi 1.3:mACTIN, DRU and CmAco fell into low activity class of promoters. Two angiosperm promoters MADS2 and RE4 showed low activity and PRU and a synthetic promoter either showed very low activity or were unable to drive expression of GUS reporter gene in *Taxus media* 'Hicksii' (Table 6). As shown in Tables 1-5, the CsVMV promoter has the strongest activity in *Taxus media* 'Hicksii' cell suspensions. Promoterless GUS reporter construct was used as control in determining GUS reporter activity.

Fifteen promoters that include CsVMV, MAS1', A7, CH29, E8-E4, mACTIN, TRX, TRX-mACTIN, Thi 1, Thi 1.3-mACTIN, DRU, CmAco, MADS2, RE4 and a synthetic promoter are able to activate heterologous GUS reporter gene expression in cell suspension cultures of *Taxus media* 'Hicksii'. These promoters can be fused to any protein coding gene and can be expressed in any tissues of *Taxus* species. The protein coding genes include, but not limited to, are paclitaxel biosynthetic pathway genes or its related branch or intermediate pathway genes or any secondary metabolite product biosynthesis in *Taxus* species.

TABLE 6

| Classification of promoter activity in *Taxus media* 'Hicksii' cell suspensions, callus and needles[1]. | | | |
|---|---|---|---|
| Promoter | Plasmid code | Activity[2] | Tested *Taxus media* 'Hicksii' tissues |
| 1) CsVMV | pAG153 | Strong | Cell suspensions, callus and needles[3] |
| 2) MAS1' | pAG740 | Moderate | Cell suspensions |
| 3) A7 | pAG742 | Moderate | Cell suspensions |
| 4) CH29 | pAG133 | Moderate | Cell Suspensions |
| 5) E8-E4 | pAG134M | Low | Cell suspensions |
| 6) mACTIN | pAG167 | Low | Cell suspensions, callus |
| 7) TRX | pAG159 | Low | Cell suspensions |
| 8) TRX-mACTIN | pAG749 | Low | Cell suspensions |
| 9) Thi 1 | pAG162a | Low | Cell suspensions |
| 10) Thi 1.3:mACTIN | pAG752 | Low | Cell suspensions |
| 11) DRU | pAG154M | Low | Cell suspensions |
| 12) CmAco | pAG152M | Low | Cell suspensions |
| 13) MADS2 | pAG168 | Very Low | Cell suspensions |
| 14) RE4 | pAG138M | Very Low | Cell suspensions |
| 15) PRU | pAG4021 | No activity | Cell suspensions |
| 16) Synthetic promoter | pAG139C | Low/no activity | Cell suspensions |
| Control | pAG147 | No activity | Cell suspensions, callus, needles |

[1] Promoter activity was based on biolistic particle delivery of equal amounts of plasmid DNA constructs. The chimeric gene constructs contain different promoters that were fused to GUS reporter::NOS terminator. A control plasmid contains GUS reporter fused to NOS terminator without a promoter sequence. In all construct the variability is promoter sequence. Each promoter construct was transiently tested at least three independent experiments.

[2] The promoter activity was based on visual observation of relative comparison of size and intensity of GUS-associated blue color.

[3] *Taxus baccata* needles

Example 10

Preparation of Binary Vectors with Taxadiene Synthase and Cytochrome P450-Dependent Monooxygenase 13-alpha-Hydroxylase Genes for Transformation of *Taxus media* 'Hecksii'

DNA Constructs:

Plant transformation constructs pME4100 and pME4103 were designed for stable expression of Taxadiene synthase (TDS) and the cytochrome P450-dependent monooxygenase 13-alpha-hydroxylase (T13H), respectively. In both constructs, the coding sequences of these genes are under the control of the *Agrobacterium tumefaciens*-derived mannopine synthase (mas1') promoter. The mas1' promoter has been shown to be a useful promoter for GUS gene expression in *Taxus* cells thus it was chosen for expression of TDS and T13H for *Taxus* transformation.

To construct TDS and T13H plant transformation constructs, the intermediate plasmid pME4001 was first synthesized. Plasmid pME4001 includes a pPZP200 backbone with right and left border sequences; Cassava Vein Mosaic Virus (CsVMV) promoter driving neomycin phosphotransferase II (NPTII) expression and the Gene 7 terminator. Plasmid pME4001 was also engineered with a multiple cloning site located immediately downstream of the mas1' promoter, and located immediately upstream of a nopaline synthase terminator. To construct pME4001, a portion of in-house plasmid pAG4012, total length 10,889 basepairs (bp), was excised using restriction enzymes PpuMI (location 6734 bp) and PmlI (location 8589 bp). The digested DNA was run out on a 1% agarose gel and the 1855 bp fragment was purified with a Qiagen gel purification kit. Likewise, a 7260 bp DNA fragment from in-house plasmid pAG4217 (total length 9558 bp) was prepared by a double restriction digestion with enzymes PpuMI (location 2961 bp) and SmaI (location 5259 bp). The 1855 bp DNA fragment from pAG4012 and the 7260 bp DNA fragment from pAG4217 were ligated together to make pME4001. pME4001 was transformed into *E. coli* strain Invαf chemically competent cells. Nucleotide sequencing and restriction digestion confirmed successful cloning of the pME4001 plasmid. Cloning vector pME4001 was used as an intermediate for making plant transformation constructs pME4100 (mas1':TDS) and pME4103 (mas1':T13H).

Plasmid constructs containing the TDS and T13H coding sequences (GenBank accessions U48796.1 and AY056019.1, respectively) were obtained from the lab of Dr. Rod Croteau, Washington State University (Pullman, Wash.). Primers were designed to PCR-amplify the respective genes from the WSU clones. To facilitate cloning the coding sequences of TDS and T13H into plasmid pME4001, a forward primer for PCR-amplification of each gene included a Spe I restriction enzyme recognition sequence and a Kozak sequence. The reverse primers for PCR-amplification of each gene included a Kpn I site. The primer sequences are shown below (Table 7).

TABLE 7

Forward (F3) and Reverse (R3) PCR primers nucleotide sequences for adapter-mediated cloning of T13H and TDS. The Spe I site (underlined) and KpnI site (bold) are shown. The adapter sequences facilitate cloning of the PCR products into the corresponding sites in plasmid pME4001. Primer sequences show Kozak sequence in italics, ATG (start) codon sequence is flanked by single asterisks (*), and stop codons are flanked by double asterisks (**).

| | | |
|---|---|---|
| T13αH_F3 | TCAGGACTAGTGACC*ATG*GATGCCCTTAAGCAATTG | SEQ ID NO: 26 |
| T13αH_R3 | TACGGGGTACC**TTA**AGATCTGGAATAGAGTTTAATGG | SEQ ID NO: 27 |
| TDS_F3 | TCAGGACTAGTGACC*ATG*GCTCAGCTCTCATTTAATG | SEQ ID NO: 28 |
| TDS_R3 | TACGGGGTACC**TCA**TACTTGAATTGGATCAA | SEQ ID NO: 29 |

The TDS and T13H coding sequence were each ligated into the Spe I and the KpnI sites in pME4001. Sticky-ended cloning allowed placement of the TDS and T13H coding sequence including Kozak and start codon sequences immediately downstream of the mas1' promoter in the pME4001 vector. Nucleotide sequencing and restriction digestion confirmed successful cloning of the newly constructed plasmids pME4100 and pME4103. Plasmids were transformed into *E. coli* strain Invαf' to propagate the plasmids. *Agrobacterium tumefaciens* strains EHA101 and GV3101/pMP90RK were transformed with each of the plasmids by electroporation. After confirming the presence of the plasmid in *Agrobacterium*, transformed *Agrobacterium* stocks were used for *Agrobacterium*-mediated transformation of *Taxus media.*

Example 11

Transformation of *Taxus media* 'Hicksii' Using *Agrobacterium tumefaciens* Strain GV3101 pMP90RK Containing Plasmid pME4103 (pPZP200::CsVMV-nptII-G7/Mas1'-T13αH-nosT)

Preparation of *Agrobacterium* Suspension:

*Agrobacterium tumefaciens* strain GV3101 pMP90RK was streaked on MGL plates (Garfinkel and Nester, *J. Bact.* 144: 732-743, 1980) with 100 mg/L spectinomycin, 50 mg/l kanamycin. Plates were incubated at 28° C. in the dark. After 3 days of incubation, well-developed independent single colonies were inoculated into 35 ml of MGL liquid medium containing 50 mg/l spectinomycin, 25 mg/l kanamycin and 100 μM acetosyringone at pH 5.4. Flasks were agitated on a gyratory shaker at 120 rpm and 24° C. The bacterial suspension of density ~$5\times10^8$ cells/ml was used for inoculation of plant tissues. This concentration was achieved by adding the required amount of plant tissue culture medium (referred as 'Li' medium) to the bacterial broth. See composition of 'Li' media (TM00000513) in Table 8.

TABLE 8

Media composition for transformation analyses (Examples 11 and 12)

| 'Li' Medium (TM00000513) |
|---|
| B5 salts |
| NN vitamins |
| D-Glucose 2% |
| Sucrose 2% |
| 2,4-D 1 mg/l |
| NAA 4 mg/l |
| Ascorbic acid 100 mg/l |
| L-Glutamine 800 mg/l (aa)* |
| L-Cysteine 400 mg/l (aa)* |
| Acetosyringone 100 M (aa)* |
| pH 5.4 |

TABLE 8-continued

| Media composition for transformation analyses (Examples 11 and 12) |
|---|
| Positive Plate without Selection (TM00000502) |
| SH salts<br>NN vitamins<br>Sucrose 2%<br>NAA 4 mg/l<br>2,4-D 1 mg/l<br>2,i-P 0.5 mg/l<br>L-Glutamine 800 mg/l (aa)*<br>Timentin 250 mg/l (aa)*<br>pH 5.8<br>Phytagel 0.25% |
| 'S' Medium (TM00000514) |
| B5 salts<br>NN vitamins<br>D-Glucose 2%<br>Sucrose 2%<br>2,4-D 1 mg/l<br>NAA 4 mg/l<br>Ascorbic acid 100 mg/l<br>L-Glutamine 800 mg/l (aa)*<br>L-Cysteine 400 mg/l (aa)*<br>Acetosyringone 100 M (aa)*<br>pH 5.4<br>Phytagel 1% |
| Kanamycin Selection Medium (TM00000506) |
| SH salts<br>NN vitamins<br>Sucrose 2%<br>NAA 4 mg/l<br>2,4-D 1 mg/l<br>2,i-P 0.5 mg/l<br>L-Glutamine 800 mg/l (aa)*<br>Timentin 250 mg/l (aa)*<br>Kanamycin 300 mg/l (aa)*<br>pH 5.8<br>Phytagel 0.25% |
| Geneticin Selection Medium (TM00000516) |
| SH salts<br>NN vitamins<br>Sucrose 2%<br>NAA 4 mg/l<br>2,4-D 1 mg/l<br>2,i-P 0.5 mg/l<br>L-Glutamine 800 mg/l (aa)*<br>Timentin 250 mg/l (aa)*<br>Geneticin 20 mg/l (aa)*<br>pH 5.8<br>Phytagel 0.25% |

*aa - component added to the medium after autoclaving, by Millipore filtration
B5 salts - Gamborg et al., *Cell Res.* 50: 151-158, 1968
SH salts - Schenk and Hildebrandt 1972
2,4-D - 2,4-Dichlorophenoxyacetic acid
2,i-P - 6 gamma gamma dimethyl allyl aminopurine
IAA—Indole acetic acid
NAA—naphthalene acetic acid Preparation of Explant Material:

Twigs of *Taxus media* 'Hicksii' about 6-8" in length were cut from a ~15 year old tree at University of Portland. These were collected in a zip lock bag containing paper towels moistened with de-ionized water. Two hours after collection, the material was sterilized in the laboratory.

Sterilization Protocol

Twigs were cut into 3-4" pieces. The twigs were submerged into 95% ethanol for 10-15 seconds with brisk stirring followed by decanting the alcohol. Twigs were then rinsed under running tap water, submerged into 30% bleach and 10 drops of TWEEN™ 20 detergent per liter for 10 minutes.

Twigs were then stripped off their needles by hand. Stem twigs without needles were then scrubbed with bacterial liquid soap using toothbrush and then placed in a beaker with bacterial liquid soap solution and stirred on the magnetic stirrer for 30 minutes at speed 9-10 (to provide thorough access of the twigs to soapy water). The beakers were covered with cheese cloth, secured by a rubber band around the mouth and rinsed under running tap water. After 30 minutes the cheese cloth was removed and water was decanted. The beaker with the twigs was brought into the laminar hood and from this point onwards, sterile techniques were used.

Using a long forceps twigs were placed in sterile 1 L flasks, covered with 95% ethanol and briskly shaken for 10-15 seconds followed by decanting the alcohol. The twigs were submerged in 20% bleach with 10 drops of TWEEN™ 20 detergent per liter for 15 minutes, agitating every 5 minutes.

The bleach was decanted and twigs rinsed with sterile water four times—the first, a quick rinse and decanting, second, cover with sterile water soaking for 15 minutes with intermittent agitation before decanting. Third rinse: soaked in sterile water containing 5 ml/L PPM for 1 hour before decanting. Final (fourth) rinse was with brisk shaking and immediate decanting The twigs were placed on sterile Petri plates and stored overnight in the laminar hood. Next day, the bark was peeled off using a sharp scalpel blade (size #10) taking care to include just the cambial tissue and not go deep to avoid the pith tissue.

Incubation and Co-cultivation of Bark Peel Explants with *Agrobacterium*

The excised bark peels were cut into 8-10 mm pieces and incubated in the *Agrobacterium* suspension mixture. A total of 2775 explants were treated with *Agrobacterium*. As control explants, 120 bark peel segments were placed in a mixture of MGL (Garfinkel and Nester, *J. Bact.* 144: 732-743, 1980) and 'Li' liquid medium (1:3 ratio of MGL and 'Li' medium). After 90 minutes of incubation the control and *Agrobacterium*-treated explants were scooped and transferred to 30-35 ml 'Li' liquid medium in 125 ml flasks and kept on gyratory shaker at 80-100 rpm for 16-18 hours in the dark. Next day the solution was decanted and rinsed once with the Li medium, blotted on sterile blotting sheet and placed on 'S' medium for two days. The cut portion of the bark peel was in contact with the medium. Composition of 'S' medium (TM00000514) is provided in Table 8.

Culture of Bark Peel Explants on Selection Medium

After three days of co-cultivation (one day liquid and two days solid medium) the bark peel explants were directly transferred to callus induction medium as no sign of *Agrobacterium* overgrowth was noticed. The cut surface of the bark peel was placed away from the surface of the medium. The callus induction medium contained the selection agent kanamycin at 300 mg/l (TM00000506) or geneticin at 20 mg/l (TM00000516). The control explants, i.e. the explants not treated with *Agrobacterium* were plated on medium with no selection (which served as positive control) and also with selection antibiotic (which serves as the negative control) (TM00000502). The *Agrobacterium* treated explants were divided between the two selection media, i.e., kanamycin or geneticin.

Cultures were observed periodically and transferred to fresh medium every two to three weeks. If the callus growth was profuse, the callus was isolated from the explant and placed along side the original explant during transfer.

Results

The explants started showing signs of callus formation at the end of three weeks. All explants were periodically transferred to fresh medium. Some of the explants on subsequent transfer failed to continue callus growth. At the end of ~4 months after initiation of the experiment, the explants were scored on the basis of presence or absence of noticeable callus (i.e. callus that can be seen without the use of a microscope). From a total of 2775 explants, 859 explants had callus and 80 of these were sampled for transgene analysis by PCR.

Example 12

Transformation of *Taxus media* 'Hicksii' Using *Agrobacterium tumefaciens* Strain GV3101 pMP90RK Containing Plasmid pME4100 (pPZP200::CsVMV-nptII-G7/Mas1'-TDS-nosT)

Methods and Materials:

*Agrobacterium* suspension was prepared as in Example 11.

*Taxus* twigs were collected from University of Portland. The material was sterilized and bark peels were excised as in Example 11.

Bark peel explants were conditioned before subjecting them to *Agrobacterium* treatment. The bark peels cut into 8-10 mm pieces were cultured on medium TM00000308 (SH salts, NN vitamins, 3% Sucrose, 6 mg/l NAA, 1 mg/l 2,4-D, 0.5 mg/l 2,i-P, 800 mg/l L-glutamine (aa—after autoclaving) pH 5.8, 0.25% Phytagel). Bark peels were placed with the cut surface away from the medium and incubated in darkness for 6 days. These explants had signs of swelling at the time of treatment with *Agrobacterium*

Incubation and co-cultivation of conditioned bark peel explants with *Agrobacterium* were as in Example 11. Culture of bark peel explants was as in Example 11 until the first observation after two weeks of plating on selection media.

The callused explants from *Agrobacterium*-treatment were given a liquid soak for one hour. The explants with callus on kanamycin selection medium were soaked in TM0000505 (SH salts, NN vitamins, 2% Sucrose, 1 mg/l 2,4-D, 4 mg/l NAA, 0.5 mg/l 2,i-P, 800 mg/l L-Glutamine (aa), 200 mg/l kanamycin (aa), 250 mg/l timentin (aa)). The explants with callus on geneticin selection medium were soaked in TM00000530 (SH salts, NN vitamins, 2% Sucrose, 1 mg/l 2,4-D, 4 mg/l NAA, 0.5 mg/l 2,i-P, 800 mg/l L-Glutamine (aa), 12 mg/l geneticin (aa), 250 mg/l timentin (aa)). After soaking the explants with callus were carefully blotted on sterile blotting paper and plated on respective selection media—TM00000506/TM00000516.

Observations were then carried out periodically at the end of 2-3 weeks followed by transfer to fresh media. Depending on the proliferation rate of the callus, individual events were transferred to separate culture plates.

Results

All of the explants showed discernible callus by the end of two weeks. All received the liquid bath/soak as explained above, followed by blotting and plating on fresh selection media. From a total of 522 *Agrobacterium* treated explants, 203 showed callus at the end of 8 weeks. After further transfers, only 16 of the 203 showed further proliferation of callus. At the end of ~5 months samples from 12 independent calli were tested for the presence of transgene/s by PCR. Examples of explants with callus were positive for both nptII and TDS transgenes.

The four events with profuse callus were separated into individual plates for further growth and observation.

Example 13

PCR Analysis of *Taxus media* Callus Transformed with the Taxadiene Synthase and Cytochrome P450-Dependent Monooxygenase 13-Alpha-Hydroxylase Genes Genomic DNA Preparation from *Taxus* Callus Tissue Of the 522 explants that were inoculated with *A. tumefaciens* strain GV3101 pMP90RK containing plasmid pME4100, 12 putatively transformed *Taxus* calli were identified based on fresh cell proliferation of explants on selection media as described in Example 12. Of the 2775 explants that were inoculated with *Agrobacterium tumefaciens* strain GV3101 pMP90RK containing plasmid pME4103, 80 putatively transformed calli were identified based on fresh cell proliferation of explants growing on medium with selection as described in Example 11. PCR was used to screen putative transgenic calli for integration of the T-DNA for the calli that proliferated on selection medium.

First, *Taxus* genomic DNA was prepared from callus tissue from the putatively transformed explants using the DNAeasy 96 Plant Kit (Qiagen part number 69181) Approximately 50 milligrams (mg) of each callus tissue was harvested from NPTII selection Petri plates and transferred into a collection tube in a 96-well rack. In addition to the putative transformants, wild-type (untransformed) *Taxus* callus tissue was added to one of the tubes in the 96-well rack. One tungsten carbide bead was added to each collection tube. After addition of 402 μL of lysis solution (400 μL AP1 Buffer, 1 μL of 100 mg/mL RNase A, 1 μL reagent DX), collection tubes were sealed with caps. Samples were disrupted using a Mixer Mill 300 for 1.5 min and 30 Hz. The plate was disassembled and rotated in the Mixer Mill. The samples were disrupted for an additional 1.5 min at 30 Hz and centrifuged briefly at 300 rpm. 130 μL of Buffer AP2 was added to each collection tube then the rack of tubes was shaken up and down vigorously for 15 seconds. The rack was briefly centrifuged again at 300 rpm. The rack of collection tubes was incubated for 10 min at −20C then centrifuged for 5 min at 600 rpm to pellet cell debris. Caps were removed and discarded, and 400 μL of each supernatant was transferred to a new rack of collection microtubes, ensuring that the tubes remained in the same orientation in the rack. 1.5 volumes (600 μL) of Buffer AP3/E was added to each sample and samples were covered with new caps. Tubes were vigorously shaken for 15 sec then centrifuged briefly at 300 rpm. 1 mL of supernatant was transferred to corresponding well location in a DNeasy 96 plate and the plate was sealed with an AirPore tape sheet. The plate was centrifuged for 4 min at 6000 rpm. After removing the tape, 800 μL of AW buffer was added to each sample. Samples were covered with a new AirPore tape sheet and the plate was centrifuged for 15 min at 6000 rpm to dry the DNeasy membranes. To elute the DNA, 100 μL Buffer AE was added to each sample on the DNeasy plate, and the plate was sealed with tape, incubated at room temperature for 1 min and centrifuged for 2 min at 600 rpm. DNA elution was repeated with a second 100 μL aliquot of Buffer AE to ensure complete genomic DNA elution. Genomic DNA yield was estimated by spectrophotometer and the quality of genomic DNA purified from the putative transgenics and the wildtype tissue sample was estimated by agarose gel electrophoresis.

PCR Analysis

Genomic DNA prepared from callus tissue above was analyzed by PCR for the presence of the TDS and T13H transgenes and PCR controls. PCR primer sets were designed to selectively amplify portions of 1) the mas1':T13H promoter/ gene junction for pME4103-transformed calli; 2) the mas1': TDS promoter/gene junction for pME4100-transformed calli; 3) the NPTII gene; 4) the *Taxus* endogenous GAPDH gene; and 4) the spectinomycin gene located on the plasmid backbone. Descriptions and nucleotide sequences of primers used in PCR screening of the putative transgenics are shown in Table 9.

TABLE 9

Primer sequences used for screening putatively transgenic *Taxus* calli for integration of the T-DNA.

| Primer ID | Primer description | Primer Sequence | Primer length (bp) | PCR product size (bp) |
|---|---|---|---|---|
| GAPDH_190.F SEQ ID NO: 30 | Forward primer for GAPDH gene | CTCTCTGTTCAAGTATGACAGT | 22 | 1500 |
| GAPDH_599.R SEQ ID NO: 31 | Reverse primer for GAPDH gene | GTACAGTTGTCATTAGACCTTC | 22 | |
| SPEC1A SEQ ID NO: 32 | Forward primer for Spectinomycin resistance gene | TGCCGACTACCTTGGTGATCTC | 22 | 566 |
| SPEC2 SEQ ID NO: 33 | Reverse primer for Spectinomycin resistance gene | CGGCTTCCCCTGGAGA | 16 | |
| NPT3 SEQ ID NO: 34 | Forward primer for NPTII gene | GCCAACGCTATGTCCTGA | 18 | 346 |
| NPT5 SEQ ID NO: 35 | Reverse primer for NPTII gene | CCTGCCGAGAAAGTATGC | 18 | |
| MASPROSEQ1 SEQ ID NO: 36 | Forward primer for mas1' promoter | GTCCTACACGCCGAAATAAA | 20 | 630 |
| T13aH_426.R SEQ ID NO: 37 | Reverse primer for T13H gene | AAACCGAGTTAGTGCAGC | 18 | 613 |
| TDS_430.R SEQ ID NO: 38 | Reverse primer for TDS gene | GACTGATATCTCCGTCTCC | 19 | |

PCR Conditions:

To perform PCR, 1:100 dilution of the genomic DNA was prepared in water. A 25 μL PCR reaction contained 15.7 μL water, 2.5 μL of 10× Jumpstart PCR buffer (Sigma), 0.5 μL of 10 mM dNTP mix, 1 μL of 1 U/μL Jumpstart polymerase blend, 0.15 μL of a 50 μM solution of the forward primer, 0.15 μL of a 50 μM solution of the reverse primer, and 5 μL of the diluted genomic DNA template. PCR controls included templates of 1) 6 ng of genomic DNA prepared from wildtype (untransformed) *Taxus media* calli, 2) 5 pg of pME4100 or pME4103 plasmid DNA, and 3) sterile water.

PCR conditions for pME4100 (mas1'TDS) and pME4103 (mas1'T13H) detection from genomic DNA preparations: 95° C. for 2 minutes; 35 cycles of 95° C. for 30 seconds, 53° C. for 30 seconds, 72° C. for 1 minute; and 72° C. for 10 minutes. PCR conditions for internal control GAPDH gene from genomic DNA template: 95° C. for 2 minutes; 35 cycles of 95° C. for 1 minute, 57° C. for 1 minute, 72° C. for 1.5 minute; and 72° C. for 10 minutes.

Results

PCR was performed on genomic DNA in the above conditions to screen putative transgenic *Taxus* calli for the presence of the TDS or T13H transgenes. PCR results from representative gels are shown below in FIG. 3 and FIG. 4.

Figure 3:
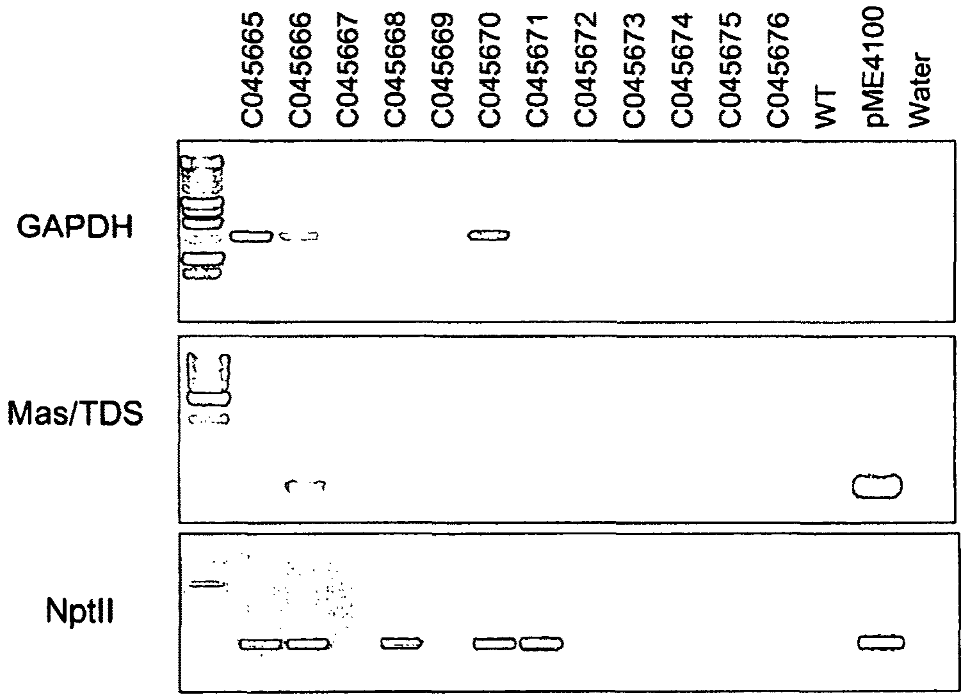
FIG. 3 shows a representative PCR of *Taxus* calli transformed with pME4100 (mas1:TDS).

As shown in FIG. 3, putative calli and WT callus showed endogenous GAPDH-specific PCR product. The samples C045665, C045666, C045668 and C045670 amplified both NPT II and mas/TDS-specific PCR products whereas C045671 showed only NPT II-specific PCR product. The WT control is negative for both NPT II and mas/TDS. These results suggest that four samples contain TDS transgene.

Figure 4:
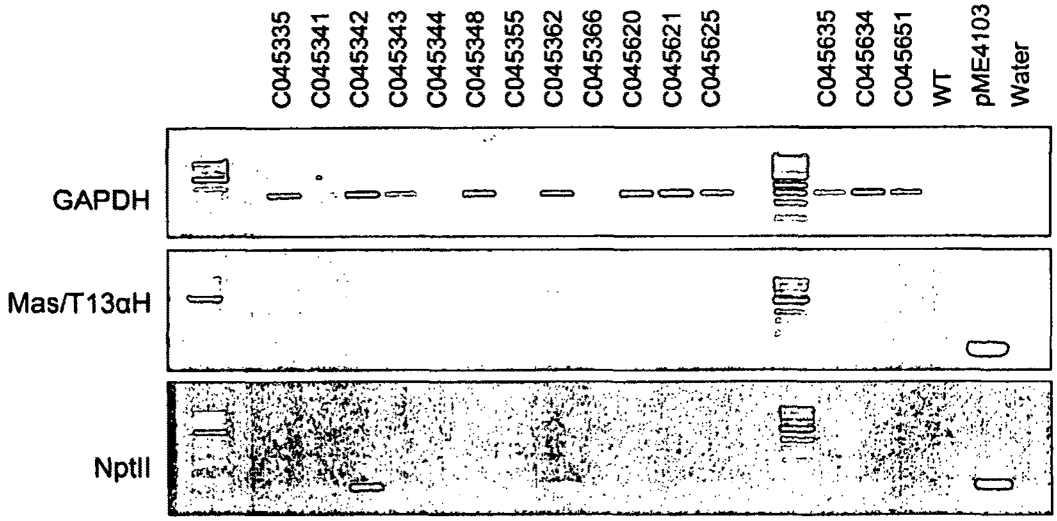
FIG. 4 shows a representative PCR of *Taxus* calli transformed with pME4103 (mas1:T13H).

FIG. 4 shows the PCR results from a representative gel of T13H transformed calli. The WT callus and all putative calli, except C045355 showed endogenous GAPDH PCR product conforming the quality of genomic DNA preparation. The samples C045335, C04541, C045343, C045348, C045355, C045362, C045620, C045635 and C045634 yielded both mas/T13H and NPT II-specific PCR products. Some samples showed either T13H transgene (e.g., C045366 and C045651) or NPT II (e.g., C045342, C045621 and C045625), suggesting that the partial integration of t-DNA in these samples. As expected wt control callus did not amplify t-DNA-specific sequences. These results suggest that nine samples contain T 13H transgene. Data from all screened calli are provided in Table 13 in Example 21.

The following nine Examples provide optional modifications and/or improvements in methodology, which raised the transformation frequency to 23.3% (See Tables 10 and 11). The protocol and media composition described in Examples 16 and 17 profoundly impacted the transformation efficiency, as reflected in the experiments with paclitaxel pathway genes (Tables 12 and 13). The transformation frequency was up to >50% in some instances using the modified procedure and media composition. In addition to bark peel explants, the peeled stem also proved to be an excellent source for effective transformation by *Agrobacterium*.

Example 14

Transformation of *Taxus media* 'Hicksii' Using *Agrobacterium tumefaciens* Strain EHA101 Containing Plasmid pAG4017 (CsVMV-nptII/MelActin-intron-GUS)

Materials and Methods

*Agrobacterium* suspension was prepared as in Example 11. The *Agrobacterium* strain EHA101 was transformed with the vector pAG4017 which is identical to pAG4015 except that a 189 base pair intron from potato light-inducible tissue-specific ST-LS1 gene (gene accession # X04753) was introduced between the melon actin promoter and the Gus coding sequence (FIG. 1).

*Taxus* twigs were collected from University of Portland. The material was sterilized and bark peels were excised as in Example 11. Additionally, the twigs with the bark peeled off were also utilized as explant source. These twigs were cut into small pieces as well and are called peeled stem explants.

Bark peel and peeled stem explants were incubated with *Agrobacterium* suspensions mixed with liquid co-cultivation medium (TM00000556) in Petri plates. After 30-40 minutes the explants were blotted on sterile filter paper and plated on solid medium (TM00000555). In case of bark peel explants the cut surface was in contact with the medium while the peeled stem explants were placed horizontally on the medium. After three days of co-cultivation on solid medium, the explants were transferred to flask for rinsing with medium TM00000575. After rinsing, explants were blotted and plated on selection media TM00000557 and TM00000558. After identification of GUS-positive explants all cultures were transferred to TM00000612 (with geneticin at 20 mg/L). The control explants not exposed to *Agrobacterium* were plated on TM00000559 without selection antibiotic.

Results

The explants started showing signs of callus formation at the end of two to three weeks. All explants were transferred periodically to fresh medium. Some of the explants on subsequent transfers failed to continue callus growth. About four months after initiation of the experiment, the explants were scored on the basis of presence or absence of noticeable callus. From a total of 463 explants (302 bark peel and 161 peeled stem) 27 calli were formed and 10 of these showed GUS-positive staining (Table 10).

Example 15

Transformation of *Taxus media* 'Hicksii' Using *Agrobacterium tumefaciens* Strain EHA101 Containing Plasmid pAG4015 (CsVMV-nptII/MelActin-GUS)

Methods and Materials:

*Agrobacterium* suspension was prepared as in Example 11.

*Taxus* twigs were collected from University of Portland. The material was sterilized and bark peels were excised as in Example 11. Additionally, the twigs with the bark peeled off were also utilized as explant source. These twigs were cut into small pieces as well and are called peeled stem explants.

Bark peel and peeled stem explants were incubated in *Agrobacterium* suspension mixed with liquid co-cultivation medium (TM00000579) with the bacterial density of $5\times10^8$ cells/ml in a shaker at 100-120 rpm. After 90' of incubation the medium is decanted off and the explants are blotted on sterile filter paper and plated on solid co-cultivation medium (TM00000580) for 3 days with the cut surface in contact with the medium. After a total of 3 days co-cultivation, explants were transferred to flask with rinsing medium (TM00000575). After brisk shaking the medium is decanted off and the explants were plated on selection media (TM00000581 or TM00000582) with the cut surface away from the medium. The control explants not exposed to *Agrobacterium* are plated on TM00000583 without selection antibiotic.

Screening of transformed callus and subculture intervals were as described in previous examples. After a few transfers (2-4) the explants receiving geneticin antibiotic at 7.5 mg/l (i.e. TM00000582) were transferred to higher level of geneticin, i.e., 12 mg/l (TM00000621). The transformed calli are maintained on TM00000581 (kanamycin selection) or TM00000621 (geneticin selection)

Results

The explants started showing signs of callus formation at the end of 2-3 weeks. All explants were transferred periodically to fresh medium. Some of the explants on subsequent transfers failed to continue callus growth. At the end of ~4 months after initiation of the experiment, the explants were scored on the basis of presence or absence of noticeable callus. From a total of 619 (520 bark peel and 99 peeled stem) explants 396 had callus and 84 of these showed GUS-positive staining (Table 10).

Example 16

Transformation of *Taxus media* 'Hicksii' Using *Agrobacterium tumefaciens* Strain EHA101 Containing Plasmid pAG4015 (CsVMV-nptII/MelActin-GUS)

Materials and Methods

In this example methods unique to Example 14 (explant preconditioning) and Example 15 (incubation conditions and media composition) were combined. Only bark peel tissue was used in this experiment. Bark peel explants were preconditioned prior to infection with *Agrobacterium*. The explants were cultured on TM00000308 with the cut surface away from the medium. After eight days of culture explants were incubated in *Agrobacterium* suspension mixed with liquid co-cultivation medium (TM00000579) with the bacterial density of $5\times10^8$ cells/ml in a shaker at 100-120 rpm. After 90' of incubation, the medium is decanted off and the explants are blotted on sterile filter paper and plated on solid co-cultivation medium (TM00000580) with the cut surface in contact with the medium. After a total of three days co-cultivation, explants were transferred to flask with rinsing medium (TM00000575). After brisk shaking the medium is decanted off and the explants were plated on selection media (TM00000581 or TM00000582) with the cut surface away from the medium. The control explants not exposed to *Agrobacterium* are plated on TM00000583 without selection antibiotic.

Screening of transformed callus and subculture intervals are as described in previous examples. After a few transfers (2-4) the explants receiving geneticin antibiotic at 7.5 mg/l (e.g. TM00000582) were transferred to higher level of geneticin, i.e., 12 mg/l (TM00000621). The transformed calli were maintained on TM00000581 (kanamycin selection) or TM00000621 (geneticin selection)

Results

The explants started showing signs of callus formation at the end of 2-3 weeks. All explants were transferred periodically to fresh medium. Some of the explants on subsequent transfers failed to continue callus growth. About four months after initiation of the experiment, the explants were scored on the basis of presence or absence of noticeable callus. From a total of 241 explants, 32 had callus and 30 of these showed GUS-positive staining (Table 10).

Example 17

Transformation of *Taxus media* 'Hicksii' Using *Agrobacterium tumefaciens* Strain EHA101 Containing Plasmid pAG4015 (CsVMV-nptII/MelActin-GUS)

Materials and Methods

Experimental protocol was identical to Example 16 except that peeled stem was used as explant source. Peeled stem explants (3-5 nm length) were preconditioned prior to infection with *Agrobacterium*. The explants were cultured on TM00000308 placing the segments horizontally on the medium. After eight days of culture explants were incubated in *Agrobacterium* suspension mixed with liquid co-cultivation medium (TM00000579) with the bacterial density of $5\times10^8$ cells/ml in a shaker at 100-120 rpm. After 90' of incubation, the medium is decanted off and the explants are blotted on sterile filter paper and plated on solid co-cultivation medium (TM00000580) for three days. After a total of three days co-cultivation, explants were transferred to flask with rinsing medium (TM00000575). After brisk shaking the medium is decanted and the explants were plated horizontally on selection media (TM00000581 or TM00000582). The control explants not exposed to *Agrobacterium* are plated on TM00000583 without selection antibiotic.

Screening of transformed callus and subculture intervals were as described in previous examples. After a few transfers (2-4), the explants receiving geneticin antibiotic at 7.5 mg/l (e.g. TM00000582) were transferred to higher level of geneticin, e.g. 12 mg/l (TM00000621). The transformed calli were maintained on TM00000581 (kanamycin selection) or TM00000621 (geneticin selection).

| Media Composition (used in Examples 14-17) | | |
|---|---|---|
| **TM00000308** | | |
| SH SALTS | 3.2000 | g/L |
| NN VITAMINS | 1.0000 | units/L |
| SUCROSE | 30.0000 | g/L |
| NAA | 6.0000 | mg/L |
| 2,I-P | 0.5000 | mg/L |
| 2,4-D | 1.0000 | mg/L |
| L-GLUTAMINE | 800.0000 | mg/L |
| PHYTAGEL | 2.5000 | g/L |
| **TM00000555** | | |
| SH SALTS | 3.2000 | g/L |
| NN VITAMINS | 1.0000 | units/L |
| 2,4-D | 1.0000 | mg/L |
| NAA | 4.0000 | mg/L |
| D-GLUCOSE | 20.0000 | g/L |
| SUCROSE | 20.0000 | g/L |
| ASCORBIC ACID | 100.0000 | mg/L |
| 2,I-P | 0.5000 | mg/L |
| IAA | 4.0000 | mg/L |
| L-GLUTAMINE | 800.0000 | mg/L |
| L-CYSTEINE | 400.0000 | mg/L |
| AS | 100.0000 | µM |
| PHYTAGEL | 10.0000 | g/L |
| L-PROLINE | 400.0000 | mg/L |

-continued

| Media Composition (used in Examples 14-17) | | |
|---|---|---|
| **TM00000556** | | |
| SH SALTS | 3.2000 | g/L |
| NN VITAMINS | 1.0000 | units/L |
| 2,4-D | 1.0000 | mg/L |
| NAA | 4.0000 | mg/L |
| D-GLUCOSE | 20.0000 | g/L |
| SUCROSE | 20.0000 | g/L |
| ASCORBIC ACID | 100.0000 | mg/L |
| 2,I-P | 0.5000 | mg/L |
| IAA | 4.0000 | mg/L |
| L-GLUTAMINE | 800.0000 | mg/L |
| L-CYSTEINE | 400.0000 | mg/L |
| AS | 100.0000 | µM |
| L-PROLINE | 400.0000 | mg/L |
| **TM00000557** | | |
| SH SALTS | 3.2000 | g/L |
| NN VITAMINS | 1.0000 | units/L |
| SUCROSE | 20.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| KANAMYCIN | 300.0000 | mg/L |
| IAA | 4.0000 | mg/L |
| **TM00000558** | | |
| SH SALTS | 3.2000 | g/L |
| NN VITAMINS | 1.0000 | units/L |
| SUCROSE | 20.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| GENETICIN | 15.0000 | mg/L |
| IAA | 4.0000 | mg/L |
| **TM00000559** | | |
| SH SALTS | 3.2000 | g/L |
| NN VITAMINS | 1.0000 | units/L |
| SUCROSE | 20.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| IAA | 4.0000 | mg/L |
| **TM00000575** | | |
| B5 SALTS | 3.0800 | g/L |
| NN VITAMINS | 1.0000 | units/L |
| 2,4-D | 1.0000 | mg/L |
| NAA | 4.0000 | mg/L |
| SUCROSE | 30.0000 | g/L |
| 2,I-P | 0.5000 | mg/L |
| IAA | 2.0000 | mg/L |
| TIMENTIN | 500.0000 | mg/L |
| **TM00000579** | | |
| SH SALTS | 3.2000 | g/L |
| NN VITAMINS | 1.0000 | units/L |
| 2,4-D | 1.0000 | mg/L |
| NAA | 4.0000 | mg/L |
| D-GLUCOSE | 20.0000 | g/L |
| SUCROSE | 20.0000 | g/L |
| ASCORBIC ACID | 100.0000 | mg/L |
| 2,I-P | 0.5000 | mg/L |
| IAA | 4.0000 | mg/L |
| L-GLUTAMINE | 800.0000 | mg/L |
| L-CYSTEINE | 400.0000 | mg/L |
| AS | 100.0000 | µM |

-continued

| Media Composition (used in Examples 14-17) | | |
|---|---|---|
| L-PROLINE | 400.0000 | mg/L |
| CONIFERYL ALCOHOL | 100.0000 | µM |
| TM00000580 | | |
| SH SALTS | 3.2000 | g/L |
| NN VITAMINS | 1.0000 | units/L |
| 2,4-D | 1.0000 | mg/L |
| NAA | 4.0000 | mg/L |
| D-GLUCOSE | 20.0000 | g/L |
| SUCROSE | 20.0000 | g/L |
| ASCORBIC ACID | 100.0000 | mg/L |
| 2,I-P | 0.5000 | mg/L |
| IAA | 4.0000 | mg/L |
| L-GLUTAMINE | 800.0000 | mg/L |
| L-CYSTEINE | 400.0000 | mg/L |
| AS | 100.0000 | µM |
| PHYTAGEL | 10.0000 | g/L |
| L-PROLINE | 400.0000 | mg/L |
| CONIFERYL ALCOHOL | 100.0000 | µM |
| TM00000581 | | |
| SH SALTS | 3.2000 | g/L |
| NN VITAMINS | 1.0000 | units/L |
| SUCROSE | 30.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| KANAMYCIN | 150.0000 | mg/L |
| IAA | 4.0000 | mg/L |
| TM00000582 | | |
| SH SALTS | 3.2000 | g/L |
| NN VITAMINS | 1.0000 | units/L |
| SUCROSE | 30.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| GENETICIN | 7.5000 | mg/L |
| IAA | 4.0000 | mg/L |
| TM00000583 | | |
| SH SALTS | 3.2000 | g/L |
| NN VITAMINS | 1.0000 | units/L |
| SUCROSE | 30.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| IAA | 4.0000 | mg/L |
| TM00000621 | | |
| SH SALTS | 3.2000 | g/L |
| NN VITAMINS | 1.0000 | units/L |
| SUCROSE | 30.0000 | g/L |
| 2,4-D | 1.0000 | mg/L |
| NAA | 4.0000 | mg/L |
| 2,I-P | 0.5000 | mg/L |
| L-GLUTAMINE | 800.0000 | mg/L |
| PHYTAGEL | 2.5000 | g/L |
| TIMENTIN | 250.0000 | mg/L |
| GENETICIN | 12.0000 | mg/L |
| IAA | 4.0000 | mg/L |
| TM00000612 | | |
| SH SALTS | 3.2000 | g/L |
| NN VITAMINS | 1.0000 | units/L |
| SUCROSE | 20.0000 | g/L |
| 2,4-D | 1.0000 | mg/L |
| NAA | 4.0000 | mg/L |
| PHYTAGEL | 2.5000 | G/L |

-continued

| Media Composition (used in Examples 14-17) | | |
|---|---|---|
| 2,I-P | 0.5000 | mg/L |
| L-GLUTAMINE | 800.0000 | mg/L |
| TIMENTIN | 250.0000 | mg/L |
| GENETICIN | 20.0000 | mg/L |
| IAA | 4.0000 | mg/L |

Results

The explants started showing signs of callus formation at the end of 2-3 weeks. All explants were transferred periodically to fresh medium. Some of the explants on subsequent transfers failed to continue callus growth. About four months after initiation of the experiment, the explants were scored on the basis of presence or absence of noticeable callus. From a total of 60 explants 16 had callus and 14 of these showed GUS-positive staining (Table 10).

TABLE 10

Results of GUS-staining of putative calli identified in Examples 14-17 showing transformation frequency of *Taxus media* 'Hicksii' using both bark peel and peeled stem explants.

| Example | Construct ID | Explant Source | Gus-positive calli/total explants | Transformation frequency |
|---|---|---|---|---|
| 14 | pAG4017 | Bark peel and peeled stem | 10/463 | 2.2% |
| 15 | pAG4015 | Bark peel and peeled stem | 84/619 | 13.6% |
| 16 | pAG4015 | Bark peel | 30/241 | 12.4% |
| 17 | pAG4015 | Peeled stem | 14/60 | 23.3% |

Example 18

Figure 5A:
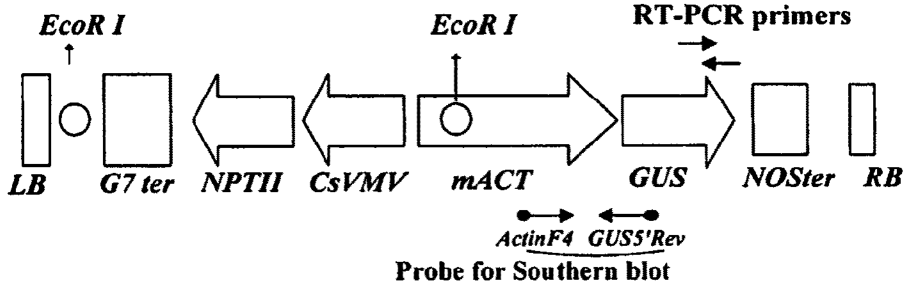
FIGS. 5A-5C illustrate molecular analysis of *Taxus media* calli transformed with pAG4015.
Figure 5B:
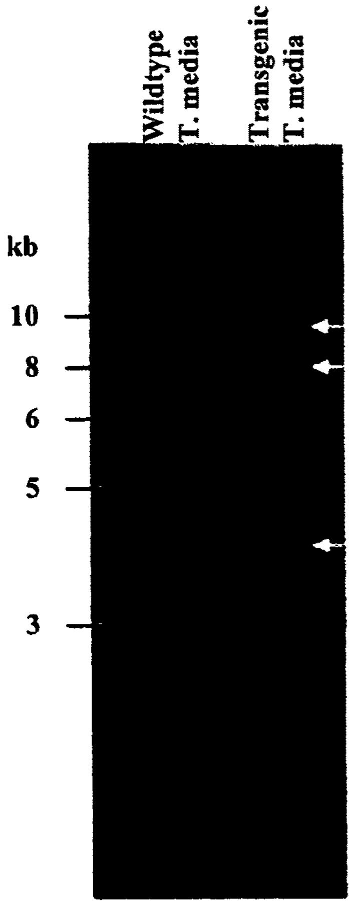

Molecular Confirmation of *Taxus media* Transgenic Callus Transformed with mACTIN:GUS (pAG4015) Vector One of the PCR confirmed *Taxus media* transgenic callus transformed with pAG4015 vector described in Example 4 was further confirmed as being transgenic by Southern blot analysis and RT-PCR analysis. Genomic DNA from the *Taxus media* transgenic callus and wildtype *Taxus media* was isolated (FIG. 5). The high molecular weight DNA was digested with EcoR I and blotted to Nylon membrane. The blot was hybridized with a region span across mACTIN promoter and GUS coding region, a 484 bp fragment (FIG. 5A). The 484 bp fragment was labeled non-radioactive DIG-based method according to the manufacture instructions (Roche Diagnostics GmbH, Germany). The results showed that transgenic *Taxus media* contains three hybridizing bands after probing, suggesting that the transgenic *Taxus media* transformed with pAG4015 has three T-DNA insertions into its genome (FIG. 5B). The fourth bottom band which is common in both wildtype and transgenic *Taxus media* seems to be a non-specific hybridizing band in the *Taxus media* genome (FIG. 5B).

Figure 5C:
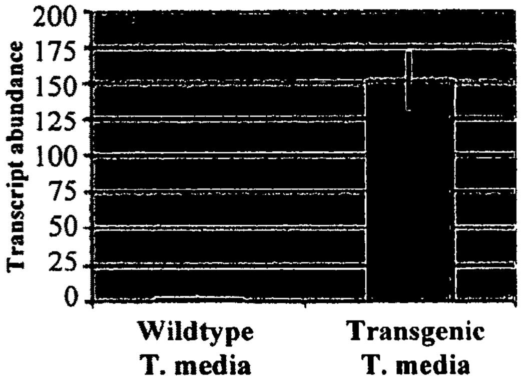

To further confirm, RT-PCR analysis was performed with the same callus. Total RNA was isolated from the same transgenic callus using Qiagen RNEsay kit (Qiagen). The first strand cDNA was synthesized using Promega company kit, Reverse Transcription System. Briefly, 1 µg of total RNA was used to reverse transcribe the mRNA isolated from wildtype and transgenic callus lines suing oligo (dT) primers. Then equal amounts of first strand cDNA was used to amplify GUS gene-specific primer set for transgene GUS transcript and GAPDH-specific primer set for endogenous GAPDH gene transcript. The primers for GUS transcript are: GUS.7064_3'end.F1 (5'-TGGCATGAACTTCGGTGAAA-3'; SEQ ID NO: 39) and GUS.7711_3'UTR.R1 (5'-TCGAGCTCGG-TAGCAATTCC-3'; SEQ ID NO: 40). The primers for endogenous GAPDH transcript are: GAPDH.836.F1 (5'-ATCAAG-GCTGCCATCAAGGA-3'; SEQ ID NO: 41) and GAPDH.942.R1 (5'-CTTGATCGACTGTCTCCGATGA-3'; SEQ ID NO: 42). Expression of the GUS gene was measured by the quantitation of cDNA on an ABI7700 (Applied Biosystems, Foster City, Calif.). The calibrator sample was cDNA converted from RNA using oligo d(T) primers in a first strand cDNA synthesis reaction using RNA isolated from wild type *Taxus* callus tissue. All quantitations for this RT-PCR SYBR Green assay were normalized to an endogenous control, GAPDH, to account for variability of initial concentration and quality of total RNA and for the conversion efficiency of the reverse transcription assay. The mean GUS transcript abundance in the transgenic relative to wild type, after normalizing to GAPDH with two replicates compared across templates was 151.34 (standard error, 19.35). As shown in FIG. 5C, the transgene-specific GUS transcript is abundant in the *Taxus media* transgenic line and no GUS-specific transcript is found in the control wildtype *Taxus media*.

Example 19

Construction of Transformation Vectors Carrying Genes Coding for Paclitaxel Pathway Enzymes Driven by Two Constitutive Plant Expression Promoters for Expression in Transgenic *Taxus media* Cells The parental vector pME4001 vector, as described in Example 10, was used to prepare *Taxus* MAS1' promoter-based plant expression vectors. Paclitaxel pathway genes such as *Arabidopsis* geranylgeranyl diphosphate synthase 1, GGDPS1 (At4g36810), *Mentha x piperita* L. (mint) deoxyxylulose phosphate synthase (DXPS, gene bank accession number AF019383, Lange et al., *Proc Natl Acad Sci USA*, 9:2100-2104, 1998), mint deoxyxylulose phosphate reductase (DXR, AF116825, Lange & Croteau, *Arch. Biochem. Biophys.* 365 (1), 170-174, 1999) *Taxus canadensis* taxoid 5α-hydroxylase (T5H) (Jennewein et al., *Proc Natl Acad Sci USA* 101:9149-9154, 2004), *Taxus canadensis* taxoid 13α-hydroxylase (T13H) (Jennewein et al., *Proc Natl Acad Sci USA* 101:9149-9154, 2004) and *Taxus canadensis* taxoid 2-O-benzoyltransferase (T-2-O-BT) (Jennewein et al., *Proc Natl Acad Sci USA* 101:9149-9154, 2004) were cloned into the pME4001 using Spe I and KpnI sites between MAS1'promoter and NOS terminator. The cDNA sequences were PCR amplified using the gene-specific primer sets described in the Table 11. The gene-specific forward primer consists Spe I site (ACTAGT) and GACC Kozak sequence before AUG codon of each coding sequence and the reverse primer has Kpn I site (GGTACC) followed by stop codon of each gene.

TABLE 11

Primer sequences to amplify full-length coding regions of seven paclitaxel pathway genes.

| Gene/Primer Name | Primers | SEQ ID |
|---|---|---|
| TDS_F3 | TCAGGACTAGTGACCATGGCTCAGCTCTCATTTAATG | 43 |
| TDS_R3 | TACGGGGTACCTCATACTTGAATTGGATCAA | 44 |
| GGDPS1_F3 | TCAGGACTAGTGACCATGGCTTCAGTGACTCTAGGT | 45 |
| GGDPS1_R3 | TACGGGGTACCTCAGTTCTGTCTATAGGCAATGTA | 46 |
| DXR_F3 | TCAGGACTAGTGACCATGGACCATGGCTCTAAACTTGATGGCT | 47 |
| DXR_R3 | TACGGGGTACCTCATACAAGAGCAGGACTCAAAC | 48 |
| T5H_F3 | TCAGGACTAGTGACCATGGACGCCCTGTATAAGAG | 49 |
| T5H_R3 | TACGGGGTACCCTATGGTCTGGGAAACAGTTTAAT | 50 |
| T13H_F3 | TCAGGACTAGTGACCATGGATGCCCTTAAGCAATTG | 51 |
| T13H_R3 | TACGGGGTACCTTAAGATCTGGAATAGAGTTTAATGG | 52 |
| (TAX2) | | |
| T-2-O-BT_F3 | TCAGGACTAGTGACCATGGGCAGGTTCAATGTAG | 53 |
| T-2-O-BT_R3 | TACGGGGTACCTTATAACTTAGAGTTACATATTTTAGC | 54 |
| DXPS_F3 | TCAGGACTAGTGACCATGGCATCTTCCTGTGGAG | 55 |
| DXPS_R3 | TACGGGGTACCTTACAAATTATTAATCAAATGAAGACTGTCC | 56 |

The PCR was performed using high fidelity DNA polymerase. The PCR products were purified and digested with Spe I-Kpn I and ligated into the SpeI-KpnI digested pME4001. The resultant constructs were named as pME4100 (MAS1':TDS), pME4001 (MAS1':GGDPS1), pME41002 (MAS1':T5H), pME4103 (MAS1':T13H), pME41004 (MAS1':TAX2), pME4105 (MAS1':DXPS) and pME4106 (MAS1':DXR). All constructs were confirmed by restriction enzyme analysis and sequencing of both strands.

The CH29 promoter-based TDS and DXPS *Taxus* plant expression constructs were prepared by removing MAS1' promoter from the pME4100 (MAS1':TDS) and pME4105 (MAS1':DXPS), respectively. The pME4100 and pME4105 vectors were digested with SmaI-SpeI to remove MAS1'promoter. The resultant vectors were blunted with klenow. The CH29 promoter sequence was isolated from PCR blunt CH29 Pro vector by digesting with EcoRI and filled with klenow. Then the CH29 promoter was cloned into the SmaI-SpeI (filled) vector fragment of pME4100 and pME4105. The resultant constructs were confirmed by restriction digestion and sequence analysis and named as pME4300 (CH29:TDS) and pME4305 (CH29:DXPS). Followed by ligation between SpeI (filled) vector and EcoRI (filled) fragments, the EcoR I site was restored between CH29 promoter and TDS or DXPS coding regions in pME4301 and pME4305 vectors. Therefore, the CH29:TDS (pME4300) was used to prepare CH29:GGDPS1 (pME4301), CH29:T5H (pME4302), CH29:T13H (pME4303), CH29:TAX2 (pME43004), CH29:DXR (pME4306). First, the CH29:TDS (pME4300) was digested with EcoR I and filled and then digested with Asp718 I to remove TDS coding region. The coding regions of GGDPS1, T5H, T13H, TAX2 and DXR were isolated by digesting pME4101, pME4102, pME4103, pME4104 and pME4106 vectors with SpeI and filled with klenow and then digested with Asp718I. These SpeI (filled)-Asp 718 I fragments of GGDPS1, T5H, T13H, TAX2 and DXR were ligated into the EcoR I (filled)-Asp 718 I digested pME4300 vector. Followed by ligation all sequences were confirmed by restriction digestion and sequence analysis. Representative maps of the *Taxus* plant expression constructs are shown in FIG. 6.

All the sequence-confirmed *Taxus* expression constructs were transformed into *Agrobacterium tumefaciens* strains EHA101 and GV3101 pMP90RK. Constructs were also confirmed by PCR after transformation into *Agrobacterium* and before transformation into *Taxus media* plant. List of all constructs and information on promoter and gene of interest are provided in Table 12.

TABLE 12

Summary of *Taxus* plant expression vectors used in genetic engineering of *Taxus media* 'Hicksii'.

| *Taxus* Expression vector ID | Gene | Promoter |
|---|---|---|
| pME4100 | Taxadiene synthase | MAS1' |
| pME4101 | Geranylgeranyl diphosphate synthase | MAS1' |
| pME4102 | Taxoid 5α-hydroxylase | MAS1' |
| pME4103 | Taxoid 13α-hydroxylase | MAS1' |
| pME4104 | Taxoid 2-O-benzoyltransferase | MAS1' |
| pME4105 | Deoxyxylulose phosphate synthase | MAS1' |
| pME4106 | Deoxyxylulose phosphate reductase | MAS1' |
| pME4300 | Taxadiene synthase | CH29 |
| pME4301 | Geranylgeranyl diphosphate synthase | CH29 |
| pME4302 | Taxoid 5α-hydroxylase | CH29 |
| pME4303 | Taxoid 13α-hydroxylase | CH29 |
| pME4304 | Taxoid 2-O-benzoyltransferase | CH29 |
| pME4305 | Deoxyxylulose phosphate synthase | CH29 |
| pME4306 | Deoxyxylulose phosphate reductase | CH29 |

Example 20

Transformation of *Taxus media* 'Hicksii' Using *Agrobacterium tumefaciens* Strain EHA101 with Genes Coding for Enzymes of the Paclitaxel Pathway

*Agrobacterium tumefaciens* strain EHA101 harboring transformation vectors pME4102, pME4105, pME4302 and pME4305 were used to transform *Taxus media* 'Hicksii' bark peel and peeled stem explants using the protocol described in Examples 16 and 17. The remaining 10 transformation vectors, viz., pME4100, pME4101, pME4103, pME4104, pME4106, pME4300, pME4301, pME4303, pME4304, and pME4306 that were also in *Agrobacterium tumefaciens* strain EHA101 were used to transform *Taxus media* 'Hicksii' bark peel and peeled stem explants as per the protocol described in Example 15. Putative transgenic calli based on callus growth on selection medium as described in Examples 15, 16 and 17 were sampled for genomic PCR analysis and PCR-positive transgenic events were identified as described in Example 21. The results of the PCR analysis are provided in Table 13.

Explant Source

Following initial success with bark peel explants, additional explant source, peeled sterns were targeted for transformation experiments. The idea was conceived to explore the potential of highly meristematic tissues of cambium and phloem to *Agrobacterium* infection, after the removal of bark peel.

Observations Regarding Transformation Efficiency

In at least one case, two independent transformation events arose from one single explant. This is a feature observed only in highly transformable species such as tobacco and some genotypes of tomato. Our methodology has converted the recalcitrant *Taxus* to a highly amenable system for genetic manipulation.

Example 21

Identification of Transgenic Calli by PCR Using Genomic DNA as Template

Figure 6A:
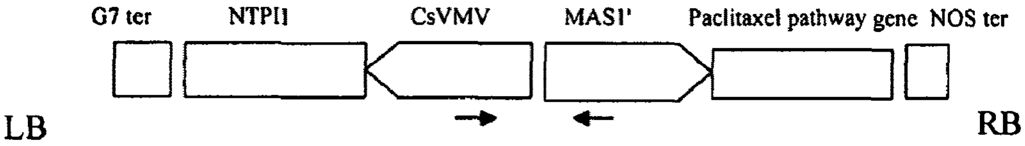
FIGS. 6A-6B show graphic maps of MAS1' promoter and CH29 promoter-based *Taxus media* expression constructs.
Figure 6B:
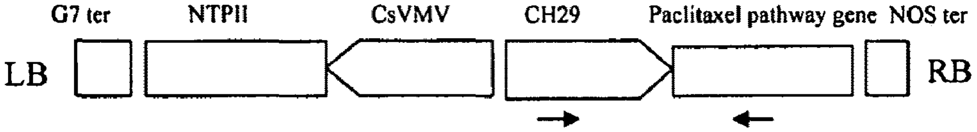

The genomic DNA from putative transgenic calli were prepared and analyzed by PCR by methods similar to those described in Example 4 using different primer sets. All MAS1' promoter-based transgenics were identified using a common set of primers (FIG. 6A). As shown in FIG. 6A, the CsVMV promoter-specific forward primer (CsVMV_Mas.F1; 5'-TGCCGAACTTGGTTCCTTATATAG-3'; SEQ ID NO: 57) and MAS1' promoter-specific reverse primer (CsVMV_Mas.R1 5'-AAGACGTGACGTAAGTATCCGAGT-3'; SEQ ID NO: 58) were used to amplify an 843 bp product from putative *Taxus media* genomic DNA transformed with pME4100, pME4101, pME4102, pME4103, pME4104, pME4105 and pME4106. The CH29 promoter-based transgenics were identified using a common CH29_869.F1 forward primer (5'-GGTCCATTATCCAGGAGG-3'; SEQ ID NO: 59) and a transgene-specific reverse primer for 7 paclitaxel pathway genes (FIG. 6B). The expected PCR product for pME4300 (CH29:TDS), pME4301 (CH29:GGDPS1), pME4302 (CH29:T5H), pME4303 (CH29:T13H), pME4304 (CH29:TAX2), pME4305 (CH29:DXPS), and pME4306 (CH29:DXR) are 819 bp, 859 bp, 760 bp, 836 bp, 831 bp, 897 bp and 1168 bp, respectively. Total number of transgenics identified for each transgene is summarized in Table 13.

TABLE 13

Summary of transgenic calli identified by genomic PCR screening of *Taxus media* calli transformed with seven different paclitaxel pathway genes expressed with either CH29 or MAS1' promoters.

| Gene | Transgenics CH29 Promoter | MAS1' Promoter | Total |
|---|---|---|---|
| Taxadiene synthase | 10 | 7 | 17 |
| Geranylgeranyl diphosphate synthase | 13 | 2 | 15 |
| Deoxyxylulose phosphate reductase | 39 | 79 | 118 |
| Taxoid 5α-hydroxylase | 60 | 119 | 179 |
| Taxoid 13α-hydroxylase | 3 | 50 | 53 |
| Taxoid 2-O-benzoyltransferase | 14 | 35 | 49 |
| Deoxyxylulose phosphate synthase | 2 | 44 | 46 |

Example 22

TDS Transgene Expression Analysis Under the Control of CH29 and MAS1' Promoters in *T. media*

Figure 7A:
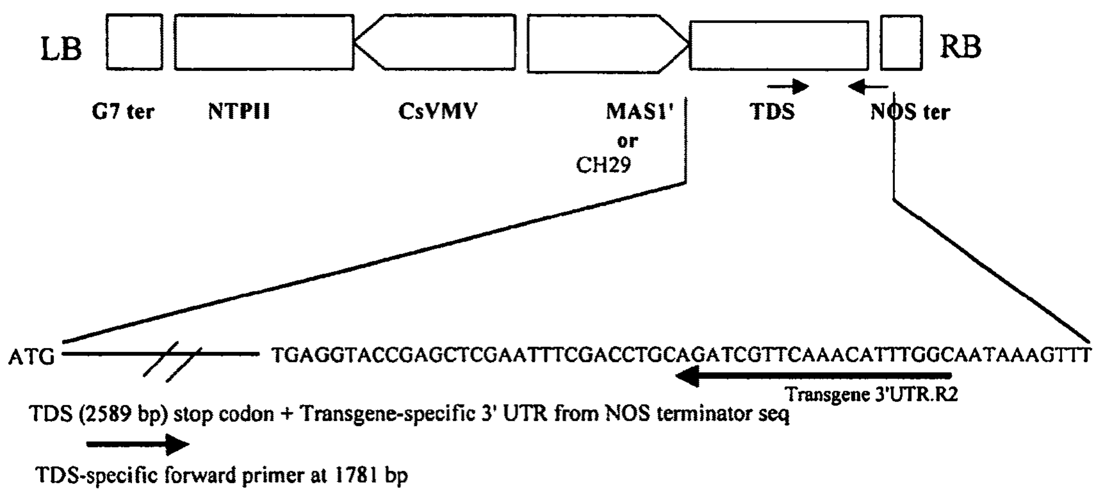
FIGS. 7A-7B illustrate RT-PCR analysis of TDS transgene expression.
Figure 7B:
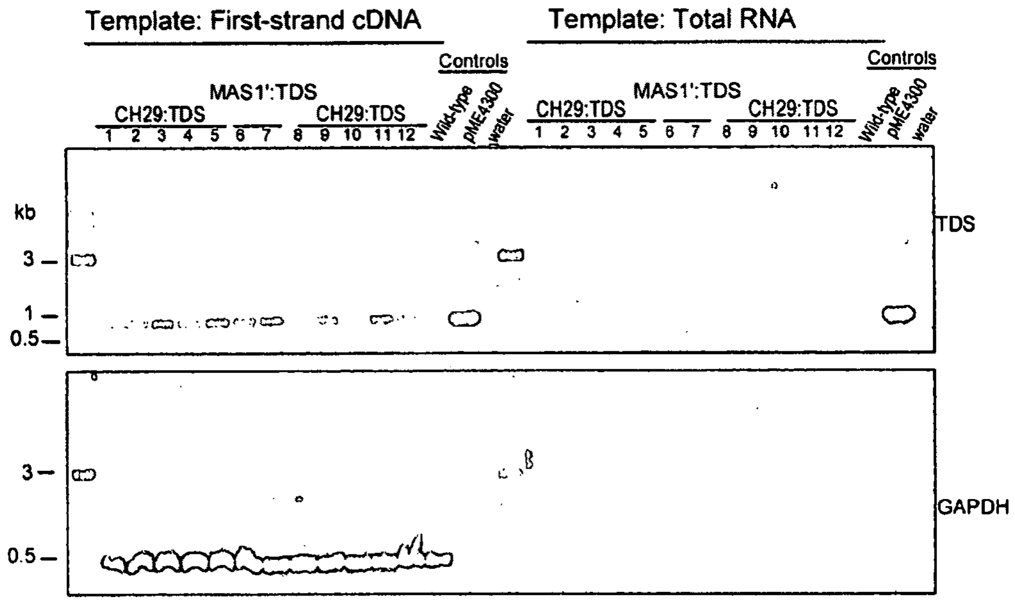

To confirm whether MAS1' and CH29 promoters drive paclitaxel pathway gene expression in transgenic *Taxus media*, RT-PCR analysis was carried out for TDS gene expression using transgenics identified through genomic PCR in Example 21. Total RNA was isolated from 10 CH29:TDS transgenic calli and two MAS 1':TDS calli along with the wild-type control using Qiagen RNEasy kit (Qiagen, Germany). Using Promega Reverse Transcription System (Promega, GmbH, Germany), first strand cDNA was synthesized from 1 μg of total RNA using oligo (dT) primers. Equal volumes of the first-strand cDNA were used as template to detect transgene-specific TDS and endogenous-specific GAPDH transcript (FIG. 7B, left panel). The primers used for transgene-specific TDS are: TDS_1781.F1 (5-CATCAGCTACATTTGAACC-3'; SEQ ID NO: 67) and transgene TDS-specific, transgene 3'UTR.R2 (5-GCCAAATGTTTGAACGATC-3'; SEQ ID NO: 68). This primer set specifically amplifies transgene-specific TDS because the 3'UTR in transgene is unique to the vector and originated from the NOS terminator (FIG. 7A). The PCR results revealed that a transgene-specific PCR product of 858 bp is present in all 12 transgenic calli, 10 carrying CH29:TDS and 2 carrying MAS1':TDS T-DNA regions (FIG. 7B, left panel, TDS). Transgene-specific TDS transcript is not present in wild-type *Taxus media* and vector-specific PCR product is present when plasmid DNA pME4300 was used as template (858 bp product) and no PCR product in the control when water was used as template (FIG. 7B, left panel, TDS). Similarly, endogenous GAPDH-specific transcript is present in all 12 transgenic lines along with the control wild-type *Taxus media*. GAPDH-specific transcript is absent when pME4300 and water were used as templates (FIG. 7B, left panel, GAPDH).

To eliminate the possibility of the presence of the genomic DNA contamination in RNA preparation, a PCR analysis was performed with transgenic TDS primer set and endogenous GAPDH primer set using 1 μg of total RNA from the 12 transgenic lines and wild-type *Taxus media*. Transgene TDS-specific and endogenous GAPDH-specific PCR products were not obtained when total RNA was used as template in PCR (FIG. 7B, right panel, TDS and GAPDH). As expected, vector-specific (pME4300) positive control TDS product is found when plasmid DNA was used as template in PCR. These results revealed that since *Agrobacterium tumefaciens* does not make poly A tails in mRNA population and oligo dT primers were used in reverse transcription system, the resultant PCR products when first-strand cDNA was used as template in PCR are originated from the expression of transgene TDS under the regulation of CH29 promoter or MAS1' promoter. As these promoters activate TDS gene expression in *T. media*, expression of other genes including GGDPS1, T5H, T13H, TAX2, DXPS and DXR are expected to also express in transgenics identified in Example 21.

Example 23

Methods for Extraction and Analysis of Taxanes

This example provides representative methods for analyzing the taxane content of transgenic (or non-transgenic) *Taxus* cells and cell cultures. The methods provided are representatively only, and one of ordinary skill in the art will recognize that other methods, and modifications of the provided methods, may be used.

Preparation of *Taxus* Calli Extracts

Putative transgenic *Taxus* calli prepared for instance as described above, and harboring for instance either the TDS cassette or the 13α-hydroxylase cassette, along with control calli from the respective experiments, are analyzed for taxane content and profiles. Calli are dissected aseptically and 0.25-0.5 g of accurately weighed callus is transferred to a well of a 96 deep-well plate (Qiagen Inc., Valencia, Calif.). A 3 mm tungsten-carbide bead (Qiagen Inc., Valencia, Calif.) and 0.5 ml of methanol/water (50150 v/v) is added to the well. The mixture is shaken on the mixer-mill (F. Kurt Retsch GmbH and Co., Haan, Germany) twice for 1 minute at 20 shakes per second. The plate is then centrifuged at 6,000 RPM for 5 minutes, to produce extract for analysis.

Solid Phase Extraction of Taxanes

Solid phase extraction (SPE) is carried out by transferring 0.5 ml of extract into an Oasis HLB 96-well Extraction Plate (Waters Corporation, Milford, Mass.) that has been equilibrated with 60/40 water/methanol. The well is then washed with 60/40 water/methanol. Taxanes are eluted with 0.5 ml of methanol per sample and drawn through SPE plate into a 96-well collection plate. The extracts are immediately analyzed by HPLC-MS.

HPLC-MS Analysis and Quantification

Ten microliters of *Taxus* callus extract is injected and separated by the Waters 600S Controller with 626 Pump HPLC (Waters Corporation, Milford, Mass.) over an Agilent Hypersil ODS 3 μm, 2.1×100 mm column (Agilent Technologies, Inc., Wilmington, Del.). Initial pump conditions are 75% A (0.1% formic acid in water) and 25% B (0.1% formic acid in Acetonitrile) ramping up to 85% B in 10 minutes and holding at 100% B for another 5 minutes at a flow rate of 0.3 ml/minute. A re-equilibration time of 7 minutes gives an injection to injection run time of 22 minutes.

The Micromass Quattromicro mass spectrophotometer with a triple-quadrupole is run in Selective Ion Monitoring mode (Micromass UK Limited, Manchester, United Kingdom). The ions monitored and the corresponding taxane are, for instance: 545 (10-deacetylbaccatin), 587 (baccatin III), 812 (10-deacetyltaxol), 832 (cephalomannine), 854 (paclitaxel), and 848 (taxol C). Cone voltage is set at 15 V and capillary voltage at 35 kV. Source temperature is 115° C. with desolvation temperature of 300° C. and desolvation gas set at 600 L/hour. Mass Lynx 4.0 software controls both HPLC and Mass Spec.

Figure 8:
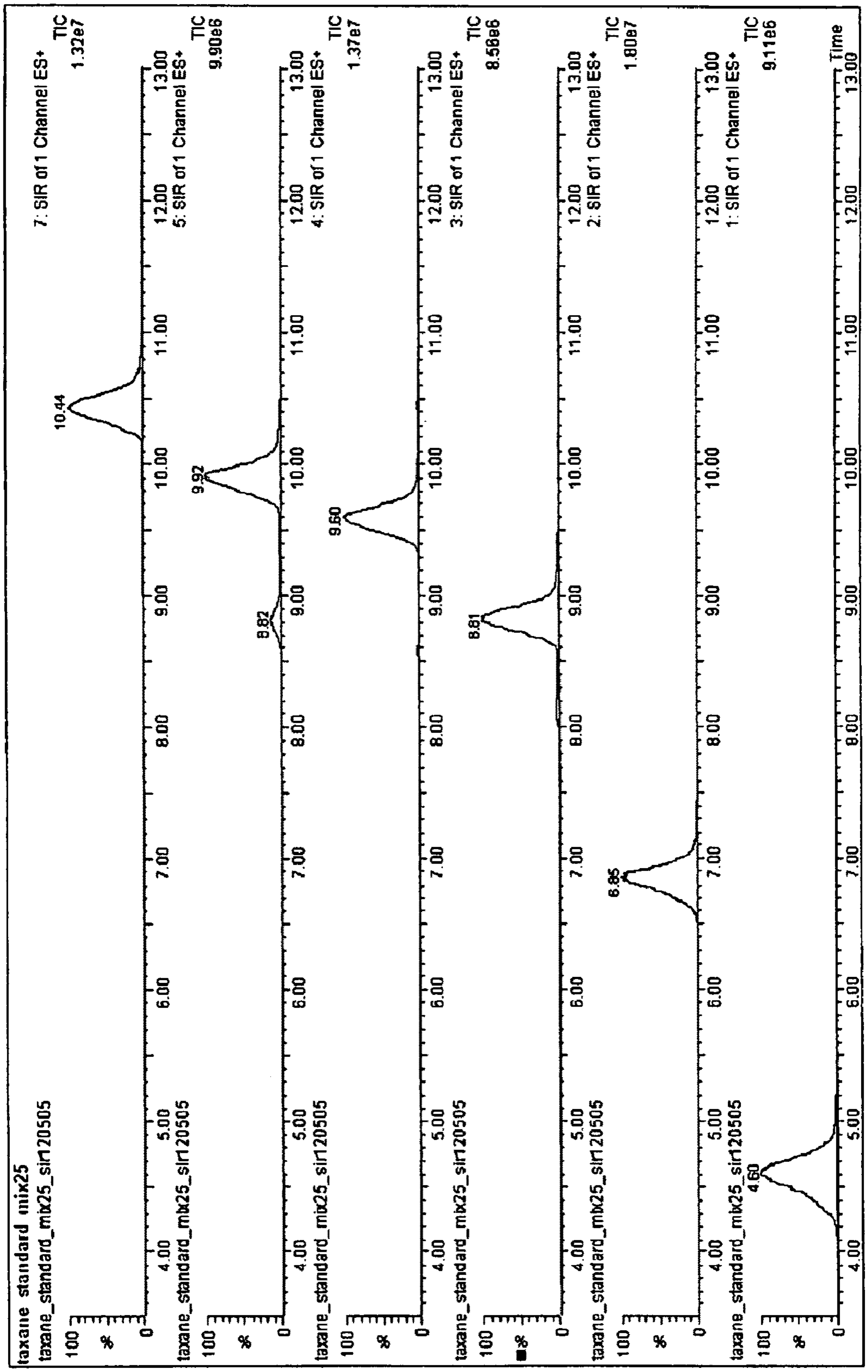
FIG. 8 is the chromatogram of six control taxanes being monitored by SIR mass spectrophotometric method. From top to bottom, the spectra shown are: taxol C (MW 848); paclitaxel (MW 854); cephalomannine (MW 832); 10-deacetyltaxol (MW 810); baccatin (MW 587); and 10-dedeacetylbaccatin III (MW 545).

An injection of six calibration standards (dilutions of 0.5, 1, 2.5, 5, 10 and 25 μg/ml of 13-mix taxanes standard from Hauser, Inc., Boulder, Colo.) at the beginning of each LC/MS run can be used as the basis for quantification of the six target compounds. An exemplary chromatogram of the control taxanes quantified by this method is shown in FIG. 8. Peak area of compound chromatogram is calculated and reported as an amount in μg/ml. This value is then multiplied by the extract volume (0.5 ml) and divided by fresh weight of the tissue to give a compound amount in μg/g fresh weight.

This disclosure describes the discovery of methods for transforming *Taxus* plants, cells and cell lines produced thereby, and related methods and compositions useful for exploiting this discovery. It will be apparent that the precise details of the methods described may be varied or modified without departing from the spirit of the described invention. We claim all such modifications and variations that fall within the scope and spirit of the disclosure and the claims below.

The invention claimed is:

1. A method for producing stably transformed *Taxus* cells, comprising:

(i) introducing into cells of explant tissue from a target *Taxus* plant to be transformed, a vector containing a selectable marker gene operably linked to a plant-compatible promoter and at least one DNA sequence operably linked to regulatory elements effective to allow expression of the sequence in plant cells, wherein the regulatory elements include a cherry 29 thaumatin-like gene (CH29) promoter contained in SEQ ID NO:12;

(ii) culturing said tissue from (i) to form callus in selection medium having a threshold concentration of selective agent effective to discriminate between plant cells transformed with the vector and non-transformed cells, based on their ability to grow in the medium;

(iii) selecting calli based on their growth characteristics in the selection medium;

(iv) subculturing the selected calli in the presence of a selective agent whose concentration is effective to discriminate between transformed and non-transformed plant cells, based on the cells' ability to grow in medium comprising said selective agent;

(v) selecting transformed calli generated in (iv); and (vi) repeating steps (iv) and (v) at least one time, until stably transformed calli are obtained.

2. The method of claim 1, where callus selected in step (vi) is determined to be stably transformed by dividing callus, subculturing pieces thereof, and verifying that the growth of all subcultured calli pieces is resistant to the highest concentration of selective agent used in steps (ii) through (vi).

3. The method of claim 1, where said selectable marker gene is NPTII.

4. The method of claim 1, where said plant is a *Taxus* media plant.

5. The method of claim 4, wherein said explant is a bark peel explant or a peeled stem explant.

6. The method of claim 4, where said selective agent is geneticin.

7. The method of claim 1, wherein said plant is a *Taxus media* 'Hicksii' plant.

8. The method of claim 1, where said DNA sequence operably linked to regulatory elements effective to allow expression of the sequence in plant cells encodes β-D-glucuronidase (GUS).

9. The method of claim 1, where said DNA sequence operably linked to regulatory elements effective to allow expression of the sequence in plant cells encodes an enzyme of the paclitaxel biosynthesis pathway or a transcription factor that regulates the paclitaxel biosyntehsis pathway.

10. The method of claim 9, wherein the DNA sequence operably linked to regulatory elements effective to allow expression of the sequence in plant cells encodes an enzyme selected from the group consisting of deoxyxylulose phosphate synthase (DXS), deoxyxylulose phosphate reductoisomerase (DXR), geranylgeranyldiphosphate synthase (GGDPS), Taxadiene synthase (TDS), Taxadienol acetyl transferase (TAX1), Taxane-2-alpha-O-benzoyltransferase (TAX2), 10-DABIII-10-O-acetyltransferase (TAX6), phenylpropanyltransferase (TAX7), benzoyltransferase (TAX10), 10-beta-hydroxylase, 13-alpha-hydroxylase, Taxoid-14-beta-hydroxylase and 5-alpha-hydroxylase.

11. The method of claim 1, wherein the CH29 promoter includes positions 1-1252 of SEQ ID NO: 12.

12. The method of claim 1, which further comprises growing stably transformed callus of step (vi) to produce a cell culture useful for the manufacture of paclitaxel.

13. The method of claim 7, where said selective agent is kanamycin.

14. The method of claim 7, where said selectable marker gene is NPTII.

15. The method of claim 1, where said explant tissue is selected from the group consisting of needles, stem, and bark peel.

16. The method of claim 1, where said selective agent is selected from the group consisting of geneticin and kanamycin.

17. The method of claim 1, where subculturing in each repeat cycle of steps (iv) and (v) is carried out at a successively higher concentration of the selection agent.

18. A method of expression of a heterologous gene with a regulatory sequence in a *Taxus* plant cell, comprising:

introducing into cells of a *Taxus* plant a nucleic acid construct comprising an expression vector containing a selectable marker gene operably linked to a plant-compatible promoter under conditions effective to stably incorporate into the *Taxus* genome; and culturing said *Taxus* plant cell in a culturing medium containing a selection agent that is metabolized by the expressed product of the selectable marker gene under the regulation of a CH29 promoter contained in SEQ ID NO: 12.

19. The method of claim 18, wherein the CH29 promoter includes positions 1-1252 of SEQ ID NO: 12.

* * * * *

SEQUENCE LISTING

```
<160> NUMBER OF SEQ ID NOS: 69

<210> SEQ ID NO 1
<211> LENGTH: 18
```

<212> TYPE: DNA
<213> ORGANISM: Artificial sequence
<220> FEATURE:
<223> OTHER INFORMATION: Synthetic sequence: primer

<400> SEQUENCE: 1
tgctgctttc gtctctca 18

<210> SEQ ID NO 2
<211> LENGTH: 17
<212> TYPE: DNA
<213> ORGANISM: Artificial sequence
<220> FEATURE:
<223> OTHER INFORMATION: Synthetic sequence: primer

<400> SEQUENCE: 2
gacttcgcgc tgatacc 17

<210> SEQ ID NO 3
<211> LENGTH: 24
<212> TYPE: DNA
<213> ORGANISM: Artificial sequence
<220> FEATURE:
<223> OTHER INFORMATION: Synthetic sequence: primer

<400> SEQUENCE: 3
gtgtaagcta ttttctttga agta 24

<210> SEQ ID NO 4
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 4
gccaacgcta tgtcctga 18

<210> SEQ ID NO 5
<211> LENGTH: 21
<212> TYPE: DNA
<213> ORGANISM: Artificial sequence
<220> FEATURE:
<223> OTHER INFORMATION: Synthetic sequence: primer

<400> SEQUENCE: 5
gtgacaatgg aactggaatg g 21

<210> SEQ ID NO 6
<211> LENGTH: 20
<212> TYPE: DNA
<213> ORGANISM: Artificial sequence
<220> FEATURE:
<223> OTHER INFORMATION: Synthetic sequence: primer

<400> SEQUENCE: 6
agacggagga tagcgtgagg 20

<210> SEQ ID NO 7
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 7
agatatcagt ccgtctgc 18

<210> SEQ ID NO 8
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 8
cgtaaggaag attgatcc 18

<210> SEQ ID NO 9
<211> LENGTH: 549
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(522)
<223> OTHER INFORMATION: Vector sequence
<220> FEATURE:
<221> NAME/KEY: TATA_signal
<222> LOCATION: (418)..(424)
<220> FEATURE:
<221> NAME/KEY: misc_feature
<222> LOCATION: (523)..(546)
<223> OTHER INFORMATION: Vector sequence
<220> FEATURE:
<221> NAME/KEY: misc_feature
<222> LOCATION: (547)..(549)
<223> OTHER INFORMATION: ATG of GUS in constructs; shown e.g. for context

<400> SEQUENCE: 9
gcttggtaac agaaggtaat tatccaagat gtagcatcaa gaatccaatg tttacgggaa 60
aaactatgga agtattatgt gagctcagca agaagcagat caatatgcgg cacatatgca 120
acctatgttc aaaaatgaag aatgtacaga tacaagatcc tatactgcca gaatacgaag 180
aagaatacgt agaaattgaa aaagaagaac caggcgaaga aaagaatctt gaagacgtaa 240
gcactgacga caacaatgaa aagaagaaga taaggtcggt gattgtgaaa gagacataga 300
ggacacatgt aaggtggaaa atgtaagggc ggaaagtaac cttatcacaa aggaatctta 360
tcccccacta cttatccttt tatatttttc cgtgtcattt ttgcccttga gttttcctat 420
ataaggaacc aagttcggca tttgtgaaaa caagaaaaaa tttggtgtaa gctattttct 480
ttgaagtact gaggatacaa cttcagagaa atttgtaagt tttgatcccc gggtggtcag 540
tcccttatg 549

<210> SEQ ID NO 10
<211> LENGTH: 487
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(484)
<220> FEATURE:
<221> NAME/KEY: TATA_signal
<222> LOCATION: (390)..(396)
<220> FEATURE:
<221> NAME/KEY: misc_feature
<222> LOCATION: (485)..(487)
<223> OTHER INFORMATION: ATG of GUS in constructs; shown e.g. for context

<400> SEQUENCE: 10

-continued aagctttggt gtatcgagat tggttatgaa attcagatgc tagtgtaatg tattggtaat 60
ttgggaagat ataataggaa gcaaggctat ttatccattt ctgaaaaggc gaaatggcgt 120
caccgcgagc gtcacgcgca ttccgttctt gctgtaaagc gttgtttggt acacttttga 180
ctagcgaggc ttggcgtgtc agcgtatcta ttcaaaagtc gttaatggct gcggatcaag 240
aaaaagttgg aatagaaaca gaatacccgc gaaattcagg cccggttgcc atgtcctaca 300
cgccgaaata aacgaccaaa ttagtagaaa aataaaaact gactcggata cttacgtcac 360
gtcttgcgca ctgatttgaa aaatctcaat ataaacaaag acggccacaa gaaaaaacca 420
aaacaccgat attcattaat cttatctagt ttctcaaaaa aattcatatc ttccacacgt 480
gaccatg 487

<210> SEQ ID NO 11
<211> LENGTH: 2408
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(2405)
<220> FEATURE:
<221> NAME/KEY: misc_feature
<222> LOCATION: (1186)..(1186)
<223> OTHER INFORMATION: n is a, c, g, or t
<220> FEATURE:
<221> NAME/KEY: TATA_signal
<222> LOCATION: (2329)..(2336)
<220> FEATURE:
<221> NAME/KEY: misc_feature
<222> LOCATION: (2406)..(2408)
<223> OTHER INFORMATION: ATG of GUS in constructs; shown e.g. for
      context

<400> SEQUENCE: 11
agtactttgg ttttttgtc ttagtttcaa aataacaatc aactttgaca tcgataaatg 60
catgttgatt tggtaattgt gtttttgttc caagtgcaag aaatagcaat gtacttttgg 120
tatatcttgt atttaagtgc aagaaatagt aatttacttt tgtagttttt gtttatgttt 180
gataattata cttataaatt tatgtatgtt gttatttatt atgtagttag aaaatttccg 240
agcaatgttc aacgacccga catgtaggga ggagctttat acgtttttc aatcggagaa 300 atatcaatga ggaaacgatg ggaacagaga tggttcgtcg gataattaat ttatgttttg 360
tatgttacat gtgtcgtgac actttgctac ttgttagaat tgtaacattt tggttgttta 420
ttttggtatt aaattaatta taatagtatt tggtatctaa tgggatgtta ttatataatt 480
ttttatgcat ttaatatcat tatgtatcgg tttttttgca cccaaaatcg tagattaaca 540
aaaataaaaa atgaaaaccg ttattaccgg ttgcatgaag tattaccggc gaaaagagca 600
ttagcggcga catgaagtat taccggtgac aatagcatta gcgacggcaa ttgtcttcac 660
atttgacatt ctgataaata acgacaaagt agtagcgacg actttttatc tgtgatgtgt 720
cgcacctatt tcctttaccg acggcttttc cactctttag cgacgacttt tgtcgacgca 780
aattatcatt tttcttatag tgggagacaa atgctaacca ttaaaggtct gttacattta 840
gggactaaaa cacaataaaa ccacacttgt gaataatcca aaacattatg agagtttttt 900
ctaggaattt tttcattata aatataagat taatttattt ttatatataa catatatata 960
atcatataag ttgtcagtct atatttgttt ggaatctata aaacctatca aattattaaa 1020
aaaaaaaaaa aaaaaaactc tgcaacaaaa taaatttaat aaacaaaact tagcttaaaa 1080
aaatgctcct ccaatgattt gtttatttgt cattagatat ttacatgaaa aaactattaa 1140
caaaaactgt aaaagcttct ggtgtgaatg ctccaagaga aacttntgtt aaaacgtgca 1200
ccgaaattat gatgaaaggt acatacacct tcgtaagttt attttatttt agagaccaag 1260
ccattttgtt ttatgtgctt aatataaaaa aaatatacca aaacaaaata gtacattaca 1320
ctattaatca tctatatgct taaaatgaga tcaatattaa acattagatg ttagttttat 1380
atttcagttt ataataattt ttaaaaaact ttaaaaaatt gtggtggaat tttttccatt 1440
ggaatccatg agatgtcgtt ggttttcatt tttctaatat ttcatagttg gtatatattt 1500
gatataaaat aattttttt atttatgtgc ttttcttatt ttatataaaa atattagtta 1560
aaatataaat aaagaatctg gctcaaaaga ttatggataa catcatatca atgataggtt 1620
tataatgtga catcttttat gactgattta gtttactcaa gtcttccata gtcaatgttt 1680
cgacacgtcg acatatatag cgcgacattt tattgacagt aggtgtgaga cccatgtatt 1740
atatgagttt atttaaaaaa aattaaatat aaaattttaa caatttaaaa actttaaatt 1800
tataagaaaa ataagaaatt ttttgaatta ttaaaattaa tgagacttta atgcattaga 1860
tacattacat atataaacca tttctaataa ataccttaca tatatattac cttatatatt 1920
aaatgtagat tttaatttaa taaaatcaaa aatacaataa aatgacaagt ggaaaataga 1980
taaatttaaa atttctataa aatgtcatgt gtccaaatga atgagaaaat gacatatggc 2040
aaagtcattt tcatttatta gggtagatta attaaattgt tttctttttt catggattca 2100
ttctcatcat cctattaatt aagtgtattt cgatattcat gtattcttct tccttgtttc 2160
gtcggcagct tttttttca gtcgtaataa ttttcaatta caaaataaac caataacaaa 2220
aattaaagca catgcaaaaa aatggcagta tcctaccaaa catttaaata tgaatttggt 2280
tggagtaaag tgggacatag caataacctt ttccttcata aaaccatcta taaatagaga 2340
ctgcgtaata cactaatttc cacatccctc ttccatatat tttcttttgt attaaacaag 2400
tgaccatg 2408

<210> SEQ ID NO 12
<211> LENGTH: 1256
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1252)
<223> OTHER INFORMATION: Vector sequence
<220> FEATURE:
<221> NAME/KEY: TATA_signal
<222> LOCATION: (1197)..(1203)
<220> FEATURE:
<221> NAME/KEY: misc_feature
<222> LOCATION: (1253)..(1253)
<223> OTHER INFORMATION: Vector sequence
<220> FEATURE:
<221> NAME/KEY: misc_feature
<222> LOCATION: (1254)..(1256)
<223> OTHER INFORMATION: ATG of GUS in constructs; shown e.g. for context

<400> SEQUENCE: 12
ggcaaaagca taagcatgtt gggcattcta taattataat ttcttggatt tgttaggctt 60
atttgtgatt cttgcttatt agaagcggat ttactgtttt gctcgttttc ttaatgaagt 120
cctacccttt tgataaatta aaaaaaaaga aaaaaaaaga gaacaaccgt gttgtacatg 180
gaaattagac ttcaatttcg aattgtctat tcaaacgtaa attgaactgt tccaaagact 240
tcaaataata atattgttca tatgatattg aaaaggacag gaaaactcca cttcaataat 300
cattatttca aacctaacac gtggacaacc catattgggt gacgtggagc acgtgtggcc 360
gttggaccca acacatgaag ccttgctctg ataccatgtt aatcaatatc aaatgaagaa 420
ctatgaaaaa caacttctag agagagagaa tgagatatca gaaatagaga gagagatggt 480
agagaaaata agctttcttt cctaatgaat cagtaattca gaatacacta ctatacgtaa 540
ccatcttaac taactaacca tcacaacctc taatcatatg ccaagtgtca caatcctatc 600
atactctaac agcttcttct cctagagtgg cactttctac attggcgaag gatgtgaatg 660
ttgatctttc ataaaaaacg atttgacaga aaacaagaaa taaacaaata catagaattg 720
aaaaaaaata aatcttcata caaaagcaaa tgaagtaatt tgattttgtt tgtttttttt 780
attcacagaa agaaggatgc aaactcagaa cctcttaagt tgaaaaaagt gccgatcctg 840
gacaagagca gtcagtgcga ctgctctggg tccattatcc aggaggccca aatttttta 900 atttttaatt ttataaagag gtatattgta tttattatat attcttttaa tatattttt 960 taaagtaaca tggtgtgtat caactctttt aagctctaat tgattggaaa tttggaagtt 1020
ttaagtttta agattacatg acatgacata tgtcacattt gaagattaca tgacatgcga 1080
taagttacgt actcaaattc cccaaaaaaa tatcgtaaga ctagtcgtct tgtgacttgt 1140
catcgcagga accatgagtc ctgcaaaaga acaaaacgtt aggcccgcac caaggctata 1200
taactaaagc ccaagctcat caaattcgaa gcaaagcaag ctaagacatt gccatg 1256

<210> SEQ ID NO 13
<211> LENGTH: 2324
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(2321)
<223> OTHER INFORMATION: "N" can be any nulceotide
<220> FEATURE:
<221> NAME/KEY: misc_feature
<222> LOCATION: (884)..(884)
<223> OTHER INFORMATION: "N" can be any nulceotide
<220> FEATURE:
<221> NAME/KEY: misc_feature
<222> LOCATION: (2322)..(2324)
<223> OTHER INFORMATION: ATG of GUS in constructs; shown e.g. for
context

<400> SEQUENCE: 13
ttaattggtt gagattgaac gtaattcaaa ttattctgag cccaaaccct taaaattcta 60
ggcgggttat ctttgtttga attcattttt gacatcccta atgatattgt tcacgtaatt 120
aagttttgtg gaagtgagag agtccaattt tgataagaaa agagtcagaa aacgtaatat 180
tttaaaagtc taaatctttc tacaaataag agcaaattta tttatttttt aatccaataa 240
atattaatgg aggacaaatt caattcactt ggttgtaaaa taaacttaaa ccaataacca 300
aagaactaat aaatcctgaa gtggaattat taaggataaa tgtacataga caatgaagaa 360
ataataggtt cgatgaatta ataataatta aggatgttac aatcatcatg tgccaagtat 420
atacacaata ttctatggga tttataattt cgttacttca cttaactttt gcgtaaataa 480
aacgaattat ctgatatttt ataataaaac agttaattaa gaaccatcat ttttaacaac 540
atagatatat tatttctaat agtttaatga tacttttaaa tcttttaaat tttatgtttc 600
ttttagaaaa taaaaattca aaaaaattaa atatatttac aaaaactaca atcaaacaca 660
acttcatata ttaaaagcaa aatatatttt gaaaatttca agtgtcctaa caaataagac 720

```
aagaggaaaa tgtacgatga gagacataaa gagaactaat aattgaggag tcctataata    780

tataataaag tttattagta aacttaatta ttaaggactc ctaaaatata tgataggaga    840

aaatgaatgg tgagagatat tggaaaactt aataattaag gatnttaaaa tatatggtaa    900

aagataggca aagtatccat tatccccttt taacttgaag tctacctagg cgcatgtgaa    960

aggttgattt tttgtcacgt catatagcta taacgtaaaa aaagaaagta aaatttttaa   1020

ttttttttaa tatatgacat attttaaacg aaatatagga caaaatgtaa atgaatagta   1080

aaggaaacaa agattaatac ttactttgta agaatttaag ataaatttaa aatttaatag   1140

atcaacttta cgttaaagta aacttgggtg ggtcaagacc caactcgatt tctgttcaac   1200

ccattttaat atttctattt tcaacctaac ccgctcattt gataccccta caaatatcat   1260

atttgtgtgt gaaatatttt ttgggctgga gagagaggcc ccgaggggag tggaggggtg   1320

gggtggggag agagagcgag aaagagtgga gagagaaatt tgatatgaaa tcctacatat   1380

attacagatt gtaatgttct aaactataac gatttgtcat aaacacatat catggatttg   1440

tctttttgtg taattttccc aattgtaaat aggacttcgt tatttgaaac ttgaaagtga   1500

agtcacatag attaagtaca aacattaatt aaagaccgtg gtggaatgat aaatatttat   1560

ttatctttaa ttagttattt ttttgggagc tctttattcc aatgtgagac ttttgcgaca   1620

tatattcaaa tttaatcgaa tcacaatatg tattagattg ataaaaaaat aattttttta   1680

caatgttagt tgagactcat aacttactgc ctattggtaa tctatgactc ctaattcctt   1740

aattatttaa atatatcatc ttgatcgtta acaaagtaat ttcgaaagac cacgagtaag   1800

aagacaaacg agaataccaa aaaattcaaa aatttaatgt gatttggtca atcgatctac   1860

gtccataaag gagatgagta atctactata aatatgagag tacaaaatac agagagaaac   1920

aacctcaact aattcactcg gaatacatga gaagttcaca caagtgataa cgtatcaaac   1980

ttgtgaccca cacttttccc tctaaccaaa gctcttaaaa ctatattgtg aatgctgatt   2040

aagttaaacg aaacagtcct aaatcttttc cgtcctatga gaaacaagat taatcaattc   2100

acaatttttt taaaaagaaa aacctgtaag aaatttaggc aaacaaaacc taacacaagt   2160

ttgtttttgt ttttactacc aacaagaaat tcaaatggca aatgtataac gcatcttagc   2220

taattatatg accagattca gattaatata catcttcacc catgcaatcc atttctatat   2280

aaagaaacat acacgaactt gatattatta gagattgagc catg                    2324
```

```
<210> SEQ ID NO 14
<211> LENGTH: 1541
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1529)
<220> FEATURE:
<221> NAME/KEY: TATA_signal
<222> LOCATION: (510)..(515)
<220> FEATURE:
<221> NAME/KEY: Intron
<222> LOCATION: (685)..(1518)
<220> FEATURE:
<221> NAME/KEY: misc_feature
<222> LOCATION: (1530)..(1538)
<220> FEATURE:
<221> NAME/KEY: misc_feature
<222> LOCATION: (1538)..(1541)
<223> OTHER INFORMATION: ATG of GUS in constructs; shown e.g. for
      context

<400> SEQUENCE: 14
```

```
cccgggctgg tagaatggtt ggaatgaaaa aaattatatt ttctcaccgt tcatatttta     60

taaggtggtg aagaaattat tccaattgaa tatttttttt gtaattgtgt ggacataata    120

taaatttatg aatatttatg aattgaagaa aggcaaaggc cacaagaggt gaatgaaagc    180

gatatcataa aaccaaaaaa cacaaattca attttcaaat ttcaaaaaat tgggggctcc    240

aattccaaat tctcagcaag ccgaagccga gcagaagccg aaaataaaga tccaacggtg    300

gagattaaag aaatgaaaaa agaggaaaaa gaaaggaaga agaaaggaag aatggggctg    360

ggaaaggctg tcagccaggt caccctatct tctctggtgg tcgaaatgat tccttctcca    420

aatttctcat ttccttcgca tttgcatttg catttgcatt tcccttcttt ccctctctct    480

ctctctctct ctctctctct ctctctgttt ataaaccccc gtttctcttc ttccctcttc    540

ctcttattct cgtctttcaa ctcacctagg tcgacaacac tcactcctct ctcagccaga    600

ccttcttctt tggagggttg gctctttctt cttcgttcgt tccttccttc cttcattcat    660

tctcctctct ttcatccaag gtttgtttct tccttccctt ttttaccaaa tcttctcact    720

tcccttacat ttttcatctg ggtatcgtt cttttcccaa attatgctgc tttcgtctct    780

catttatcta ctttattgct tttaactcat tttcccttat gcggttcttc aattttggct    840

gatcttgctg tttgttttgg aattctgttt taatcgccct ggatccgagg tttttgttcg    900

tacaatctac ctagattctt tctgtttgtt tgctgatctg aaattttcca tttgggtttt    960

gattgtctgt gcttacggaa ctgagatcta ggatttggag ttgtgtacct ttttatttct   1020

gcatgcaatt ctgtaatcct gcatagctgg atggctttct gttgattagt gcatgctttg   1080

tttaggacga actgacttgg atttttcgtt gtcgatctgt tctatttttt gttttgctgt   1140

tctggttcat gcttggaatg atttagttgc tttgtaaatt gtacactctg cttttgtgtt   1200

agttcacgta gcttctcgat ctgaaattgg atatggttag agtttatggt cagcttgtga   1260

tcttgcatta tgcaaaaatt ggaactttaa tccttttcat ttgtaagatc tttaagatat   1320

ctgattacct ggttgatttt tttgtgtctg gattatttta tttgttttga aagtagtttg   1380

ttggttcttc ctgtattatt tgctgaatcg ggatgatcaa ttatatgacg tgaatttatg   1440

gaatgtaaat gaatggttta agagattgct ttgtgtggct tatttattca atttctattt   1500

ttacatcgtt ttgtgcaggt tttgaaaaaa aagggcccat g                       1541
```

<210> SEQ ID NO 15
<211> LENGTH: 976
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(972)
<223> OTHER INFORMATION: Vector sequence
<220> FEATURE:
<221> NAME/KEY: TATA_signal
<222> LOCATION: (870)..(875)
<220> FEATURE:
<221> NAME/KEY: misc_feature
<222> LOCATION: (973)..(973)
<223> OTHER INFORMATION: Vector sequence
<220> FEATURE:
<221> NAME/KEY: misc_feature
<222> LOCATION: (974)..(976)
<223> OTHER INFORMATION: ATG of GUS in constructs; shown e.g. for context

<400> SEQUENCE: 15

```
gatcccaaga ccctcgctct ctatcttcgc aacaactcac gtcattgtta ttggttccct     60
```

-continued

```
ttttgccttc atctcaaatg tctcatattg tataatcttc aagaagggta ttcacgacct    120

cctacgatga aggagtgcac cctcgtctgc tttcgtttct tatcattgct tcgttaggga    180

aacataataa ctcgggaagg agacacaaac aatgtttata gtgatgagtc atgtaaggaa    240

ggagagaaga aagttgtgtc gtgattgcct ccttcccctt aacctttgtt ggatgaaaaa    300

gatcattagg actcgaaatt ttaaaggtgg agaaggagac ccaagatacc ctcctcatag    360

caagataaga gatatccgag atgaatgtga ggaagaaaac gatagcaaac gatgtaagtt    420

atcatgaaaa taaagagaaa atatgagaac ctcatgatga ggctttagtg tcacctcgat    480

aattaaagac gaggataaca acgtgacaac aataacaaac aagggacata aacgataaag    540

gcgttgattg acgagaccaa agtcgaacat aataatattt ttttaagata aaaaaaaaag    600

taaaaggatg tattttagaa gaaaagaaat aaaagattat aatttttttg agaatttgtc    660

cgaatacgaa tatatattat tttgaatatt aattaaataa agataccaac gcgtcgcttt    720

ggttcatcgt ctttctttaa cgcggcggac gggaacgtga ggcggacaaa ggtttcatga    780

ttcctagtgg cgtctttatg atttccactc tgatgctgat ggaaacgtga gcggcgaaag    840

aagcgccaca attgatcgaa gcgctcctct ataaatggcg agtaccggga gggagcctca    900

agcagtgcct tgtcccggtt gattcgagtc ccgtcctccg atttcgtgca agaagagaag    960

ggaatcgagc gccatg                                                    976
```

```
<210> SEQ ID NO 16
<211> LENGTH: 1901
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1889)
<223> OTHER INFORMATION: Vector sequence
<220> FEATURE:
<221> NAME/KEY: misc_feature
<222> LOCATION: (869)..(870)
<223> OTHER INFORMATION: division between thioredoxin (1-869) and melon
      actin (870 onwards) promoters in hybrid promoter
<220> FEATURE:
<221> NAME/KEY: TATA_signal
<222> LOCATION: (870)..(875)
<220> FEATURE:
<221> NAME/KEY: Intron
<222> LOCATION: (1045)..(1878)
<220> FEATURE:
<221> NAME/KEY: misc_feature
<222> LOCATION: (1890)..(1898)
<223> OTHER INFORMATION: Vector sequence
<220> FEATURE:
<221> NAME/KEY: misc_feature
<222> LOCATION: (1899)..(1901)
<223> OTHER INFORMATION: ATG of GUS in constructs; shown e.g. for
      context

<400> SEQUENCE: 16
```

```
gatcccaaga ccctcgctct ctatcttcgc aacaactcac gtcattgtta ttggttccct     60

ttttgccttc gtctcaaatg tctcatattg tataatcttc aagaagggta ttcacgacct    120

cctacgatga aggagtgcac cctcgtctgc tttcgtttct tatcattgct tcgttaggga    180

aacataataa ctcgggaagg agacgcaaac aatgtttata gtgatgagtc atgtaaggaa    240

ggagagaaga aagttgtgtc gtgattgcct ccttcccctt aacctttgtt ggatgaaaaa    300

gatcattagg actcgaaatt ttaaaaggtg gagaaggaga cccaagatac cctcctcata    360

gcaagataag agatatccga gatgaatgtg aggaagaaaa cgatagcaaa cgatgtaagt    420
```

```
tatcatgaaa ataaagagaa aatatgagaa cctcatgatg aggctttagt gtcacctcga    480

taattaaaga cgaggataac aacgtgacaa caataacaaa caagggacat aaacgataaa    540

ggcgttgatt gacgagacca aagtcgaaca taataatatt tttttaagat aaaaaaaaag    600

taaaaggatg tattttagaa gaaaagaaat agaagattat aattttttttg agaatttgtc   660

cgaatacgaa tatatattat tttgaatatt aattaaataa agataccaac gcgtcgcttt    720

ggttcatcgt ctttctttaa cgcggcggac gggaacgtga ggcggacaaa ggtttcatga    780

ttcctagtgg cgtctttatg atttccactc tgatgctgat ggaaacgtga gcggcgaaag    840

aagcgccaca attgatcgaa gcgctcctct ataaaccccc gtttctcttc ttccctcttc    900

ctcttattct cgtctttcaa ctcacctagg tcgacaacac tcactcctct ctcagccaga    960

ccttcttctt tggagggttg gctctttctt cttcgttcgt tccttccttc cttccttcat   1020

tctcctctct ttcatccaag gtttgtttct tccttccctt ttttaccaaa tcttctcact   1080

tcccttacat ttttcatctg gggtatcgtt cttttcccaa attatgctgc tttcgtctct   1140

catttatcta ctttattgct tttaactcat tttcccttat gcggttcttc aattttggct   1200

gatcttgctg tttgttttgg aattctgttt taatcgccct ggatccgagg tttttgttcg   1260

tacaatctac ctagattctt tctgtttgtt tgctgatctg aaattttcca tttgggtttt   1320

gattgtctgt gcttacggaa ctgagatcta ggatttggag ttgtgtacct ttttatttct   1380

gcatgcaatt ctgtaatcct gcatagctgg atggctttct gttgattagt gcatgctttg   1440

tttaggacga actgacttgg atttttcgtt gtcgatctgt tctatttttt gttttgctgt   1500

tctggttcat gcttggaatg atttagttgc tttgtaaatt gtacactctg cttttgtgtt   1560

agttcacgta gcttctcgat ctgaaattgg atatggttag agtttatggt cagcttgtga   1620

tcttgcatta tgcaaaaatt ggaactttaa tccttttcat ttgtaagatc tttaagatat   1680

ctgattacct ggttgatttt tttgtgtctg gattatttta tttgttttga aagtagtttg   1740

ttggttcttc ctgtattatt tgctgaatcg ggatgatcaa ttatatgacg tgaatttatg   1800

gaatgtaaat gaatggttta agagattgct ttgtgtggct tatttattca atttctattt   1860

ttacatcgtt ttgtgcaggt tttgaaaaaa aagggcccat g                        1901
```

<210> SEQ ID NO 17
<211> LENGTH: 981
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(978)
<220> FEATURE:
<221> NAME/KEY: TATA_signal
<222> LOCATION: (689)..(694)
<220> FEATURE:
<221> NAME/KEY: misc_feature
<222> LOCATION: (979)..(981)
<223> OTHER INFORMATION: ATG of GUS in constructs; shown e.g. for context

<400> SEQUENCE: 17

```
ctttagatct catgggcgat gtggggatgt cacaatttgg gtaagataat gacaagatca     60

aattaaaact gtcaaatttt aggcaaattt gaaaaacaat tacaaaatct taaggaaagt    120

ataacattag tgcttttttt ttgttccaag aagcattaac atacaatttg ttatgatata    180

ttaatatgca gtgattttaa acattaatgc attttttttt cattaacccc tcccttcaaa    240
```

-continued

```
tatgcataga atttaatgta tacattaaaa ctttaattag gggtgtttta ggcatctaaa    300

aaaatgcaaa atgtgtaaag gcaaatagaa ttaatgactt tgcttatgtg gagcgtagtc    360

attaggtttt atttagataa aaagactatg tcgggtttta tgtaaagaaa cttgagtttc    420

aagagctaaa gtcatatttt cagtagaaat taaacacatt aatcaacact tgagtaataa    480

aatgatcatc aacaatctaa tcatttggtt tacaaattga gaaatactaa ggagactgtt    540

tcaaagtaag acttcctatg aactctctat cacctcatat tcttggcaca aaattttata    600

acattaacat aagaattgta tcaaaaacat aaaatgacag aaaattcgta gaaaatcaca    660

ttcaagataa tagccttagc aattccctta taaactttgt catctaacat ttccctctct    720

attcactctc ctcacactca aacacacacc gtggactggt tcatgcttgc cacttgtacc    780

tcccaagagg ttctagaccc ttcatatcct atcctcttcc cacgtgtcca tcttcaattt    840

tacatatacg tcaccctcct ccttaaataa ccactctctt cacttccatc ttctgacttg    900

caaacgctaa acccccaaat caccccatct tatcatcttc tctctctctc cctctctctc    960

cttctctcgc atcaatccat g                                              981
```

```
<210> SEQ ID NO 18
<211> LENGTH: 2059
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(2047)
<223> OTHER INFORMATION: Vector sequence
<220> FEATURE:
<221> NAME/KEY: misc_feature
<222> LOCATION: (1027)..(1028)
<223> OTHER INFORMATION: division between thiamine synthase (1-1027) and
      melon actin (1028 onwards) promoters in hybrid promoter
<220> FEATURE:
<221> NAME/KEY: TATA_signal
<222> LOCATION: (1028)..(1033)
<220> FEATURE:
<221> NAME/KEY: Intron
<222> LOCATION: (1203)..(2036)
<220> FEATURE:
<221> NAME/KEY: misc_feature
<222> LOCATION: (2048)..(2056)
<223> OTHER INFORMATION: Vector sequence
<220> FEATURE:
<221> NAME/KEY: misc_feature
<222> LOCATION: (2057)..(2059)
<223> OTHER INFORMATION: ATG of GUS in constructs; shown e.g. for
      context

<400> SEQUENCE: 18
```

```
aagctttaga tctcatgggc gatgtgggat gtcacaatcc acccccctta ggggcccgac     60

gtcctcgtca tcacacttcc ggccagggat tggctctaat accatttgtc acatcccggc    120

ccggatccac cacatctcaa gcccgttcca ccaccgtagc atgatattgt ccgctttggg    180

cttaccattc cctcacggtt ttgtttttgg gaactcacga gcaacttcct agtgggtcac    240

ccatcctggg agtgtttaac ttcggagttc ctacgaaacc cgaagccaat gagctcccaa    300

aaggtctcgt gctaagtagg gatgagaata tacatttaag gattactccc ctgggcgatg    360

tgggatgtca caatttgggt aagaaaatga caagatcaaa ttaaaactgt caagttttat    420

gcaaatttga aaaacaatta caaaatctta aggaaagtat aacattagtg cttttttttt    480

tgttccaaga agcattaaca tacaatttgt tatgatatat taatatgcaa tgattttaaa    540

cattaatgca tttttttttc attaatccct cccttcaaat atgcatagaa tttaatgtat    600
```

-continued

```
acattaaaac tttaattagg ggtgttttag gcatctaaaa aaatgcaaaa tgtgtaaagg    660

caaatagaat taatgacttt gcttatgtgg agcctagtca ttaggtttta tttagataaa    720

aagactatgt caggttttat gtaaagaaac ttgagtttca agagctaaag tcatattttc    780

agtagaaatt aaacacatta atcaacactt gagtaataaa atgatcatca acaatctaat    840

catttggttt acaaattgag aaatactaag gagactgttt caaagtaaga cttcctatga    900

actctctatc acctcatatt cttggcacaa aattttataa cattaacata agaattgtat    960

caacaacata aaatggcaga aagttcgtag aaaatcacat tcaagataat agccttagca   1020

attcccttat aaacccccgt ttctcttctt ccctcttcct cttattctcg tctttcaact   1080

cacctaggtc gacaacactc actcctctct cagccagacc ttcttctttg gagggttggc   1140

tctttcttct tcgttcgttc cttccttcct tcattcattc tcctctcttt catccaaggt   1200

ttgtttcttc cttccctttt ttaccaaatc ttctcacttc ccttacattt ttcatctggg   1260

gtatcgttct tttcccaaat tatgctgctt tcgtctctca tttatctact ttattgcttt   1320

taactcattt tcccttatgc ggttcttcaa ttttggctga tcttgctgtt tgttttggaa   1380

ttctgtttta atcgccctgg atccgaggtt tttgttcgta caatctacct agattctttc   1440

tgtttgtttg ctgatctgaa attttccatt tgggttttga ttgtctgtgc ttacggaact   1500

gagatctagg atttggagtt gtgtaccttt ttatttctgc atgcaattct gtaatcctgc   1560

atagctggat ggctttctgt tgattagtgc atgctttgtt taggacgaac tgacttggat   1620

ttttcgttgt cgatctgttc tattttttgt tttgctgttc tggttcatgc ttggaatgat   1680

ttagttgctt tgtaaattgt acactctgct tttgtgttag ttcacgtagc ttctcgatct   1740

gaaattggat atggttagag tttatggtca gcttgtgatc ttgcattatg caaaaattgg   1800

aactttaatc cttttcattt gtaagatctt taagatatct gattacctgg ttgatttttt   1860

tgtgtctgga ttattttatt tgttttgaaa gtagtttgtt ggttcttcct gtattatttg   1920

ctgaatcggg atgatcaatt atatgacgtg aatttatgga atgtaaatga atggtttaag   1980

agattgcttt gtgtggctta tttattcaat ttctattttt acatcgtttt gtgcaggttt   2040

tgaaaaaaaa gggcccatg                                                2059
```

```
<210> SEQ ID NO 19
<211> LENGTH: 1662
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1659)
<220> FEATURE:
<221> NAME/KEY: TATA_signal
<222> LOCATION: (1585)..(1590)
<220> FEATURE:
<221> NAME/KEY: misc_feature
<222> LOCATION: (1660)..(1662)
<223> OTHER INFORMATION: ATG of GUS in constructs; shown e.g. for
      context

<400> SEQUENCE: 19

agcttggtac cgagctcgga tccactagta acggccgcca gtgtgctgga attcggcttg     60

taatacgact cactataggg cacgcgtggt ccacggcccg ggctggtaac tagaagctaa    120

aggacgacgt caacataatt aaaattactc caagataatt aaaattaaaa atatcttata    180

ttttatggcg ttacatcttc ctttcctctt cttctttttt ctgctgcgat ttcttcccat    240

ctatttcttc ttttactctt atttttttct ttacattgtt tagatttggg taaccaaatc    300
```

tgatttcttt ctatcgtctt tcttcttttt ctcttttttt ttccgctgcg atttcttccc 360
attgtctatc gtttttttcct cttttttttt ttacatcgta accaaatcta aaagatcgta 420
tataaagaat cttcaaaaaa aaaaattgtt tagattggag tagccaaatt taaacaatcg 480
cgtaaaaaaa ataaacgatc gtagacaaat ctaaacgatc gtgcacaaaa agatttaaaa 540
aaatcgttta gtcaaatcta aacaattgta taaccaaatt aaacgataga attgaaataa 600
taaatcggtt agatttggct atccaaattt aaatgaccaa atctaaacga tcgtatacca 660
aatctaaacg atcgtatacc aaatctaaat gatcatgtac caaatatatt atgcacattg 720
ttggcagggt ggttgacgga acattttgta tattttctat tatgggtttg tagaattttt 780
tcattttcga aattgttcta tacaatataa atataaatat tttaccactt cgttatattt 840
tcgaaaagac cccttaaata aattgaattc gcatataatt aaaatttttt cccaaaaaaa 900
gtagactatg tctatctaaa aatttgattc ccaatataga acaaattctc aaaatgaaca 960
aacatttgaa attctcgata tagaaaacat ttacttattt tgaattggga catattccaa 1020
agtttattcc aaacgtaact ttgaaggaaa agttgattga gattacatcc atatttttgt 1080
ttttcatatt gaatttcatg gaaaattaaa atgcacacaa aatgatgtat gagattaaac 1140
caaagtttat cgttattgaa ttcttttatt aaaaaaccaa caaaatttta aaacttgttt 1200
gcaatagacc aatatagtta atccatcgtg gtctattgta gataaattgt aatattttgt 1260
tatatttaat aaatattttg atttattttg atatatttgt atttagataa caaaattaag 1320
atttaaatat tattttatat cttaatataa acatttgtta attttttcta ttttagacca 1380
tttctcttat ttttatataa cattttaata actaaatgat gtgacacaca ctaatattat 1440
ttttatccaa agaaaataat gctataaaat atgggtcttc tttatcacct tcatgataat 1500
tatgaaaaat aaaataaaat ttaattatat aattcatttc atctaatcgt acaagctaga 1560
tattactata tcaacaactt tgtgtataaa aagggcaaga aattaagcat tatcgtgtga 1620
gccacttttt ctatatctag agatagaagg tttaaaacca tg 1662

<210> SEQ ID NO 20
<211> LENGTH: 1379
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1352)
<223> OTHER INFORMATION: Vector sequence
<220> FEATURE:
<221> NAME/KEY: TATA_signal
<222> LOCATION: (1232)..(1238)
<220> FEATURE:
<221> NAME/KEY: misc_feature
<222> LOCATION: (1353)..(1376)
<223> OTHER INFORMATION: Vector sequence
<220> FEATURE:
<221> NAME/KEY: misc_feature
<222> LOCATION: (1377)..(1379)
<223> OTHER INFORMATION: ATG of GUS in constructs; shown e.g. for
context

<400> SEQUENCE: 20
gggctggtaa ctttaagaga aattggtaaa attcctagag agaattgtaa ttaatatagg 60
agaatgattt taattctaat gttgtatcca ttttcgataa agttaaataa agtgtcgtag 120
acgaccatca ttcttaatcc atttgtactt atcaaatttg tatctgagat ttaagttcaa 180
attcacacta aaacaatcga aatgtatgcg acaatcacaa tggaaaatac gtatgatgta 240

```
ttccatcacc tttcaagttc taacctagga tatgttttgg aatatttgag atttattaaa    300

ttattctttt atccgttgac agtttatttt ttgtttaacg atgtatgtaa gaaacgacga    360

aatatgtgat taaaccaaga tcgcatacaa ataagagcta gatcctaaag atatataaaa    420

gtatgatcaa caacgtacaa aacgtttctt ttcgatgata attatcttaa gaacttcaag    480

gttaatttag atctcttaat taaaaaattt catagataat gcatccgtga acaagaaaaa    540

acataaagaa cccatggttg tcctaatttt tgtagtaaat aagcgtagtt caagacacaa    600

gtaagaatga cgttaccaca tgttaatcta gattccaaaa cttgagcttg agagcacgtt    660

acgaaaataa tctacgaaaa cgagtaagtc gtctaagttc gttttcgttt atttgacacg    720

taagatactc gtattgaaag aagacgaaaa atggaaaaaa gtaaagaagg taaggaggtg    780

ggtgagtcca aaggaaacat accaaattca tgcaagaact atgagattca gaaattaaga    840

gaaaagtgtg gaaatcatgt aactaaattt aaaatacata taggtactat tttctttcct    900

tttctattga aacaaagaga ccaaggggga attagggtat atggcattgg cagacataaa    960

aataataaag ttaaatcaaa ttgggtccca aactcaccaa agaggaaatt cagtgttgaa   1020

taaagccaat tagccaaagc caaagccaaa gccacctcct ctctttccca catacatgca   1080

tgaaatttca tgggcccatt ctttttatca tcacattttt aataatttta tcttcttctt   1140

cttcttcttc ttcttcttct tcttcttctt cttcttcttc ttcttttttt aatcaatttc   1200

ttcccacttt ccaatcctaa ataaatttca ctataaatac cccttcatta taacttgatc   1260

caacacaccc accaaccaaa aacaaaacct tgataccaaa gagttctttt ttctttattt   1320

gcacaaacca aatcttgtat ctacaaaaag aaggatcccc gggtggtcag tcccttatg    1379
```

```
<210> SEQ ID NO 21
<211> LENGTH: 1037
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1034)
<220> FEATURE:
<221> NAME/KEY: TATA_signal
<222> LOCATION: (734)..(740)
<220> FEATURE:
<221> NAME/KEY: misc_feature
<222> LOCATION: (1035)..(1037)
<223> OTHER INFORMATION: ATG of GUS in constructs; shown e.g. for
      context

<400> SEQUENCE: 21
```

```
cgccgtcgct gaactcgatc cgtggcgcag tcgaatgcca gacccaactc aaaaccgagt     60

ttttccattt ttaatttttt aagtttttaa ttatataaaa atattttttt aattatttac    120

atacttttag tttcacatgg taatgtttaa ttagatttgt gggacccatt tatgtgtcac    180

gtcagcccgt aacagaattt tttacgaaat tatcacattg atttgcgaca tctattttca    240

gagactacat tgattggttt ttaattttat aaaccatctt aatgaagtat gtcaatttta    300

aagatcattt attacaaaaa ccctttattt aattttatat tgaaatacta aaatatgata    360

aaatgtactc gaatagttta gtagataggg tggtgttatt tagatactta ttattttatt    420

tttatacata ctcttcttaa tttctaatca gaaaattgaa ttaataaaaa aatatcaatg    480

aaaaataatt taacaaaaat gtacaaaaat acagaatgaa cgtggaaata gcactatacc    540

ctagtagata ttggataaaa tatattatgg gtttaaaatt gaaaaaatat atgtggtttc    600
```

```
gagccatacg ggcccgggaa tgaccgactg ttgcagtgcc tctggccaat cccaactcga    660

caacgttttt gacgaaacca ctctggtttt ccaaccccac ccatttcact cttacagcgg    720

ttttgaaata tcctataaat atatcataca aatacaacag agaaattttt ttttttgtca    780

aaatatacaa cagagaattg agtcactcat atatagacag agaaggagag agaccagacc    840

cctaccttag agagagagag agagcagaag ccatctgtgt gtcaactggt tctttctctc    900

ccatttttct tggtttcttg gtgggatttc tggtttctct aaactaagag atcagttcag    960

caggaacaac cgtatatata ttactaggat tattaattat ttatttataa taataaataa   1020

ttgttagaga gaccatg                                                  1037


<210> SEQ ID NO 22
<211> LENGTH: 982
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(951)
<223> OTHER INFORMATION: Vector sequence
<220> FEATURE:
<221> NAME/KEY: TATA_signal
<222> LOCATION: (908)..(914)
<220> FEATURE:
<221> NAME/KEY: misc_feature
<222> LOCATION: (952)..(979)
<223> OTHER INFORMATION: Vector sequence
<220> FEATURE:
<221> NAME/KEY: misc_feature
<222> LOCATION: (980)..(982)
<223> OTHER INFORMATION: ATG of GUS in constructs; shown e.g. for
      context

<400> SEQUENCE: 22

aagcttaatt gagatgatta gcccagaccc agcaggatta ggcttaatgg tggtccattt     60

gagaaaaaga ttaaaaatga tgtcataaaa aaacgtggtc gbcaggattc gaacctgcgc    120

gggcaaagcc cacatgattt ctagtcatgc ccgataacca ctccggcacg accacaatga    180

tgctacaatt gctttgttgt aatcattaac ttatggttga gtttgatgct gattaatact    240

attatgtttc cattaactac ttttgaagta tacaaaatta cgaatttata accaaatttg    300

aggtataata tgcgagagct acctaaattt ttcttactta attttaaagt acattcaaat    360

tctgaattta tattgtgtat agtcagaaaa caatctacat atttaaacac ataaatttct    420

cacgtttata atcaatttg tcggttcctg taatttttct aaaataaaaa gcaaccaaaa    480

ttgtgcatca acttattaca taccatggga aatgcaaact tcaaaactta tggactcaaa    540

gggtacatat ttaaactaca tattgtcaga ttcttcactc ttatttcttg agggcctcga    600

ggcattacca accaaatcca aaaattgctt tcgaatctca ataaaaagga taaccccatg    660

aaaaagacgt ggacggcagg attcgaacct gcgcgggcag agcccacatg atttctagtc    720

atgcccgata accactccgg cacgtccact tcactgttaa cgtttacagt aacaagtcac    780

taactactaa tcaacattag ctcaggaaat caaaactaga ttatttacat ttacaacgac    840

atgtcgttcg aagtagttgg tctgtatctg agtagctttg gcgggtagat tcaatcgcat    900

ttctgcatat aaaactgatc ctccctctat cgccaaagtc aaactgaaaa ggacccaagc    960

tagcttcgac ggatccccca tg                                             982


<210> SEQ ID NO 23
<211> LENGTH: 1262
<212> TYPE: DNA
```

<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(1259)
<220> FEATURE:
<221> NAME/KEY: TATA_signal
<222> LOCATION: (1171)..(1178)
<220> FEATURE:
<221> NAME/KEY: misc_feature
<222> LOCATION: (1260)..(1262)
<223> OTHER INFORMATION: ATG of GUS in constructs; shown e.g. for
      context

<400> SEQUENCE: 23

```
ggcacaagga atgagaagga gatagatgac ttgtgattcg agctcacttg tatcttgtgt     60

ttgagatggt gaagcaacga gcggtgggcg ctggtatttg taggagggaa aatgagttga    120

ggcgtggaca cgtagagttt cgtgtgtaag gcatcttttg ccattcttct acttgcatgg    180

ctttgaggct ttgaattgtt aacacctcat tttgtgtagc aggggcagca ggctatatgc    240

ggcaaccagc ggtggggttc ctcgtcaata ttgttgtctg gttctgagct tgatttgcac    300

ctggccgttt ggtgaagtaa aattcatggg acttgggatc cgaacccggg cccatatgac    360

tgtgcgtgct tggtgagaaa cgtgaactcc acctgattgt ctgtgatgag tttaattggt    420

tttttttgtt taaatgtttg gtcaaatttg ttttactcgg aacaaattgt taagcctctg    480

ctctataaga aataaaaaac gttgttttgt gaactaaaac gcaatctttt ggcttagttg    540

agccaagagg gttctctctc tacagttcca aatccaaaac ccacaacttc aatgaaatta    600

cgaatgaatg acctccacta ccactagtat gaattctttt gtattttcct gtcaagcaaa    660

aaggccaaca agagatcagc tacttagaac aacaaaagca tttcatactt tacaaattga    720

tcctataaaa aacttggaag cttttcttta aaagaaaaaa aggagagaga atattagagt    780

ggtacccaaa ttataataac tcaaatattt acttttacat aaaaggagag agaatatgaa    840

tgaggattgg caacaaaaca atggaaccca ccaaaactga tcagagacga tcagatggag    900

ttcacgtttc tcagcaggca atgccaaaag ggtttcagaa acgcaccaat cccaagacag    960

taagaaaaca acaatggctc gagacaccca cctggttgcc acataactca actcactttg   1020

ttttttctct gaagccgaaa gccacctgcc ctaaaccaca aaatgaggtg taaacaattc   1080

agagcttcaa agccatgcaa gcagaataat ggcgaaggat tccttacact catttcccta   1140

cgtgtctctc cctcacctcc tcttcttcac tataaatacc agcgcctgct gctcgccgct   1200

tcacccatct caaaaccaaa gagctttctc tctcctttct gtagtctcca aatatgtcca   1260

tg                                                                   1262
```

<210> SEQ ID NO 24
<211> LENGTH: 380
<212> TYPE: DNA
<213> ORGANISM: Artificial sequence
<220> FEATURE:
<223> OTHER INFORMATION: Synthetic sequence: promoter
<220> FEATURE:
<221> NAME/KEY: promoter
<222> LOCATION: (1)..(377)
<223> OTHER INFORMATION: ATG of GUS in constructs; shown e.g. for
      context
<220> FEATURE:
<221> NAME/KEY: misc_feature
<222> LOCATION: (378)..(380)
<223> OTHER INFORMATION: ATG of GUS in constructs; shown e.g. for
      context

<400> SEQUENCE: 24
aagcttagaa attaggttaa aagagacaaa aaacttctta gaaactttac ctgaggagtt 60
taagtcaaat cgatactttg acaaagaaaa tgagttagga agatacccac ctcataatca 120
acctaacact aaggttttag acgatataga atgtatagag caaggaggcc ctaggccaca 180
tgcataccat acatttaacc cacaattaaa taacatatct gacatgttat catatataat 240
aaaaaactgt tgttgcaaaa aacacaagga acatcaggaa acatcacctg aatatcaatc 300
tatacaaaat agactgacaa agctcttaga agaactatct aagaaagaac aatttgataa 360
aaaatccagt aaaatttatg 380

<210> SEQ ID NO 25
<211> LENGTH: 16
<212> TYPE: DNA
<213> ORGANISM: Artificial sequence
<220> FEATURE:
<223> OTHER INFORMATION: Synthetic sequence: promoterless
<220> FEATURE:
<221> NAME/KEY: misc_feature
<222> LOCATION: (14)..(16)
<223> OTHER INFORMATION: ATG of GUS in constructs; shown e.g. for context

<400> SEQUENCE: 25
cgagctcgga tccatg 16

<210> SEQ ID NO 26
<211> LENGTH: 36
<212> TYPE: DNA
<213> ORGANISM: Artificial sequence
<220> FEATURE:
<223> OTHER INFORMATION: Synthetic sequence: primer

<400> SEQUENCE: 26
tcaggactag tgaccatgga tgcccttaag caattg 36

<210> SEQ ID NO 27
<211> LENGTH: 37
<212> TYPE: DNA
<213> ORGANISM: Artificial sequence
<220> FEATURE:
<223> OTHER INFORMATION: Synthetic sequence: primer

<400> SEQUENCE: 27
tacggggtac cttaagatct ggaatagagt ttaatgg 37

<210> SEQ ID NO 28
<211> LENGTH: 37
<212> TYPE: DNA
<213> ORGANISM: Artificial sequence
<220> FEATURE:
<223> OTHER INFORMATION: Synthetic sequence: primer

<400> SEQUENCE: 28
tcaggactag tgaccatggc tcagctctca tttaatg 37

<210> SEQ ID NO 29
<211> LENGTH: 31
<212> TYPE: DNA
<213> ORGANISM: Artificial sequence
<220> FEATURE:
<223> OTHER INFORMATION: Synthetic sequence: primer

<400> SEQUENCE: 29
tacggggtac ctcatacttg aattggatca a 31

<210> SEQ ID NO 30
<211> LENGTH: 22
<212> TYPE: DNA
<213> ORGANISM: Artificial sequence
<220> FEATURE:
<223> OTHER INFORMATION: Synthetic sequence: primer

<400> SEQUENCE: 30
ctctctgttc aagtatgaca gt 22

<210> SEQ ID NO 31
<211> LENGTH: 22
<212> TYPE: DNA
<213> ORGANISM: Artificial sequence
<220> FEATURE:
<223> OTHER INFORMATION: Synthetic sequence: primer

<400> SEQUENCE: 31
gtacagttgt cattagacct tc 22

<210> SEQ ID NO 32
<211> LENGTH: 22
<212> TYPE: DNA
<213> ORGANISM: Artificial sequence
<220> FEATURE:
<223> OTHER INFORMATION: Synthetic sequence: primer

<400> SEQUENCE: 32
tgccgactac cttggtgatc tc 22

<210> SEQ ID NO 33
<211> LENGTH: 16
<212> TYPE: DNA
<213> ORGANISM: Artificial sequence
<220> FEATURE:
<223> OTHER INFORMATION: Synthetic sequence: primer

<400> SEQUENCE: 33
cggcttcccc tggaga 16

<210> SEQ ID NO 34
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 34
gccaacgcta tgtcctga 18

<210> SEQ ID NO 35
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 35
cctgccgaga aagtatcc 18

<210> SEQ ID NO 36
<211> LENGTH: 20
<212> TYPE: DNA
<213> ORGANISM: Artificial sequence
<220> FEATURE:
<223> OTHER INFORMATION: Synthetic sequence: primer

<400> SEQUENCE: 36
gtcctacacg ccgaaataaa 20

<210> SEQ ID NO 37
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 37
aaaccgagtt agtgcagc 18

<210> SEQ ID NO 38
<211> LENGTH: 19
<212> TYPE: DNA
<213> ORGANISM: Artificial sequence
<220> FEATURE:
<223> OTHER INFORMATION: Synthetic sequence: primer

<400> SEQUENCE: 38
gactgatatc tccgtctcc 19

<210> SEQ ID NO 39
<211> LENGTH: 20
<212> TYPE: DNA
<213> ORGANISM: Artificial sequence
<220> FEATURE:
<223> OTHER INFORMATION: Synthetic sequence: primer

<400> SEQUENCE: 39
tggcatgaac ttcggtgaaa 20

<210> SEQ ID NO 40
<211> LENGTH: 20
<212> TYPE: DNA
<213> ORGANISM: Artificial sequence
<220> FEATURE:
<223> OTHER INFORMATION: Synthetic sequence: primer

<400> SEQUENCE: 40
tcgagctcgg tagcaattcc 20

<210> SEQ ID NO 41
<211> LENGTH: 20
<212> TYPE: DNA
<213> ORGANISM: Artificial sequence
<220> FEATURE:
<223> OTHER INFORMATION: Synthetic sequence: primer

<400> SEQUENCE: 41
atcaaggctg ccatcaagga 20

<210> SEQ ID NO 42
<211> LENGTH: 22
<212> TYPE: DNA
<213> ORGANISM: Artificial sequence
<220> FEATURE:
<223> OTHER INFORMATION: Synthetic sequence: primer

<400> SEQUENCE: 42
cttgatcgac tgtctccgat ga 22

<210> SEQ ID NO 43
<211> LENGTH: 37
<212> TYPE: DNA

-continued

<213> ORGANISM: Artificial sequence
<220> FEATURE:
<223> OTHER INFORMATION: Synthetic sequence: primer

<400> SEQUENCE: 43
tcaggactag tgaccatggc tcagctctca tttaatg 37

<210> SEQ ID NO 44
<211> LENGTH: 31
<212> TYPE: DNA
<213> ORGANISM: Artificial sequence
<220> FEATURE:
<223> OTHER INFORMATION: Synthetic sequence: primer

<400> SEQUENCE: 44
tacggggtac ctcatacttg aattggatca a 31

<210> SEQ ID NO 45
<211> LENGTH: 36
<212> TYPE: DNA
<213> ORGANISM: Artificial sequence
<220> FEATURE:
<223> OTHER INFORMATION: Synthetic sequence: primer

<400> SEQUENCE: 45
tcaggactag tgaccatggc ttcagtgact ctaggt 36

<210> SEQ ID NO 46
<211> LENGTH: 35
<212> TYPE: DNA
<213> ORGANISM: Artificial sequence
<220> FEATURE:
<223> OTHER INFORMATION: Synthetic sequence: primer

<400> SEQUENCE: 46
tacggggtac ctcagttctg tctataggca atgta 35

<210> SEQ ID NO 47
<211> LENGTH: 43
<212> TYPE: DNA
<213> ORGANISM: Artificial sequence
<220> FEATURE:
<223> OTHER INFORMATION: Synthetic sequence: primer

<400> SEQUENCE: 47
tcaggactag tgaccatgga ccatggctct aaacttgatg gct 43

<210> SEQ ID NO 48
<211> LENGTH: 34
<212> TYPE: DNA
<213> ORGANISM: Artificial sequence
<220> FEATURE:
<223> OTHER INFORMATION: Synthetic sequence: primer

<400> SEQUENCE: 48
tacggggtac ctcatacaag agcaggactc aaac 34

<210> SEQ ID NO 49
<211> LENGTH: 35
<212> TYPE: DNA
<213> ORGANISM: Artificial sequence
<220> FEATURE:
<223> OTHER INFORMATION: Synthetic sequence: primer

<400> SEQUENCE: 49
tcaggactag tgaccatgga cgccctgtat aagag 35

-continued

<210> SEQ ID NO 50
<211> LENGTH: 35
<212> TYPE: DNA
<213> ORGANISM: Artificial sequence
<220> FEATURE:
<223> OTHER INFORMATION: Synthetic sequence: primer

<400> SEQUENCE: 50
tacggggtac cctatggtct gggaaacagt ttaat 35

<210> SEQ ID NO 51
<211> LENGTH: 36
<212> TYPE: DNA
<213> ORGANISM: Artificial sequence
<220> FEATURE:
<223> OTHER INFORMATION: Synthetic sequence: primer

<400> SEQUENCE: 51
tcaggactag tgaccatgga tgcccttaag caattg 36

<210> SEQ ID NO 52
<211> LENGTH: 37
<212> TYPE: DNA
<213> ORGANISM: Artificial sequence
<220> FEATURE:
<223> OTHER INFORMATION: Synthetic sequence: primer

<400> SEQUENCE: 52
tacggggtac cttaagatct ggaatagagt ttaatgg 37

<210> SEQ ID NO 53
<211> LENGTH: 34
<212> TYPE: DNA
<213> ORGANISM: Artificial sequence
<220> FEATURE:
<223> OTHER INFORMATION: Synthetic sequence: primer

<400> SEQUENCE: 53
tcaggactag tgaccatggg caggttcaat gtag 34

<210> SEQ ID NO 54
<211> LENGTH: 38
<212> TYPE: DNA
<213> ORGANISM: Artificial sequence
<220> FEATURE:
<223> OTHER INFORMATION: Synthetic sequence: primer

<400> SEQUENCE: 54
tacggggtac cttataactt agagttacat attttagc 38

<210> SEQ ID NO 55
<211> LENGTH: 34
<212> TYPE: DNA
<213> ORGANISM: Artificial sequence
<220> FEATURE:
<223> OTHER INFORMATION: Synthetic sequence: primer

<400> SEQUENCE: 55
tcaggactag tgaccatggc atcttcctgt ggag 34

<210> SEQ ID NO 56
<211> LENGTH: 42
<212> TYPE: DNA
<213> ORGANISM: Artificial sequence
<220> FEATURE:
<223> OTHER INFORMATION: Synthetic sequence: primer

<400> SEQUENCE: 56
tacggggtac cttacaaatt attaatcaaa tgaagactgt cc 42

<210> SEQ ID NO 57
<211> LENGTH: 24
<212> TYPE: DNA
<213> ORGANISM: Artificial sequence
<220> FEATURE:
<223> OTHER INFORMATION: Synthetic sequence: primer

<400> SEQUENCE: 57
tgccgaactt ggttccttat atag 24

<210> SEQ ID NO 58
<211> LENGTH: 24
<212> TYPE: DNA
<213> ORGANISM: Artificial sequence
<220> FEATURE:
<223> OTHER INFORMATION: Synthetic sequence: primer

<400> SEQUENCE: 58
aagacgtgac gtaagtatcc gagt 24

<210> SEQ ID NO 59
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 59
ggtccattat ccaggagg 18

<210> SEQ ID NO 60
<211> LENGTH: 19
<212> TYPE: DNA
<213> ORGANISM: Artificial sequence
<220> FEATURE:
<223> OTHER INFORMATION: Synthetic sequence: primer

<400> SEQUENCE: 60
gactgatatc tccgtctcc 19

<210> SEQ ID NO 61
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 61
atggtgtgaa tcatctcg 18

<210> SEQ ID NO 62
<211> LENGTH: 19
<212> TYPE: DNA
<213> ORGANISM: Artificial sequence
<220> FEATURE:
<223> OTHER INFORMATION: Synthetic sequence: primer

<400> SEQUENCE: 62
gcagtcaaaa ttatacgcc 19

<210> SEQ ID NO 63
<211> LENGTH: 18
<212> TYPE: DNA

-continued

<213> ORGANISM: Artificial sequence
<220> FEATURE:
<223> OTHER INFORMATION: Synthetic sequence: primer

<400> SEQUENCE: 63
tcgttggaca gaataagc 18

<210> SEQ ID NO 64
<211> LENGTH: 20
<212> TYPE: DNA
<213> ORGANISM: Artificial sequence
<220> FEATURE:
<223> OTHER INFORMATION: Synthetic sequence: primer

<400> SEQUENCE: 64
gaacagttag aagatggagg 20

<210> SEQ ID NO 65
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 65
aaaccgagtt agtgcacg 18

<210> SEQ ID NO 66
<211> LENGTH: 18
<212> TYPE: DNA
<213> ORGANISM: Artificial sequence
<220> FEATURE:
<223> OTHER INFORMATION: Synthetic sequence: primer

<400> SEQUENCE: 66
gaaaacgtga tgaagtgc 18

<210> SEQ ID NO 67
<211> LENGTH: 19
<212> TYPE: DNA
<213> ORGANISM: Artificial sequence
<220> FEATURE:
<223> OTHER INFORMATION: Synthetic sequence: primer

<400> SEQUENCE: 67
catcagctac atttgaacc 19

<210> SEQ ID NO 68
<211> LENGTH: 19
<212> TYPE: DNA
<213> ORGANISM: Artificial sequence
<220> FEATURE:
<223> OTHER INFORMATION: Synthetic sequence: primer

<400> SEQUENCE: 68
gccaaatgtt tgaacgatc 19

<210> SEQ ID NO 69
<211> LENGTH: 59
<212> TYPE: DNA
<213> ORGANISM: Artificial sequence
<220> FEATURE:
<223> OTHER INFORMATION: Synthetic sequence: primer

<400> SEQUENCE: 69
tgaggtaccg agctcgaatt tcgacctgca gatcgttcaa acatttggca ataaagttt 59